US012325704B2

(12) United States Patent
Baxter et al.

(10) Patent No.: US 12,325,704 B2
(45) Date of Patent: Jun. 10, 2025

(54) SRPK1 INHIBITORS

(71) Applicant: Exonate Limited, Cambridge (GB)

(72) Inventors: Andrew Douglas Baxter, Horsham (GB); Jonathan Morris, Sydney (AU); Andrew David Morley, Macclesfield (GB)

(73) Assignee: Exonate Limited, Cambridge (GB)

( * ) Notice: Subject to any disclaimer, the term of this patent is extended or adjusted under 35 U.S.C. 154(b) by 88 days.

(21) Appl. No.: 17/880,925

(22) Filed: Aug. 4, 2022

(65) Prior Publication Data

US 2022/0389015 A1 Dec. 8, 2022

Related U.S. Application Data

(63) Continuation of application No. 16/651,182, filed as application No. PCT/GB2018/052735 on Sep. 26, 2018, now Pat. No. 11,420,969.

(30) Foreign Application Priority Data

Sep. 27, 2017 (GB) ........................................ 1715637
Jun. 29, 2018 (GB) ........................................ 1810765

(51) Int. Cl.
*C07D 471/10* (2006.01)
*A61K 9/00* (2006.01)
*C07D 401/12* (2006.01)
*C07D 405/14* (2006.01)
*C07D 413/14* (2006.01)

(52) U.S. Cl.
CPC .......... *C07D 471/10* (2013.01); *A61K 9/0019* (2013.01); *A61K 9/0048* (2013.01); *C07D 401/12* (2013.01); *C07D 405/14* (2013.01); *C07D 413/14* (2013.01)

(58) Field of Classification Search
CPC .. C07D 401/12; C07D 405/14; C07D 413/14; C07D 471/10; A61K 9/0019; A61K 9/0048
See application file for complete search history.

(56) References Cited

U.S. PATENT DOCUMENTS

2007/0135367 A1* 6/2007 Hagiwara ............... A61P 31/12
514/357
2014/0249135 A1 9/2014 Burger et al.
2015/0274668 A1 10/2015 Harper et al.

FOREIGN PATENT DOCUMENTS

WO 03/012105 2/2003
WO WO-2004096795 A2 * 11/2004 ......... C07D 207/416
WO 2005/063293 7/2007

(Continued)

OTHER PUBLICATIONS

International Search Report and Written Opinion in corresponding PCT/GB2018/052735, dated Dec. 10, 2018.

(Continued)

*Primary Examiner* — Theodore R. Howell
(74) *Attorney, Agent, or Firm* — Hovey Williams LLP; Crissa A. Cook

(57) ABSTRACT

Anti-angiogenic treatments, for example treatment of ocular neovascularization or cancer, treatments of hyperpermeability disorders, treatments of neuropathic and neurodegenera- (Continued)

tive disorders, pain treatments, methods of treating or preventing fibrosis and compounds for use in such methods are described.

9 Claims, 1 Drawing Sheet

(56) References Cited

FOREIGN PATENT DOCUMENTS

| WO | 2008/106692 | 9/2008 |
|---|---|---|
| WO | 2008/110777 | 9/2008 |
| WO | 2009/106855 | 9/2009 |
| WO | 2010/058227 | 5/2010 |
| WO | 2009/020198 | 11/2010 |
| WO | 2011/036429 | 3/2011 |
| WO | 2011/148200 | 12/2011 |
| WO | 2014060763 | 4/2014 |
| WO | 2015159103 | 10/2015 |
| WO | 2017064512 | 4/2017 |

OTHER PUBLICATIONS

Batson, et al., "Development of Potent, Selective SRPK1 Inhibitors as Potential Topical Therapeutics for Neovascular Eye Disease", ACS Chem. Biol. 2017, 12, 825-832.

Gammons, et al., "Topical Antiangiogenic SRPK1 Inhibitors Reduce Choroidal Neovascularization in Rodent Models of Exudative AMD", IOVS Sep. 2013, vol. 54, No. 9, 6052-6062.

UK Search Report from priority application GB1715637.3, dated Jun. 20, 2018.

Office Action in corresponding U.S. Appl. No. 16/651,182, dated May 21, 2021.

Office Action in corresponding U.S. Appl. No. 16/651,182, dated Aug. 3, 2021.

Office Action in corresponding U.S. Appl. No. 16/651,182, dated Dec. 10, 2021.

Office Action in corresponding Japan Patent Application Serial No. 2020-517549, dated Aug. 19, 2022 (English translation attached).

Registry (STN) [online], May 15, 2015, [Search Date Aug. 5, 2022], CAS Registry No. 1705453-84-4.

\* cited by examiner

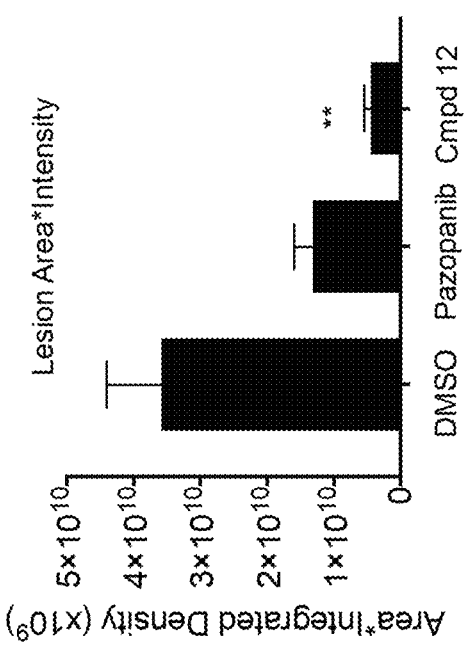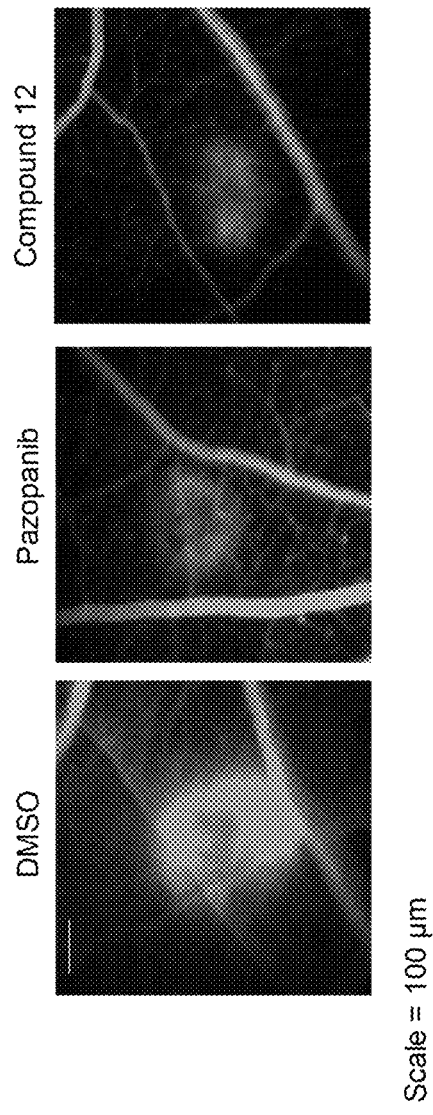

SRPK1 INHIBITORS

RELATED APPLICATIONS

This application is a continuation of U.S. Ser. No. 16/651,182, filed Mar. 26, 2020, which is the U.S. National Stage of International Patent Application No. PCT/GB2018/052735, filed Sep. 26, 2018, each of which is hereby incorporated by reference in its entirety, and which claim priority to United Kingdom Patent Application No. 1810765.6, filed Jun. 29, 2018, and to United Kingdom Patent Application No. 1715637.3, filed Sep. 27, 2017.

FIELD OF THE INVENTION

The present invention relates to anti-angiogenic treatments and compounds for use in anti-angiogenic treatments, particularly of conditions characterised by neovascularisation such as, for example, ocular neovascularization, in particular age-related macular degeneration and macular oedema.

The present invention also relates to treatment of neoplasia, for example treatment of cancer, and compounds for use in treating cancer.

The present invention also relates to treatments of hyperpermeability disorders and compounds for use in treating hyperpermeability disorders.

The present invention also relates to treatments of neuropathic and neurodegenerative disorders and compounds for use in treating neuropathic and neurodegenerative disorders, such as, for example, Alzheimer's disease.

The present invention also relates to pain treatments, and compounds for use in treating pain.

The present invention also relates to methods of reducing the risk of pre-eclampsia, and compounds for use in such methods.

BACKGROUND TO THE INVENTION

Age-related macular degeneration (AMD), a disease causing vision loss that affects the central area of the macula, is the leading cause of blindness in people over 50 years of age. Exudative AMD is the most severe form of AMD primarily arising from the choroidal circulation beneath the macula and characterized by choroidal neovascularization (CNV). CNV, the abnormal growth of new vessels from the choroid into the retinal pigmented epithelium (RPE), is thought to lead to visual loss due to the leakage of blood and serous fluid beneath the RPE that eventually leads to loss of photoreceptors, retinal detachment and dense macular scarring. Vascular endothelial growth factor (VEGF), a key factor in angiogenesis and vascular leakage is up-regulated during the progression of CNV and has become the lead therapeutic target for the treatment of exudative-AMD.

Macular oedema occurs when there is abnormal leakage and accumulation of fluid in the macula from damaged blood vessels in the nearby retina. A common cause of macular oedema is diabetic retinopathy, but it can also occur after eye surgery, in association with age-related macular degeneration, or as a consequence of inflammatory diseases that affect the eye. Any disease that damages blood vessels in the retina can cause macular oedema. Similarly to AMD, VEGF is up-regulated during the progression of this disease and is therefore an attractive therapeutic target for treatment.

VEGF is a complex gene that is alternatively spliced to form a family of multiple isoforms, each isoform differing in biological property, activity and function. Most cells commonly express isoforms $VEGF_{121}$, $VEGF_{165}$, and $VEGF_{189}$, whereas $VEGF_{145}$ and $VEGF_{206}$ are comparatively rare. The majority of VEGF isoforms contain exons 1-5 (the exception being $VEGF_{111}$) but differing portions of exons 6 and 7 that encode heparin sulphate (HS) binding domains. Alterations in the usage of these exons changes the biological properties of alternatively spliced isoforms such as their ability to bind to cell-surface heparan-sulfate proteoglycans and release angiogenic factors.

In 2002 differential splicing of the eighth exon was demonstrated from a proximal splice site (PSS) to a distal splice site (DSS) 66 bases downstream. Alternative splicing in this region generated a second family of isoforms ($VEGF_{xxx}b$), noted for their anti-angiogenic properties. WO 03/102105, the contents of which are incorporated herein by reference in its entirety describes the alternatively spliced isoforms, and their therapeutic significance.

During pathological angiogenesis pro-angiogenic isoforms are selectively upregulated, suggesting $VEGF_{xxx}$ and $VEGF_{xxx}b$ may have separate regulatory pathways. These anti-angiogenic isoforms, such as $VEGF_{165}b$ and $VEGF_{121}b$ have been shown to be potently anti-angiogenic in animal models of retinal and choroidal neovascularisation, following intra-ocular injection, and result in both endothelial and retinal epithelial cell cytoprotection.

The first therapy to be FDA approved for the treatment of neovascular AMD in December 2004 was a $VEGF_{165}$, $VEGF_{189}$ and $VEGF_{206}$ specific aptamer, Pegaptanib Sodium (Macugen). During clinical trials pegaptanib dose-dependently reduced the risk of severe visual acuity loss and slowed the progression of neovascular AMD, but did not result in significant improvement in vision. In 2006 Ranibizumab (Lucentis), a novel humanized anti-VEGF antibody fragment, was FDA approved for the treatment of neovascular AMD. Its approval was based on the results of three clinical trials where, approximately 95% of patients treated monthly with Lucentis (0.5 mg) maintained visual acuity (defined as the loss of <15 letters) and ≤40% improved vision (defined as the gain of ≥15 letters) at one year compared with 11% in the sham control treated group. However, current treatment regimes require Lucentis administration by intra-ocular injection as often as monthly which are not only discomforting for the patient, but also result in increased intraocular pressure and a risk, albeit minor, of endophthalmitis and other severe adverse effects. Furthermore, bevacizumab (Avastin), an anti-VEGF antibody from which Lucentis was derived, was shown to bind $VEGF_{165}b$ with equal potency to $VEGF_{165}$, thus targeting both pro and anti-angiogenic VEGF isoforms.

As both the anti-angiogenic and angiogenic isoforms of VEGF are derived from the same gene, the control of isoform in family is a result of the control of alternative splicing. Some of the pathways that control the splicing of VEGF at the proximal splice site have been identified, implicating the RNA binding protein SRSF1 and its kinase SRPK1 as key requirements for the decision by cells to use the proximal splice site, and hence generate pro-angiogenic isoforms of VEGF. Knockdown of SRPK1 potently reduced VEGF mediated angiogenesis in vivo in tumours and inhibition of SRPK1 and 2 reduced angiogenesis in vivo.

WO 2005/063293 describes a class of SRPK inhibitors including SRPIN340 and derivatives and analogues thereof. WO 2014/060763, WO 2015/159103 and WO 2017/064512 describe SRPK inhibitors targeting SRPK1 specifically for use as anti-angiogenic agents, neuroprotective agents, agents for use in treating or preventing hyperpermeability disorders, as agents for treating pain, and as agents for reducing the risk of, or treatment of, pre-eclampsia.

The present invention is based in part on new small molecule inhibitors targeting SRPK1 specifically for use as anti-angiogenic agents, neuroprotective agents, agents for use in treating or preventing hyperpermeability disorders, as agents for treating pain, and as agents for reducing the risk of, or treatment of, pre-eclampsia.

Increasingly, modern therapeutic regimens use drugs in combination. A large number of commonly used drugs are metabolized by cytochrome P450 (CYP) enzymes. Moreover a large number of this class of enzymes are polymorphic, in particular CYP1A2, CYP2C9, CYP2C19, CYP2D6 and CYP3A4. Patients overexpressing these enzymes are known as 'extensive metabolisers', those under expressing these enzymes are known as 'poor metabolisers'. A drug that inhibits these enzymes can lead to drug-drug interactions which could lead to toxic exposures of other drugs used in combination.

The present invention is also based at least in part on the surprising finding that these low molecular weight compounds do not exhibit any CYP inhibition associated with previously known SRPK1 inhibitors.

Compounds from the current invention will therefore find more widespread therapeutic application than previous described SRPK1 inhibitors.

SUMMARY OF THE INVENTION

In a first aspect the invention provides a compound of Formula (I):

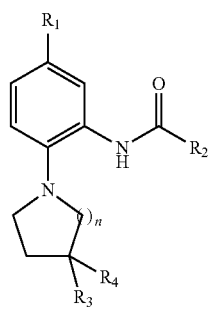

(I)

or a pharmaceutically acceptable salt, solvate, hydrate or prodrug thereof; wherein:
n=1, 2 or 3;
$R_1$ is halogen, difluoromethyl, trifluoromethyl, cyclopropyl, methyl, methoxy or trifluoromethoxy;
$R_2$ is furanyl, optionally having a 4-tetrahydropyranyl or 4-pyridyl substituent, or 2-pyridyl;
$R_3$ is hydroxyl, hydroxymethyl, methoxy, $C_1$-$C_3$ alkyl, carboxy, —C(O)NR$_5$R$_6$ or CH$_2$NR$_5$R$_6$;
$R_4$ is hydrogen, methyl, ethyl, cyclopropyl, phenyl, benzyl or cyclopropylmethyl; or
$R_3$ and $R_4$ together with the adjacent carbon atom form a carbocycle or a heterocycle; and
$R_5$ and $R_6$ are independently selected from hydrogen, methyl, ethyl or propyl; or
$R_5$ and $R_6$ are joined together to form a nitrogen-containing heterocycle;
for use in the treatment or prevention of ocular neovascularisation.

The expression "ocular neovascularisation" includes within its scope diseases and disorders characterised by ocular neovascularisation, including for example choroidal neovascularisation such as age-related macular degeneration. The term "ocular neovascularisation" also includes within its scope diseases and disorders characterized by retinal neovascularisation. For example, the term "ocular neovascularisation" also includes within its scope diseases and conditions such as macular oedema, for example diabetic macular oedema which may be caused by diabetic retinopathy, a complication of diabetes.

In a second aspect the invention provides a compound of Formula (I) or a pharmaceutically acceptable salt, solvate, hydrate or prodrug thereof for use in the topical treatment or prevention of ocular neovascularisation.

The first and second aspects of the invention also provide respective methods of treatment or prevention of ocular neovascularisation by administration of the compound of Formula (I) to a subject in need of such treatment, and respective uses of a compound of Formula (I) in the preparation of a medicament for treatment or prevention of ocular neovascularisation, for example as a dose-dependent treatment and/or as a topical treatment.

It is surprising and not expected from the prior art that the compounds used in the present invention enable dose-dependent or topical treatment or prevention of ocular neovascularisation. Dose-dependent treatment is not inherently predictable, yet is highly desirable and beneficial for effective treatment.

Evaluation of the effect of a new chemical entity on CYP inhibition is critical in determining its suitability as a medicament. The CYP enzymes (Cytochrome P450 enzyme family, including CYP1A2, CYP2C9, CYP2C19, CYP2D6 and CYP3A4) are the main sites for metabolism of drugs, and other exogenous agents. Potent inhibition of any of the CYP enzymes by a drug candidate could lead to an accumulation of the drug to toxic levels in a subject, as well as unfavourable drug-drug interactions (DDIs) in which metabolism of a second drug, used in combination, is impaired or prevented, leading to higher than expected exposure and toxicity issues for the combination drug.

As can be seen from Table 3, while prior art compounds from WO 2015/159103 and WO 2017/064512 are potent SRPK1 inhibitors, they also suffer from being potent inhibitors of at least CYP2C9, CYP2C19, CYP2D6 and CYP3A4 enzymes thus rendering them unsuited for systemic administration. It is surprising and not expected from the prior art that the compounds of the present invention do not exhibit any of the CYP inhibition issues of the prior art compounds while still being potent SRPK1 inhibitors.

The specific compounds of Formula (I), and preferred or exemplified sub-classes of compounds of formula (I) may be particularly mentioned for use in the present invention.

For the avoidance of doubt,

refers to an alkyl bridging unit between the adjacent carbon atoms. Thus, the above mentioned moiety is a methylene (CH$_2$) bridge where n=1; an ethylene bridge (CH$_2$CH$_2$) where n=2; and a propylene bridge (CH$_2$CH$_2$CH$_2$) where n=3.

These compounds of Formula (I) and their pharmaceutically acceptable salts, solvates, hydrates or prodrugs are new and as compounds per se (as well as their use in treatment or prevention of ocular neovascularisation) they constitute a further aspect of the present invention.

Pharmaceutical compositions comprising the novel compounds and the use of the novel compounds and pharmaceutical compositions comprising them in anti-angiogenic treatments (including the treatment and prevention of disorders and diseases characterised by abnormal or excessive angiogenesis), treatments of hyperpermeability disorders, treatments of neuropathic and neurodegenerative disorders, treatment of non-inflammatory pain and methods of reducing the risk of pre-eclampsia as described herein constitute further aspects of the present invention.

Thus, the present invention also provides (i) methods of treating or preventing disorders and diseases characterised by abnormal or excessive angiogenesis as defined herein; (ii) methods of treating or preventing hyperpermeability disorders as defined herein; (iii) methods of treating or preventing neuropathic and neurodegenerative disorders as defined herein; (iv) methods of treating or preventing pain; and (v) methods of reducing the risk of pre-eclampsia, comprising administering a compound of Formula (I) to a patient in need thereof.

In some examples, the compound of Formula (I) may be a compound in which $R_3$ is $C_1$-$C_3$ alkyl, i.e. is selected from methyl, ethyl and propyl.

In some examples, the compound of Formula (I) may be a compound in which:
  $R_3$ is hydroxyl, hydroxymethyl, methoxy, methyl or carboxy; and
  $R_4$ is methyl, ethyl, cyclopropyl, phenyl, benzyl or cyclopropylmethyl.

In some examples, the compound of Formula (I) may be a compound in which $R_3$ is hydroxyl and $R_4$ is methyl, ethyl, cyclopropyl, phenyl, benzyl or cyclopropylmethyl.

In some examples, the compound of Formula (I) may be a compound in which:
  $R_3$ is —C(O)NR$_5$R$_6$ or CH$_2$NR$_5$R$_6$;
  $R_4$ is hydrogen, methyl, ethyl, cyclopropyl, phenyl, benzyl or cyclopropylmethyl; and
  $R_5$ and $R_6$ are independently selected from hydrogen, methyl, ethyl or propyl; or
  $R_5$ and $R_6$ are joined together to form a nitrogen-containing heterocycle;

In some examples, the compound of Formula (I) may be a compound in which n=1 or 3; and wherein the compound is enantiomerically pure.

In some examples, the compound of Formula (I) may be a compound in which:
  n=1 or 3;
  $R_3$ is hydroxyl, —C(O)NR$_5$R$_6$ or CH$_2$NR$_5$R$_6$;
  $R_4$ is hydrogen or methyl;
  $R_5$ and $R_6$ are independently selected from hydrogen and methyl; or
  $R_5$ and $R_6$ are joined together to form a nitrogen-containing heterocycle; and
  wherein the compound is the R enantiomer or the S enantiomer.

In some examples, the compound of Formula (I) may be a compound in which $R_1$ is chloro, difluoromethyl, trifluoromethyl, cyclopropyl, methyl, methoxy or trifluoromethoxy, for example chloro, trifluoromethyl or cyclopropyl.

In some examples, the compound of Formula (I) may be a compound of Formula (II):

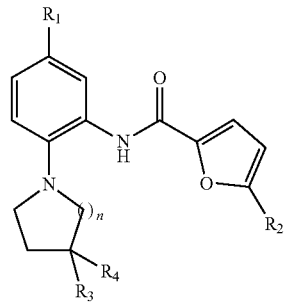

(II)

or a pharmaceutically acceptable salt, solvate, hydrate or prodrug thereof; wherein:
  n=1, 2 or 3;
  $R_1$ is halogen, difluoromethyl, trifluoromethyl, cyclopropyl, methyl, methoxy or trifluoromethoxy;
  $R_2$ is 4-tetrahydropyranyl or 4-pyridyl;
  $R_3$ is hydroxyl, hydroxymethyl, methoxy, $C_1$-$C_3$ alkyl, carboxy, —C(O)NR$_5$R$_6$ or CH$_2$NR$_5$R$_6$;
  $R_4$ is hydrogen, methyl, ethyl, cyclopropyl, phenyl, benzyl or cyclopropylmethyl; and
  $R_5$ and $R_6$ are independently selected from hydrogen, methyl, ethyl or propyl; or
  $R_5$ and $R_6$ are joined together to form a nitrogen-containing heterocycle.

In some examples, the compound of Formula (I) may be a compound of Formula (IIa):

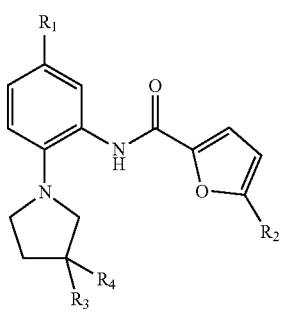

(IIa)

or a pharmaceutically acceptable salt, solvate, hydrate or prodrug thereof; wherein:
  $R_1$ is halogen, difluoromethyl, trifluoromethyl, cyclopropyl, methyl, methoxy or trifluoromethoxy;
  $R_2$ is 4-tetrahydropyranyl or 4-pyridyl;
  $R_3$ is hydroxyl, hydroxymethyl, methoxy, $C_1$-$C_3$ alkyl, carboxy, —C(O)NR$_5$R$_6$ or CH$_2$NR$_5$R$_6$;
  $R_4$ is hydrogen, methyl, ethyl, cyclopropyl, phenyl, benzyl or cyclopropylmethyl; and
  $R_5$ and $R_6$ are independently selected from hydrogen, methyl, ethyl or propyl; or
  $R_5$ and $R_6$ are joined together to form a nitrogen-containing heterocycle.

In some examples, the compound of Formula (I) may be a compound of Formula (IIb):

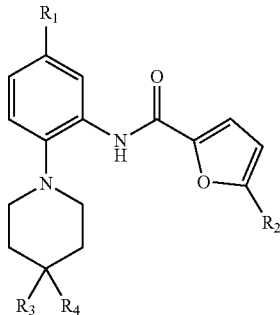

(IIb)

or a pharmaceutically acceptable salt, solvate, hydrate or prodrug thereof; wherein:
- $R_1$ is halogen, difluoromethyl, trifluoromethyl, cyclopropyl, methyl, methoxy or trifluoromethoxy;
- $R_2$ is 4-tetrahydropyranyl or 4-pyridyl;
- $R_3$ is hydroxyl, hydroxymethyl, methoxy, $C_1$-$C_3$ alkyl, carboxy, —C(O)NR$_5$R$_6$ or CH$_2$NR$_5$R$_6$;
- $R_4$ is hydrogen, methyl, ethyl, cyclopropyl, phenyl, benzyl or cyclopropylmethyl; and
- $R_5$ and $R_6$ are independently selected from hydrogen, methyl, ethyl or propyl; or
- $R_5$ and $R_6$ are joined together to form a nitrogen-containing heterocycle.

In some examples, the compound of Formula (I) may be a compound of Formula (IIc):

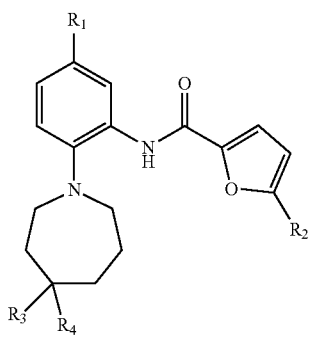

(IIc)

or a pharmaceutically acceptable salt, solvate, hydrate or prodrug thereof; wherein:
- $R_1$ is halogen, difluoromethyl, trifluoromethyl, cyclopropyl, methyl, methoxy or trifluoromethoxy;
- $R_2$ is 4-tetrahydropyranyl or 4-pyridyl;
- $R_3$ is hydroxyl, hydroxymethyl, methoxy, $C_1$-$C_3$ alkyl, carboxy, —C(O)NR$_5$R$_6$ or CH$_2$NR$_5$R$_6$;
- $R_4$ is hydrogen, methyl, ethyl, cyclopropyl, phenyl, benzyl or cyclopropylmethyl; and
- $R_5$ and $R_6$ are independently selected from hydrogen, methyl, ethyl or propyl; or
- $R_5$ and $R_6$ are joined together to form a nitrogen-containing heterocycle.

In some examples, the compound of Formula (II), (IIa), (IIb) or (IIc) may be a compound in which $R_3$ is $C_1$-$C_3$ alkyl, i.e. is selected from methyl, ethyl and propyl.

In some examples, the compound of Formula (II), (IIa), (IIb) or (IIc) may be a compound in which:
- $R_3$ is hydroxyl, hydroxymethyl, methoxy, methyl, carboxy, —C(O)NR$_5$R$_6$ or CH$_2$NR$_5$R$_6$;
- $R_4$ is methyl, ethyl, cyclopropyl, phenyl, benzyl or cyclopropylmethyl; and
- $R_5$ and $R_6$ are independently selected from hydrogen, methyl, ethyl or propyl; or
- $R_5$ and $R_6$ are joined together to form a nitrogen-containing heterocycle.

In some examples, the compound of Formula (II), (IIa), (IIb) or (IIc) may be a compound in which $R_3$ is hydroxyl; and $R_4$ is methyl, ethyl, cyclopropyl, phenyl, benzyl or cyclopropylmethyl.

In some examples, the compound of Formula (II), (IIa), (IIb) or (IIc) may be a compound in which:
- $R_3$ is —C(O)NR$_5$R$_6$ or CH$_2$NR$_5$R$_6$;
- $R_4$ is methyl, ethyl, cyclopropyl, phenyl, benzyl or cyclopropylmethyl; and
- $R_5$ and $R_6$ are independently selected from hydrogen and methyl; or
- $R_5$ and $R_6$ are joined together to form a nitrogen-containing heterocycle, for example a 5- or 6-membered nitrogen containing heterocycle, for example a 5- or 6-membered unsaturated heterocycle.

In some examples, the compound of Formula (II), (IIa), (IIb) or (IIc) may be a compound in which $R_3$ is —C(O)NR$_5$R$_6$ or CH$_2$NR$_5$R$_6$; and $R_5$ and $R_6$ are joined together to form a nitrogen-containing heterocycle; and wherein the nitrogen containing heterocycle is a pyrrolidine, a piperidine or a morpholine heterocycle.

In some examples, the compound of Formula (II), (IIa), (IIb) or (IIc) may be a compound in which n=1 or 3; and the compound is enantiomerically pure.

In some examples, the compound of Formula (II), (IIa), (IIb) or (IIc) may be a compound in which:
- n=1 or 3;
- $R_3$ is hydroxyl, —C(O)NR$_5$R$_6$ or CH$_2$NR$_5$R$_6$;
- $R_4$ is hydrogen or methyl;
- $R_5$ and $R_6$ are independently selected from hydrogen and methyl; or
- $R_5$ and $R_6$ are joined together to form a nitrogen-containing heterocycle; and
- wherein the compound is the R enantiomer or the S enantiomer.

In some examples, the compound of Formula (II), (IIa), (IIb) or (IIc) may be a compound in which $R_1$ is chloro, difluoromethyl, trifluoromethyl, cyclopropyl, methyl, methoxy or trifluoromethoxy, for example chloro, trifluoromethyl or cyclopropyl.

In some examples, the compound of Formula (I) may be a compound of Formula (III):

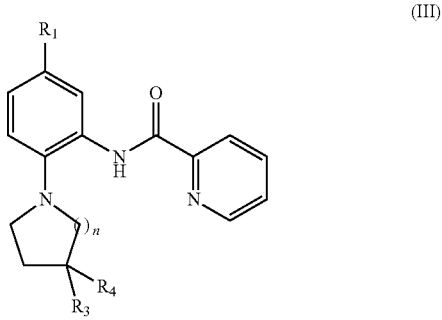

(III)

or a pharmaceutically acceptable salt, solvate, hydrate or prodrug thereof; wherein:
n=1, 2 or 3;
$R_1$ is halogen, difluoromethyl, trifluoromethyl, cyclopropyl, methyl, methoxy or trifluoromethoxy;
$R_2$ is hydroxyl, hydroxymethyl, methoxy, $C_1$-$C_3$ alkyl, carboxy, —C(O)NR$_4$R$_5$ or CH$_2$NR$_4$R$_5$;
$R_3$ is hydrogen, methyl, ethyl, cyclopropyl, phenyl, benzyl or cyclopropylmethyl; and
$R_4$ and $R_5$ are independently selected from hydrogen, methyl, ethyl or propyl; or
$R_4$ and $R_5$ are joined together to form a nitrogen-containing heterocycle.

In some examples, the compound of Formula (I) may be a compound of Formula (IIIa):

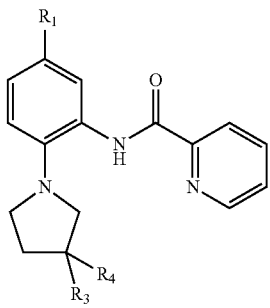

(IIIa)

or a pharmaceutically acceptable salt, solvate, hydrate or prodrug thereof; wherein:
$R_1$ is halogen, difluoromethyl, trifluoromethyl, cyclopropyl, methyl, methoxy or trifluoromethoxy;
$R_2$ is hydroxyl, hydroxymethyl, methoxy, $C_1$-$C_3$ alkyl, carboxy, —C(O)NR$_4$R$_5$ or CH$_2$NR$_4$R$_5$;
$R_3$ is hydrogen, methyl, ethyl, cyclopropyl, phenyl, benzyl or cyclopropylmethyl; and
$R_4$ and $R_5$ are independently selected from hydrogen, methyl, ethyl or propyl; or
$R_4$ and $R_5$ are joined together to form a nitrogen-containing heterocycle.

In some examples, the compound of Formula (I) may be a compound of Formula (IIIb):

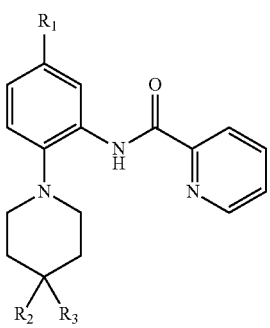

(IIIb)

or a pharmaceutically acceptable salt, solvate, hydrate or prodrug thereof; wherein:
$R_1$ is halogen, difluoromethyl, trifluoromethyl, cyclopropyl, methyl, methoxy or trifluoromethoxy;
$R_2$ is hydroxyl, hydroxymethyl, methoxy, $C_1$-$C_3$ alkyl, carboxy, —C(O)NR$_4$R$_5$ or CH$_2$NR$_4$R$_5$;
$R_3$ is hydrogen, methyl, ethyl, cyclopropyl, phenyl, benzyl or cyclopropylmethyl; and
$R_4$ and $R_5$ are independently selected from hydrogen, methyl, ethyl or propyl; or
$R_4$ and $R_5$ are joined together to form a nitrogen-containing heterocycle.

In some examples, the compound of Formula (I) may be a compound of Formula (IIIc):

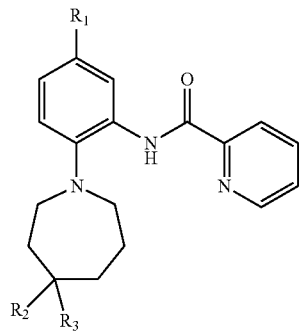

(IIIc)

or a pharmaceutically acceptable salt, solvate, hydrate or prodrug thereof; wherein:
$R_1$ is halogen, difluoromethyl, trifluoromethyl, cyclopropyl, methyl, methoxy or trifluoromethoxy;
$R_2$ is hydroxyl, hydroxymethyl, methoxy, $C_1$-$C_3$ alkyl, carboxy, —C(O)NR$_4$R$_5$ or CH$_2$NR$_4$R$_5$;
$R_3$ is hydrogen, methyl, ethyl, cyclopropyl, phenyl, benzyl or cyclopropylmethyl; and
$R_4$ and $R_5$ are independently selected from hydrogen, methyl, ethyl or propyl; or
$R_4$ and $R_5$ are joined together to form a nitrogen-containing heterocycle.

In some examples, the compound of Formula (III), (IIIa), (IIIb) or (IIIc) may be a compound in which $R_3$ is $C_1$-$C_3$ alkyl, i.e. is selected from methyl, ethyl and propyl.

In some examples, the compound of Formula (III), (IIIa), (IIIb) or (IIIc) may be a compound in which:
$R_2$ is hydroxyl, hydroxymethyl, methoxy, methyl or carboxy; and
$R_3$ is methyl, ethyl, cyclopropyl, phenyl, benzyl or cyclopropylmethyl.

In some examples, the compound of Formula (III), (IIIa), (IIIb) or (IIIc) may be a compound in which $R_2$ is hydroxyl; and $R_3$ is methyl, ethyl, cyclopropyl, phenyl, benzyl or cyclopropylmethyl.

In some examples, the compound of Formula (III), (IIIa), (IIIb) or (IIIc) may be a compound in which:
$R_2$ is —C(O)NR$_4$R$_5$ or CH$_2$NR$_4$R$_5$;
$R_3$ is methyl, ethyl, cyclopropyl, phenyl, benzyl or cyclopropylmethyl; and
$R_4$ and $R_5$ are independently selected from hydrogen and methyl; or
$R_4$ and $R_5$ are joined together to form a nitrogen-containing heterocycle, for example a 5- or 6-membered nitrogen containing heterocycle, for example a 5- or 6-membered unsaturated heterocycle.

In some examples, the compound of Formula (III), (IIIa), (IIIb) or (IIIc) may be a compound in which:
$R_3$ is —C(O)NR$_5$R$_6$ or CH$_2$NR$_5$R$_6$; and $R_5$ and $R_6$ are joined together to form a nitrogen-containing heterocycle; and wherein the nitrogen containing heterocycle is a pyrrolidine, a piperidine or a morpholine heterocycle.

In some examples, the compound of Formula (III), (IIIa), (IIIb) or (IIIc) may be a compound in which n=1 or 3; and wherein the compound is enantiomerically pure.

In some examples, the compound of Formula (III), (IIIa), (IIIb) or (IIIc) may be a compound in which:
n=1 or 3;
$R_2$ is hydroxyl-C(O)$NR_4R_5$ or $CH_2NR_4R_5$;
$R_3$ is hydrogen or methyl;
$R_4$ and $R_5$ are independently selected from hydrogen and methyl; or
$R_4$ and $R_5$ are joined together to form a nitrogen-containing heterocycle; and
wherein the compound is the R enantiomer or the S enantiomer.

In some examples, the compound of Formula (III), (IIIa), (IIIb) or (IIIc) may be a compound in which $R_1$ is chloro, difluoromethyl, trifluoromethyl, cyclopropyl, methyl, methoxy or trifluoromethoxy, for example chloro, trifluoromethyl or cyclopropyl.

In some examples, the compound of Formula (I), (II), (IIa), (IIb) or (IIc) may be a compound in which $R_1$ and $R_2$ are as defined above and $R_3$ and $R_4$ together with the adjacent methylene group (i.e. the ring carbon atom) form a carbocycle or heterocycle, for example a 3 to 6 membered carbocycle or a 3 to 6 membered heterocycle thus forming a spiro compound. The carbocycle or heterocycle, for example the 3 to 6 membered carbocycle or the 3 to 6 membered heterocycle may be an aromatic or non-aromatic carbocycle or heterocycle. The heterocycle may comprise one or more heteroatom selected from O, N or S. For example, there are mentioned compounds in which the carbocycle or heterocycle is a 5- or 6-membered carbocycle or heterocycle, each of which may have a substituent, particularly a non-aromatic 5- or 6-membered carbocycle or heterocycle, each of which may have a substituent. In some examples, the 5- or 6-membered heterocycle comprises one nitrogen atom. In some examples, the 5- or 6-membered heterocycle comprises one nitrogen atom, and one further heteroatom selected from O, N and S. Particular examples of the 5- or 6-membered carbocycle include cyclopentyl, cyclopentadienyl, cyclohexyl and phenyl. Particular examples of the 5- or 6-membered heterocycle include pyrrolidinyl, piperidinyl, morpholino, piperazinyl, each of which may have one or more substituent. In some examples, the 5- or 6-membered carbocycle or heterocycle comprises a substituent selected from $C_{1-6}$ alkyl, halogen, hydroxy, $C_{1-6}$ alkoxy, oxo, cyano, amino.

In some examples, the compound of Formula (III), (IIIa), (IIIb) or (IIIc) may be a compound in which $R_1$ is as defined above and $R_2$ and $R_3$ together with the adjacent methylene group (i.e. the ring carbon atom) form a carbocycle or heterocycle, for example a 3 to 6 membered carbocycle or a 3 to 6 membered heterocycle thus forming a spiro compound. The carbocycle or heterocycle, for example the 3 to 6 membered carbocycle or the 3 to 6 membered heterocycle may be an aromatic or non-aromatic carbocycle or heterocycle. The heterocycle may comprise one or more heteroatom selected from O, N or S. For example, there are mentioned compounds in which the carbocycle or heterocycle is a 5- or 6-membered carbocycle or heterocycle, each of which may have a substituent, particularly a non-aromatic 5- or 6-membered carbocycle or heterocycle, each of which may have a substituent. In some examples, the 5- or 6-membered heterocycle comprises one nitrogen atom. In some examples, the 5- or 6-membered heterocycle comprises one nitrogen atom, and one further heteroatom selected from O, N and S. Particular examples of the 5- or 6-membered carbocycle include cyclopentyl, cyclopentadienyl, cyclohexyl and phenyl. Particular examples of the 5- or 6-membered heterocycle include pyrrolidinyl, piperidinyl, morpholino, piperazinyl, each of which may have one or more substituent. In some examples, the 5- or 6-membered carbocycle or heterocycle comprises a substituent selected from $C_{1-6}$ alkyl, halogen, hydroxy, $C_{1-6}$ alkoxy, oxo, cyano, amino.

In some examples, the compound of Formula (I), (II), (IIa), (IIb), (IIc), (III), (IIIa), (IIIb) or (IIIc) may be a compound in which $R_1$ is halogen, selected from fluoro, chloro, bromo, and iodo. In some examples, the compound of Formula (I), (II), (IIa), (IIb), (IIc), (III), (IIIa), (IIIb) or (IIIc) may be a compound in which $R_1$ is chloro.

In some examples, the compound of Formula (I) may have an $IC_{50}$ for CYP1A2 of at least 5 μM, for example at least 6 μM, for example at least 7 μM, for example at least 8 μM, for example at least 9 μM, for example at least 10 μM, for example at least 15 μM, for example at least 20 μM, for example at least 25 μM, for example about 30 μM.

In some examples, the compound of Formula (I) may have an $IC_{50}$ for CYP2C9 of at least 5 μM, for example at least 6 μM, for example at least 7 μM, for example at least 8 μM, for example at least 9 μM, for example at least 10 μM, for example at least 15 μM, for example at least 20 μM, for example at least 25 μM, for example about 30 μM.

In some examples, the compound of Formula (I) may have an $IC_{50}$ for CYP2C19 of at least 5 μM, for example at least 6 μM, for example at least 7 μM, for example at least 8 μM, for example at least 9 μM, for example at least 10 μM, for example at least 15 μM, for example at least 20 μM, for example at least 25 μM, for example about 30 μM.

In some examples, the compound of Formula (I) may have an $IC_{50}$ for CYP2D6 of at least 5 μM, for example at least 6 μM, for example at least 7 μM, for example at least 8 μM, for example at least 9 μM, for example at least 10 μM, for example at least 15 μM, for example at least 20 μM, for example at least 25 μM, for example about 30 μM.

In some examples, the compound of Formula (I) may have an $IC_{50}$ for CYP3A4 of at least 5 μM, for example at least 6 μM, for example at least 7 μM, for example at least 8 μM, for example at least 9 μM, for example at least 10 μM, for example at least 15 μM, for example at least 20 μM, for example at least 25 μM, for example about 30 μM.

In some examples, the compound of Formula (I) may be a compound of Table 2. Particularly mentioned compounds of Formula (I) include:
N-(2-(4-hydroxy-4-methylpiperidin-1-yl)-5-(trifluoromethyl)phenyl)picolinamide;
N-(5-chloro-2-(4-hydroxy-4-methylpiperidin-1-yl)-phenyl)picolinamide;
N-(5-cyclopropyl-2-(4-hydroxy-4-methylpiperidin-1-yl)phenyl)-picolinamide;
N-(2-(4-hydroxy-4-methylpiperidin-1-yl)-5-(trifluoromethyl)phenyl)-5-(pyridin-4-yl)furan-2-carboxamide;
N-(5-chloro-2-(4-hydroxy-4-methylpiperidin-1-yl)phenyl)-5-(pyridin-4-yl)furan-2-carboxamide;
N-(5-cyclopropyl-2-(4-hydroxy-4-methylpiperidin-1-yl)phenyl)-5-(pyridin-4-yl)furan-2-carboxamide;
N-(5-(difluoromethyl)-2-(4-hydroxy-4-methyl-piperidin-1-yl)phenyl)-5-(pyridin-4-yl)furan-2-carboxamide;
N-(2-(4-hydroxy-4-methylpiperidin-1-yl)-5-methylphenyl)-5-(pyridin-4-yl)furan-2-carboxamide;
N-(2-(4-hydroxy-4-methylpiperidin-1-yl)-5-methoxyphenyl)-5-(pyridin-4-yl)furan-2-carboxamide;

N-(2-(4-hydroxy-4-methylpiperidin-1-yl)-5-(trifluoromethoxy)phenyl)-5-(pyridin-4-yl)furan-2-carboxamide;
N-(2-(4-hydroxy-4-methylpiperidin-1-yl)-5-(trifluoromethyl)-phenyl)-5-(tetrahydro-2H-pyran-4-yl)furan-2-carboxamide;
N-(5-cyclopropyl-2-(4-hydroxy-4-methylpiperidin-1-yl)phenyl)-5-(pyridin-4-yl)furan-2-carboxamide;
N-(2-(4-hydroxy-4-methylpiperidin-1-yl)-5-methylphenyl)-5-(tetrahydro-2H-pyran-4-yl)furan-2-carboxamide; N-(5-(difluoromethyl)-2-(4-hydroxy-4-methyl-piperidin-1-yl)phenyl)-5-(tetrahydro-2H-pyran-4-yl)furan-2-carboxamide;
N-(2-(4-hydroxy-4-methylpiperidin-1-yl)-5-methoxyphenyl)-5-(tetrahydro-2H-pyran-4-yl)furan-2-carboxamide;
N-(2-(4-hydroxy-4-methylpiperidin-1-yl)-5-(trifluoromethoxy)phenyl)-5-(tetrahydro-2H-pyran-4-yl)furan-2-carboxamide;
N-(5-cyclopropyl-2-(4-hydroxy-4-methylpiperidin-1-yl)phenyl)-5-(tetrahydro-2H-pyran-4-yl)furan-2-carboxamide;
N-(2-(4-methoxy-4-methylpiperidin-1-yl)-5-(trifluoromethyl)-phenyl)-5-(tetrahydro-2H-pyran-4-yl)furan-2-carboxamide;
N-(2-(4-hydroxy-4-methylazepan-1-yl)-5-(trifluoromethyl)phenyl)-5-(pyridin-4-yl)furan-2-carboxamide;
N-(2-(4-ethyl-4-hydroxypiperidin-1-yl)-5-(trifluoromethyl)phenyl)-5-(tetrahydro-2H-pyran-4-yl)furan-2-carboxamide;
N-(2-(4-cyclopropyl-4-hydroxypiperidin-1-yl)-5-(trifluoromethyl)-phenyl)-5-(tetrahydro-2H-pyran-4-yl)furan-2-carboxamide;
N-(2-(4-hydroxy-4-phenylpiperidin-1-yl)-5-(trifluoromethyl)-phenyl)-5-(tetrahydro-2H-pyran-4-yl)furan-2-carboxamide;
N-(2-(4-(cyclopropylmethyl)-4-hydroxypiperidin-1-yl)-5-(trifluoromethyl)phenyl)-5-(tetrahydro-2H-pyran-4-yl)furan-2-carboxamide;
N-(2-(4-(hydroxymethyl)-4-methylpiperidin-1-yl)-5-(trifluoromethyl)phenyl)-5-(pyridin-4-yl)furan-2-carboxamide;
N-(2-(4-(hydroxymethyl)-4-methylpiperidin-1-yl)-5-(trifluoromethyl)phenyl)-5-(tetrahydro-2H-pyran-4-yl)furan-2-carboxamide;
4-methyl-1-(2-(5-(pyridin-4-yl)furan-2-carboxamido)-4-(trifluoromethyl)phenyl)-piperidine-4-carboxylic acid;
4-methyl-1-(2-(5-(tetrahydro-2H-pyran-4-yl)furan-2-carboxamido)-4-(trifluoromethyl)phenyl)-piperidine-4-carboxylic acid;
N-(2-(4,4-dimethylpiperidin-1-yl)-5-(trifluoromethyl)phenyl)-5-(pyridin-4-yl)furan-2-carboxamide;
N-(2-(4,4-dimethylpiperidin-1-yl)-5-(trifluoromethyl)phenyl)-5-(tetrahydro-2H-pyran-4-yl)furan-2-carboxamide;
1-(2-(picolinamido)-4-(trifluoromethyl)phenyl)-piperidine-4-carboxylic acid;
N-(2-(4-(hydroxymethyl)piperidin-1-yl)-5-(trifluoromethyl)phenyl)picolinamide;
N-(2-(4-hydroxypiperidin-1-yl)-5-(trifluoromethyl)-phenyl)-5-(pyridin-4-yl)furan-2-carboxamide;
N-(2-(4-hydroxypiperidin-1-yl)-5-(trifluoromethyl)-phenyl)-5-(tetrahydro-2H-pyran-4-yl)furan-2-carboxamide;
N-(2-(4-methylpiperidin-1-yl)-5-(trifluoromethyl)-phenyl)-5-(pyridin-4-yl)furan-2-carboxamide;
N-(2-(4-methylpiperidin-1-yl)-5-(trifluoromethyl)-phenyl)-5-(tetrahydro-2H-pyran-4-yl)furan-2-carboxamide;
N-(5-cyclopropyl-2-(4-hydroxypiperidin-1-yl)phenyl)-5-(tetrahydro-2H-pyran-4-yl)furan-2-carboxamide;
N-(5-chloro-2-(4-hydroxypiperidin-1-yl)phenyl)-5-(tetrahydro-2H-pyran-4-yl)furan-2-carboxamide;
N-(2-(4-hydroxypiperidin-1-yl)-5-methylphenyl)-5-(tetrahydro-2H-pyran-4-yl)furan-2-carboxamide;
(R)—N-(2-(4-hydroxy-4-methylazepan-1-yl)-5-(trifluoromethyl)phenyl)-5-(pyridin-4-yl)furan-2-carboxamide;
(S)—N-(2-(4-hydroxy-4-methylazepan-1-yl)-5-(trifluoromethyl)phenyl)-5-(pyridin-4-yl)furan-2-carboxamide;
(R)—N-(5-chloro-2-(4-hydroxy-4-methylazepan-1-yl)phenyl)-5-(pyridin-4-yl)furan-2-carboxamide;
(S)—N-(5-chloro-2-(4-hydroxy-4-methylazepan-1-yl)phenyl)-5-(pyridin-4-yl)furan-2-carboxamide;
(R)—N-(5-cyclopropyl-2-(4-hydroxy-4-methylazepan-1-yl)phenyl)-5-(pyridin-4-yl)-furan-2-carboxamide;
(S)—N-(5-cyclopropyl-2-(4-hydroxy-4-methylazepan-1-yl)phenyl)-5-(pyridin-4-yl)-furan-2-carboxamide;
(R)—N-(2-(4-hydroxy-4-methylazepan-1-yl)-5-(trifluoromethyl)phenyl)-5-(tetrahydro-2H-pyran-4-yl)furan-2-carboxamide;
(S)—N-(2-(4-hydroxy-4-methylazepan-1-yl)-5-(trifluoromethyl)phenyl)-5-(tetrahydro-2H-pyran-4-yl)furan-2-carboxamide;
(R)—N-(5-chloro-2-(4-hydroxy-4-methylazepan-1-yl)phenyl)-5-(tetrahydro-2H-pyran-4-yl)furan-2-carboxamide;
(S)—N-(5-chloro-2-(4-hydroxy-4-methylazepan-1-yl)phenyl)-5-(tetrahydro-2H-pyran-4-yl)furan-2-carboxamide;
(R)—N-(5-cyclopropyl-2-(4-hydroxy-4-methylazepan-1-yl)phenyl)-5-(tetrahydro-2H-pyran-4-yl)furan-2-carboxamide;
(S)—N-(5-cyclopropyl-2-(4-hydroxy-4-methylazepan-1-yl)phenyl)-5-(tetrahydro-2H-pyran-4-yl)furan-2-carboxamide;
(R)—N-(2-(4-hydroxyazepan-1-yl)-5-(trifluoromethyl)-phenyl)picolinamide;
(S)—N-(2-(4-hydroxyazepan-1-yl)-5-(trifluoromethyl)-phenyl)picolinamide;
(R)—N-(2-(4-hydroxyazepan-1-yl)-5-(trifluoromethyl)-phenyl)-5-(pyridin-4-yl)furan-2-carboxamide;
(S)—N-(2-(4-hydroxyazepan-1-yl)-5-(trifluoromethyl)-phenyl)-5-(pyridin-4-yl)furan-2-carboxamide;
(R)—N-(5-chloro-2-(4-hydroxyazepan-1-yl)phenyl)-5-(pyridin-4-yl)furan-2-carboxamide;
(S)—N-(5-chloro-2-(4-hydroxyazepan-1-yl)phenyl)-5-(pyridin-4-yl)furan-2-carboxamide;
(R)—N-(5-cyclopropyl-2-(4-hydroxyazepan-1-yl)phenyl)-5-(pyridin-4-yl)furan-2-carboxamide;
(S)—N-(5-cyclopropyl-2-(4-hydroxyazepan-1-yl)phenyl)-5-(pyridin-4-yl)furan-2-carboxamide;
(R)—N-(2-(4-hydroxyazepan-1-yl)-5-(trifluoromethyl)-phenyl)-5-(tetrahydro-2H-pyran-4-yl)furan-2-carboxamide;
(S)—N-(2-(4-hydroxyazepan-1-yl)-5-(trifluoromethyl)-phenyl)-5-(tetrahydro-2H-pyran-4-yl)furan-2-carboxamide;
(R)—N-(5-chloro-2-(4-hydroxyazepan-1-yl)phenyl)-5-(tetrahydro-2H-pyran-4-yl)furan-2-carboxamide;
(S)—N-(5-chloro-2-(4-hydroxyazepan-1-yl)phenyl)-5-(tetrahydro-2H-pyran-4-yl)furan-2-carboxamide;
(R)—N-(5-cyclopropyl-2-(4-hydroxyazepan-1-yl)phenyl)-5-(tetrahydro-2H-pyran-4-yl)furan-2-carboxamide;
(S)—N-(5-cyclopropyl-2-(4-hydroxyazepan-1-yl)phenyl)-5-(tetrahydro-2H-pyran-4-yl)furan-2-carboxamide;
(R)—N-(2-(3-hydroxy-3-methylpyrrolidin-1-yl)-5-(trifluoromethyl)phenyl)-5-(tetrahydro-2H-pyran-4-yl)furan-2-carboxamide;

(S)—N-(2-(3-hydroxy-3-methylpyrrolidin-1-yl)-5-(trifluoromethyl)phenyl)-5-(tetrahydro-2H-pyran-4-yl)furan-2-carboxamide;

(R)—N-(2-(3-hydroxy-3-methylpyrrolidin-1-yl)-5-(trifluoromethyl)phenyl)-5-(pyridin-4-yl)furan-2-carboxamide;

(S)—N-(2-(3-hydroxy-3-methylpyrrolidin-1-yl)-5-(trifluoromethyl)phenyl)-5-(pyridin-4-yl)furan-2-carboxamide;

(R)—N-(2-(3-hydroxy-3-methylpyrrolidin-1-yl)-5-methylphenyl)-5-(tetrahydro-2H-pyran-4-yl)furan-2-carboxamide;

(S)—N-(2-(3-hydroxy-3-methylpyrrolidin-1-yl)-5-methylphenyl)-5-(tetrahydro-2H-pyran-4-yl)furan-2-carboxamide;

(R)—N-(5-cyclopropyl-2-(3-hydroxy-3-methylpyrrolidin-1-yl)phenyl)-5-(tetrahydro-2H-pyran-4-yl)furan-2-carboxamide;

(S)—N-(5-cyclopropyl-2-(3-hydroxy-3-methylpyrrolidin-1-yl)phenyl)-5-(tetrahydro-2H-pyran-4-yl)furan-2-carboxamide;

(R)—N-(5-chloro-2-(3-hydroxy-3-methylpyrrolidin-1-yl)phenyl)-5-(tetrahydro-2H-pyran-4-yl)furan-2-carboxamide;

(S)—N-(5-chloro-2-(3-hydroxy-3-methylpyrrolidin-1-yl)phenyl)-5-(tetrahydro-2H-pyran-4-yl)furan-2-carboxamide;

(R)—N-(2-(3-hydroxy-3-methylpyrrolidin-1-yl)-5-(trifluoromethyl)-phenyl)-5-(tetrahydro-2H-pyran-4-yl)furan-2-carboxamide;

(S)—N-(2-(3-hydroxy-3-methylpyrrolidin-1-yl)-5-(trifluoromethyl)-phenyl)-5-(tetrahydro-2H-pyran-4-yl)furan-2-carboxamide;

(R)—N-(2-(3-hydroxy-3-methylpyrrolidin-1-yl)-5-(trifluoromethyl)-phenyl)-5-(pyridin-4-yl)furan-2-carboxamide;

(S)—N-(2-(3-hydroxy-3-methylpyrrolidin-1-yl)-5-(trifluoromethyl)-phenyl)-5-(pyridin-4-yl)furan-2-carboxamide;

(R)—N-(2-(3-hydroxypyrrolidin-1-yl)-5-(trifluoromethyl)-phenyl)-5-(pyridin-4-yl)furan-2-carboxamide;

(S)—N-(2-(3-hydroxypyrrolidin-1-yl)-5-(trifluoromethyl)-phenyl)-5-(pyridin-4-yl)furan-2-carboxamide;

(R)—N-(2-(3-hydroxypyrrolidin-1-yl)-5-(trifluoromethyl)-phenyl)-5-(tetrahydro-2H-pyran-4-yl)furan-2-carboxamide;

(S)—N-(2-(3-hydroxypyrrolidin-1-yl)-5-(trifluoromethyl)-phenyl)-5-(tetrahydro-2H-pyran-4-yl)furan-2-carboxamide.

N-(5-cyclopropyl-2-(4-hydroxypiperidin-1-yl)phenyl)-5-(tetrahydro-2H-pyran-4-yl)furan-2-carboxamide N-(5-chloro-2-(4-hydroxypiperidin-1-yl)phenyl)-5-(tetrahydro-2H-pyran-4-yl)furan-2-carboxamide N-(2-(4,4-dimethylpiperidin-1-yl)-5-methylphenyl)-5-(tetrahydro-2H-pyran-4-yl)furan-2-carboxamide N-(5-cyclopropyl-2-(4,4-dimethylpiperidin-1-yl)phenyl)-5-(tetrahydro-2H-pyran-4-yl)furan-2-carboxamide N-(5-chloro-2-(4,4-dimethylpiperidin-1-yl)phenyl)-5-(tetrahydro-2H-pyran-4-yl)furan-2-carboxamide N-(2-(4-(hydroxymethyl)-4-methylpiperidin-1-yl)-5-methylphenyl)-5-(tetrahydro-2H-pyran-4-yl)furan-2-carboxamide N-(5-cyclopropyl-2-(4-(hydroxymethyl)-4-methylpiperidin-1-yl)phenyl)-5-(tetrahydro-2H-pyran-4-yl)furan-2-carboxamide N-(5-chloro-2-(4-(hydroxymethyl)-4-methyl-piperidin-1-yl)phenyl)-5-(tetrahydro-2H-pyran-4-yl)furan-2-carboxamide N-(5-chloro-2-(4-(cyclopropylmethyl)-4-hydroxypiperidin-1-yl)phenyl)-5-(tetrahydro-2H-pyran-4-yl)furan-2-carboxamide N-(2-(4-(cyclopropylmethyl)-4-hydroxypiperidin-1-yl)-5-methylphenyl)-5-(tetrahydro-2H-pyran-4-yl)furan-2-carboxamide N-(5-cyclopropyl-2-(4-(cyclopropylmethyl)-4-hydroxypiperidin-1-yl)phenyl)-5-(tetrahydro-2H-pyran-4-yl)furan-2-carboxamide 4-methyl-1-(2-(5-(pyridin-4-yl)furan-2-carboxamido)-4-(trifluoromethyl)phenyl)-piperidine-4-carboxamide N,4-dimethyl-1-(2-(5-(pyridin-4-yl)furan-2-carboxamido)-4-(trifluoromethyl)phenyl)-piperidine-4-carboxamide N,N,4-trimethyl-1-(2-(5-(pyridin-4-yl)furan-2-carboxamido)-4-(trifluoromethyl)phenyl)-piperidine-4-carboxamide 4-methyl-1-(2-(5-(tetrahydro-2H-pyran-4-yl)furan-2-carboxamido)-4-(trifluoromethyl)-phenyl)piperidine-4-carboxamide N,4-dimethyl-1-(2-(5-(tetrahydro-2H-pyran-4-yl)furan-2-carboxamido)-4-(trifluoromethyl)-phenyl)piperidine-4-carboxamide N,N,4-trimethyl-1-(2-(5-(tetrahydro-2H-pyran-4-yl)furan-2-carboxamido)-4-(trifluoromethyl)-phenyl)piperidine-4-carboxamide N-(2-(4-(aminomethyl)-4-methylpiperidin-1-yl)-5-(trifluoromethyl)phenyl)-5-(pyridin-4-yl)furan-2-carboxamide N-(2-(4-methyl-4-((methylamino)-methyl)piperidin-1-yl)-5-(trifluoromethyl)phenyl)-5-(pyridin-4-yl)furan-2-carboxamide N-(2-(4-((dimethylamino)methyl)-4-methyl-piperidin-1-yl)-5-(trifluoromethyl)phenyl)-5-(pyridin-4-yl)furan-2-carboxamide N-(2-(4-(aminomethyl)-4-methylpiperidin-1-yl)-5-(trifluoromethyl)phenyl)-5-(tetrahydro-2H-pyran-4-yl)furan-2-carboxamide N-(2-(4-methyl-4-((methylamino)methyl)-piperidin-1-yl)-5-(trifluoromethyl)phenyl)-5-(tetrahydro-2H-pyran-4-yl)furan-2-carboxamide N-(2-(4-((dimethylamino)methyl)-4-methyl-piperidin-1-yl)-5-(trifluoromethyl)phenyl)-5-(tetrahydro-2H-pyran-4-yl)furan-2-carboxamide 1-(4-chloro-2-(5-(tetrahydro-2H-pyran-4-yl)furan-2-carboxamido)phenyl)-N,N,4-trimethyl-piperidine-4-carboxamide 1-(4-methoxy-2-(5-(tetrahydro-2H-pyran-4-yl)furan-2-carboxamido)phenyl)-N,N,4-trimethyl-piperidine-4-carboxamide 1-(4-cyclopropyl-2-(5-(tetrahydro-2H-pyran-4-yl)furan-2-carboxamido)phenyl)-N,N,4-trimethyl-piperidine-4-carboxamide N,N,4-trimethyl-1-(4-methyl-2-(5-(tetrahydro-2H-pyran-4-yl)furan-2-carboxamido)phenyl)piperidine-4-carboxamide N-(2-(4-methyl-4-(pyrrolidine-1-carbonyl)-piperidin-1-yl)-5-(trifluoromethyl)-phenyl)-5-(tetrahydro-2H-pyran-4-yl)furan-2-carboxamide N-(2-(4-methyl-4-(piperidine-1-carbonyl)-piperidin-1-yl)-5-(trifluoromethyl)phenyl)-5-(tetrahydro-2H-pyran-4-yl)furan-2-carboxamide N-(2-(4-methyl-4-(morpholine-4-carbonyl)-piperidin-1-yl)-5-(trifluoromethyl)phenyl)-5-(tetrahydro-2H-pyran-4-yl)furan-2-carboxamide N-(5-chloro-2-(4-((dimethylamino)methyl)-4-methylpiperidin-1-yl)phenyl)-5-(tetrahydro-2H-pyran-4-yl)furan-2-carb oxamide N-(2-(4-((dimethylamino)methyl)-4-methyl-piperidin-1-yl)-5-methoxyphenyl)-5-(tetrahydro-2H-pyran-4-yl)furan-2-carb oxamide N-(5-cyclopropyl-2-(4-((dimethylamino)methyl)-4-methylpiperidin-1-yl)phenyl)-5-(tetrahydro-2H-pyran-4-yl)furan-2-carboxamide N-(2-(4-((dimethylamino)methyl)-4-methyl-piperidin-1-yl)-5-methylphenyl)-5-(tetrahydro-2H-pyran-4-yl)furan-2-carboxamide N-(2-(4-methyl-4-(pyrrolidin-1-ylmethyl)piperidin-1-yl)-5-(trifluoromethyl)phenyl)-5-(tetrahydro-2H-pyran-4-yl)furan-2-carboxamide N-(2-(4-methyl-4-(piperidin-1-ylmethyl)piperidin-1-yl)-5-(trifluoromethyl)phenyl)-5-(tetrahydro-2H-pyran-4-yl)furan-2-carboxamide N-(2-(4-methyl-4-(morpholinomethyl)piperidin-1-yl)-5-(trifluoromethyl)phenyl)-5-(tetrahydro-2H-pyran-4-yl)furan-2-carboxamide N-(2-(8-azaspiro[4.5]decan-8-yl)-5-(trifluoromethyl)phenyl)-5-(tetrahydro-2H-pyran-4-yl)furan-2-carboxamide N-(2-(2-methyl-2,8-diazaspiro[4.5]decan-8-yl)-5-(trifluoromethyl)phenyl)-5-(tetrahydro-2H-pyran-4-yl)furan-2-carboxamide N-(2-(2-methyl-1-oxo-2,8-diazaspiro[4.5]decan-8-yl)-5-(trifluoromethyl)phenyl)-5-(tetrahydro-2H-pyran-4-yl)furan-2-carboxamide N-(2-(4-amino-4-methylpiperidin-1-yl)-5-(trifluoromethyl)-phenyl)-5-(tetrahydro-2H-pyran-4-yl)furan-2-carboxamide N-(2-(4-amino-4-methylpiperidin-1-yl)-5-(trifluoromethyl)phenyl)-5-(pyridin-4-yl)furan-2-carboxamide N-(2-(2-methyl-2,8-diazaspiro[4.5]decan-8-yl)-5-(trifluoromethyl)phenyl)-5-(pyridin-4-yl)furan-2-carboxamide N-(2-(2-methyl-1-oxo-2,8-diazaspiro[4.5]decan-8-yl)-5-(trifluoromethyl)phenyl)-5-(pyridin-4-yl)furan-2-carboxamide N-(2-(2-methyl-2,8-diazaspiro[4.5]decan-8-yl)-5-(chloro)phenyl)-5-(tetrahydro-2H-pyran-4-yl)furan-2-carboxamide N-(2-(2-methyl-1-oxo-2,8-diazaspiro[4.5]decan-8-yl)-5-(chloro)phenyl)-5-(tetrahydro-2H-pyran-4-yl)furan-2-carboxamide N-(2-(2-methyl-2,8-diazaspiro[4.5]decan-8-yl)-5-(methyl)phenyl)-5-(tetrahydro-2H-pyran-4-yl)furan-2-carboxamide N-(2-(2-methyl-1-oxo-2,8-diazaspiro[4.5]decan-8-yl)-5-(methyl)phenyl)-5-(tetrahydro-2H-pyran-4-yl)furan-2-carboxamide N-(2-(2-methyl-2,8-diazaspiro[4.5]decan-8-yl)-5-(cyclopropyl)phenyl)-5-(tetrahydro-2H-pyran-4-yl)furan-2-carboxamide N-(2-(2-methyl-1-oxo-2,8-diazaspiro[4.5]decan-8-yl)-5-(cyclopropyl)phenyl)-5-(tetrahydro-2H-pyran-4-yl)furan-2-carboxamide N-(2-(2-methyl-2,9-diazaspiro[5.5]undecan-9-yl)-5-(trifluoromethyl)phenyl)-5-(tetrahydro-2H-pyran-4-yl)furan-2-carboxamide N-(2-(2-methyl-2,9-diazaspiro[5.5]undecan-9-yl)-5-(trifluoromethyl)phenyl)-5-(tetrahydro-2H-pyran-4-yl)furan-2-carboxamide.

In the Definition of Formula (I) Herein

"$C_{1-6}$ alkyl group" refers to a linear or branched alkyl group comprising one to six carbon atoms, which is a monovalent group derived by removing an arbitrary hydrogen atom from an aliphatic hydrocarbon consisting of one to six carbons. Specifically, the $C_{1-6}$ alkyl group includes, for example, a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group;

Herein, the phrase "may have one or more substituent" means that a certain group or compound may optionally have an arbitrary selection or combination of one or more substituent at substitutable positions. Specifically, the substituents can include, for example, atoms or groups selected from one or more of: halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-6}$ alkoxy (for example, methoxy), $C_{1-6}$ thioalkyl (for example thiomethyl), $C_{2-6}$ alkenyl, $C_{2-6}$ alkynyl; $C_{1-6}$ alkoxycarbonyl, $C_{1-6}$ alkylsulfonyl, $C_{5-10}$ cycloalkyl, $C_{5-10}$ heterocycloalkyl, $C_{5-10}$ aryl, benzyl, heteroaryl, phenyl, or $C_{5-10}$ cycloalkyl, $C_{5-10}$ heterocycloalkyl, $C_{5-10}$ aryl or benzyl or phenyl or heteroaryl substituted by one or more of halogen, hydroxyl, hydroxymethyl, hydroxyethyl, mercapto, nitro, cyano, formyl, carboxyl, trifluoromethyl, trifluoromethoxy, amino, oxo, imino, $C_{1-6}$ alkyl (for example methyl), $C_{1-6}$ thioalkyl (for example thiomethyl), $C_{2-6}$ alkenyl, $C_{2-6}$ alkynyl; $C_{1-6}$ alkoxycarbonyl, $C_{1-6}$ alkylsulfonyl, or $C_{1-6}$ alkoxy (for example, methoxy).

"$C_{2-6}$ alkenyl group" refers to a linear or branched alkenyl group comprising two to six carbons. Specifically, the $C_{2-6}$ alkenyl group includes, for example, a vinyl group, an allyl group, a 1-propenyl group, a 2-propenyl group, a 1-butenyl group, a 2-butenyl group, a 3-butenyl group, a pentenyl group, and a hexenyl group;

"$C_{2-6}$ alkynyl group" refers to a linear or branched alkynyl group comprising two to six carbons. Specifically, the $C_{2-6}$ alkynyl group includes, for example, an ethynyl group, a 1-propynyl group, a 2-propynyl group, a butynyl group, a pentynyl group, and a hexynyl group.

"$C_{1-6}$ alkoxy group" refers to an oxy group to which the above-defined "$C_{1-6}$ alkyl group" is linked. Specifically, the $C_{1-6}$ alkoxy group includes, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group;

"$C_{1-6}$ alkylthio group" refers to a thio group to which the above-defined "$C_{1-6}$ alkyl group" is linked. Specifically, the "$C_{1-6}$ alkylthio group" includes, for example, a methylthio group, an ethylthio group, a 1-propylthio group, a 2-propylthio group, a butylthio group, and a pentylthio group;

"$C_{1-6}$ alkoxycarbonyl group" refers to a carbonyl group to which the above-defined "$C_{1-6}$ alkoxy group" is linked. Specifically, the $C_{1-6}$ alkoxycarbonyl group includes, for example, a methoxy carbonyl group, an ethoxy carbonyl group, a 1-propyloxycarbonyl group, and a 2-propyloxycarbonyl group;

"$C_{1-6}$ alkylsulfonyl group" refers to a sulfonyl group to which the above-defined "$C_{1-6}$ alkyl group" is linked. Specifically, the $C_{1-6}$ alkylsulfonyl group includes, for example, a methylsulfonyl group, an ethylsulfonyl group, a 1-propylsulfonyl group, and a 2-propylsulfonyl group;

"heterocycle" or "heterocyclic group" refers to an aromatic or non-aromatic ring that may comprise double bonds within the ring, wherein at least one, for example one or two, of the atoms constituting the ring are heteroatoms;

"heteroatom" refers to a sulfur atom, an oxygen atom, or a nitrogen atom.

DETAILED DESCRIPTION OF THE INVENTION

The compounds of the present invention are SRPK1-specific inhibitors and may therefore be used in methods of treating or preventing any disease or condition in which SRPK1 is implicated. Such conditions and treatments are described below. The compounds also do not inhibit any of CYP1A2, CYP2C9, CYP2C129, CYP2D6 or CYP3A4 to any clinically significant extent and so are particularly suited for systemic administration for the treatment or prevention of any of the diseases or conditions mentioned.

Anti-Angiogenic Treatment

The compounds of the present invention may be used in anti-angiogenic treatments. The anti-angiogenic treatment preferably includes the treatment or prevention of any disease or disorder associated with abnormal angiogenesis or abnormal over-production of pro-angiogenic VEGF isoforms ($VEGF_{xxx}$). Such diseases and disorders include, for example, vascular disease (e.g. vasoconstriction and disorders characterised by vasoconstriction, and cardiovascular disease), malignant and benign neoplasia (e.g. angiogenesis-dependent cancers, for example tumorous cancers), tumor metastasis, inflammatory disorders, diabetes, diabetic retinopathy and other complications of diabetes (e.g. diabetic neovascularisation or diabetic macular oedema), trachoma, retrolental hyperplasia, neovascular glaucoma, age-related macular degeneration, macular oedema, haemangioma, immune rejection of implanted corneal tissue, corneal angiogenesis associated with ocular injury or infection, Osler-Webber Syndrome, myocardial angiogenesis, wound granulation, telangiectasia, hemophiliac joints, angiofibroma, telangiectasia psoriasis scleroderma, pyogenic granuloma, rubeosis, obesity, arthritis (e.g. rheumatoid arthritis), hematopoieses, vasculogenesis, gingivitis, atherosclerosis, endometriosis, neointimal hyperplasia, psoriasis, hirsutism and proliferative retinopathy. The anti-angiogenic treatment according to the present invention may also include non-therapeutic treatments performed on healthy subjects, for example to inhibit vascular development for cosmetic purposes. For further details on diseases and disorders associated with abnormal angiogenesis, and on anti-angiogenic treatments, see WO 2008/110777, the contents of which are incorporated herein by reference.

In particular, the compounds of the present invention may be used in the treatment or prevention of ocular neovascularisation, which may include retinal neovascularisation or choroidal neovascularisation, for example age-related macular degeneration or macular oedema. In addition, the compounds of the present invention may be used in the treatment or prevention of malignant neoplasias or cancers, for example prostate cancer and breast cancer.

Microvascular Hyperpermeability Disorders, Disorders of Epithelial Cell Survival and Disorders of Fenestrations of Epithelial Filtration Membranes The compounds of the present invention, as SRPK1 inhibitors, may also be used as therapeutic agents in treating other disorders in which the alternatively spliced $VEGF_{xxx}b$ isoform has been implicated. For example, it has been shown in WO 2010/058227, the contents of which are incorporated herein by reference, that $VEGF_{xxx}b$ is active against a range of microvascular hyperpermeability disorders, disorders of epithelial cell survival and disorders of fenestrations of epithelial filtration membranes.

Microvascular hyperpermeability, disorders of regulation of the pro-angiogenic pro-permeability properties of $VEGF_{xxx}$ isoforms, disorders of epithelial cell survival and permeability, and/or disorders in the nature (for example the number density and/or size) of fenestrations changes of epithelial filtration membranes and/or regulating endothelial glycocalyx (eg thickness, charge, chemical constituents—produced in situ or adsorbed from plasma) underlie a number of serious medical conditions and hyperpermeability states.

Examples of such conditions include, for example, proteinuria, uraemia, microalbuminuria, hypoalbuminemia, renal hyperfiltration, nephrotic syndrome, renal failure, pulmonary hypertension, capillary hyperpermeability, microaneurysms, cerebral oedema and vascular complications of diabetes.

Examples of such vascular complications of diabetes include, for example, diabetic retinopathy, both proliferative and non-proliferative, and diabetic nephropathy. Vascular complications of diabetes can be associated with either Type I or Type II diabetes.

The loss of proteins from the blood can lead to further complications, for example thromboses, especially thromboses in the brain, and susceptibility to infections. Loss of natural proteins from the blood can seriously impair the efficacy of cancer therapies.

The microvascular hyperpermeability disorder may particularly be a renal disorder, for example a permeability disorder of the GFB, for example a permeability disorder of the podocytes.

Examples of disorders where treatment to support epithelial cell survival would be effective are as follows:

systemic capillary molecular leak associated with septicaemia in critical multi-organ disease and renal disease, acute pulmonary fibrotic disease, adult respiratory distress syndrome, adult respiratory distress syndrome, advanced cancer, allergic respiratory disease, alveolar injury, angiogenesis, arthritis, ascites, asthma, asthma or edema following burns, atherosclerosis, autoimmune diseases, bone resorption, bullous disorder associated with subepidermal blister formation including bullous pemphigoid, cardiovascular condition, certain kidney diseases associated with proliferation of glomerular or mesangial cells, chronic and allergic inflammation, chronic lung disease, chronic occlusive pulmonary disease, cirrhosis, corneal angiogenesis, corneal disease, coronary and cerebral collateral vascularization, coronary restenosis, damage following heart disease, dermatitis herpetiformis, diabetes, diabetic nephropathy, diabetic retinopathy, endotoxic shock, erythema multiforme, fibrosis, glomerular nephritis, glomerulonephritis, graft rejection, gram negative sepsis, hemangioma, hepatic cirrhosis, hepatic failure, Herpes Zoster, host-versus-graft reaction (ischemia reperfusion injury and allograft rejections of kidney, liver, heart, and skin), impaired wound healing in infection, infection by Herpes simplex, infection from human immunodeficiency virus (HIV), inflammation, cancer, inflammatory bowel disease (Crohn's disease and ulcerative colitis), inflammatory conditions, in-stent restenosis, in-stent stenosis, ischemia, ischemic retinal-vein occlusion, ischemic retinopathy, Kaposi's sarcoma, keloid, liver disease during acute inflammation, lung allograft rejection (obliterative bronchitis), lymphoid malignancy, macular degeneration retinopathy of prematurity, myelodysplastic syndromes, myocardial angiogenesis, neovascular glaucoma, non-insulin-dependent diabetes mellitus (NIDDM), obliterative bronchiolitis, ocular conditions or diseases, ocular diseases associated with retinal vessel proliferation, Osier-Weber-Rendu disease, osteoarthritis, ovarian hyperstimulation syndrome, Paget's disease, pancreatitis, pemphigoid, polycystic kidney disease, polyps, postmenopausal osteoperosis, preeclampsia, psoriasis, pulmonary edema, pulmonary fibrosis, pulmonary sarcoidosis, restenosis, restenosis, retinopathy including diabetic retinopathy, retinopathy of prematurity and age related macular degeneration; rheumatoid arthritis, rheumatoid arthritis, rubeosis, sarcoidosis, sepsis, stroke, synovitis, systemic lupus erythematosus, throiditis, thrombic micoangiopathy syndromes, transplant rejection, trauma, tumor-associated angiogenesis, vascular graft restenosis, vascular graft restenosis, von Hippel Lindau disease, wound healing.

The present invention may be used in the treatment of macular dystrophy. This includes: Stargardt disease/fundus flavimaculatus; Stargardt-like macular dystrophy; Stargardt-like macular dystrophy; Autosomal dominant "bull'seye" macular dystrophy Best macular dystrophy; Adult vitelliform dystrophy; Pattern dystrophy; Doyne honeycomb retinal dystrophy; North Carolina macular dystrophy; Autosomal dominant macular dystrophy resembling MCDR1; North Carolina-like macular dystrophy associated with deafness; Progressive bifocal chorioretinal atrophy; Sorsby's fundus dystrophy; Central areolar choroidal dystrophy; Dominant cystoid macular dystrophy; Juvenile retinoschisis; Occult Macular Dystrophy; Non-familial Occult Macular Dystrophy.

The disorder may particularly be a disorder of the retinal epithelium, such as geographic atrophy, or age related macular degeneration.

For further details on of microvascular hyperpermeability disorders, disorders of epithelial cell survival and disorders of fenestrations of epithelial filtration membranes, and the treatment thereof, see WO 2010/058227, the contents of which are incorporated herein by reference.

Neuropathic and Neurodegenerative Disorders

The compounds of the present invention, as SRPK1 inhibitors, may also be used as therapeutic agents in treating other disorders in which the alternatively spliced $VEGF_{xxx}b$ isoform has been implicated. For example, it has been shown in WO 2009/106855, the contents of which are incorporated herein by reference, that $VEGF_{xxx}b$ has neuroprotective and neuroregenerative effects.

Neuropathic disorders to be treated or prevented according to the present invention include neuropathic pain and diabetic and other neuropathies.

Neurodegenerative disorders to be treated or prevented according to the present invention include neurodegeneration of the cognitive and non-cognitive types, neuromuscular degeneration, motor-sensory neurodegeneration, ocular neurodegeneration.

The activities of the proteins of the $VEGF_{xxx}b$ family are predicted to both actively prevent and actively reverse the conditions and disorders.

Furthermore, since mild cognitive dysfunction is often associated with the normal state in certain classes of healthy people, for example the aged, persons under stress, tired or exhausted persons, the present invention is also applicable to non-therapeutic treatments of healthy people to adjust or normalise their cognitive function and behaviour, including thinking, memory, learning, concentration and reasoning.

Still further, since neuroregeneration can assist in normalising brain neural networks in subjects having psychiatric or behavioural abnormalities, whether or not these are diagnosable as one or more recognised psychiatric condition, the present invention is also applicable to therapeutic treatment of persons having psychiatric disorders and to non-therapeutic treatment of physically healthy people to adjust their cognition and behaviour towards the normal state.

For example, the present invention provides for the treatment or prevention of: pain (for example, neuropathic pain), dementia, age-related cognitive impairment, Alzheimer's disease, senile dementia of the Alzheimer's type (SDAT), Lewy body dementia, vascular dementia, Parkinson's disease, postencephalitic Parkinsonism, depression, schizophrenia, muscular dystrophy including facioscapulohumeral muscular dystrophy (FSH), Duchenne muscular dystrophy, Becker muscular dystrophy and Bruce's muscular dystrophy, Fuchs' dystrophy, myotonic dystrophy, corneal dystrophy, reflex sympathetic dystrophy syndrome (RSDSA), neurovascular dystrophy, myasthenia gravis, Lambert Eaton disease, Huntington's disease, motor neurone diseases including amyotrophic lateral sclerosis (ALS), multiple sclerosis, postural hypotension, traumatic neuropathy or neurodegeneration e.g. following stroke or following an accident (for example, traumatic head injury or spinal cord injury), Batten's disease, Cockayne syndrome, Down syndrome, corticobasal ganglionic degeneration, multiple system atrophy, cerebral atrophy, olivopontocerebellar atrophy, dentatorubral atrophy, pallidoluysian atrophy, spinobulbar atrophy, optic neuritis, sclerosing pan-encephalitis (SSPE), attention deficit disorder, post-viral encephalitis, post-poliomyelitis syndrome, Fahr's syndrome, Joubert syndrome, Guillain-Barre syndrome, lissencephaly, Moyamoya disease, neuronal migration disorders, autistic syndrome, polyglutamine disease, Niemann-Pick disease, progressive multifocal leukoencephalopathy, pseudotumor cerebri, Refsum disease, Zellweger syndrome, supranuclear palsy, Friedreich's ataxia, spinocerebellar ataxia type 2, Rhett syndrome, Shy-Drager syndrome, tuberous sclerosis, Pick's disease, chronic fatigue syndrome, neuropathies including hereditary neuropathy, diabetic neuropathy and mitotic neuropathy, prion-based neurodegeneration, including Creutzfeldt-Jakob disease (CJD), variant CJD, new variant CJD, bovine spongiform encephalopathy (BSE), GSS, FFI, kuru and Alper's syndrome, Joseph's disease, acute disseminated encephalomyelitis, arachnoiditis, vascular lesions of the central nervous system, loss of extremity neuronal function, Charcot- Marie-Tooth disease, Krabbe's disease, leukodystrophies, susceptibility to heart failure, asthma, epilepsy, auditory neurodegeneration, macular degeneration, pigmentary retinitis and glaucoma-induced optic nerve degeneration.

Generally speaking, mental disorders are not diagnosed as "psychiatric disorders" unless the associated behaviours or thoughts cause significant distress to the individual or are disruptive of his or her everyday functioning. There is therefore a borderline between diagnosable disorders and similar, but less severe or disruptive, psychological functions the treatment of which should be considered as non-therapeutic (see below).

Examples of psychiatric disorders with which the present invention is concerned include, without limitation: anxiety disorders (for example, acute stress disorder, panic disorder, agoraphobia, social phobia, specific phobia, obsessive-compulsive disorder, sexual anxiety disorders, post-traumatic stress disorder, body dysmorphic disorder and generalized anxiety disorder), childhood disorders (for example, attention-deficit hyperactivity disorder (ADHD), Asperger's disorder, autistic disorder, conduct disorder, oppositional defiant disorder, separation anxiety disorder and Tourette's disorder), eating disorders (for example, anorexia nervosa and bulimia nervosa), mood disorders (for example, depression, major depressive disorder, bipolar disorder (manic depression), seasonal affective disorder (SAD), cyclothymic disorder and dysthymic disorder), sleeping disorders, cognitive psychiatric disorders (for example, delirium, amnestic disorders), personality disorders (for example, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder and obsessive-compulsive personality disorder), psychotic disorders (for example, schizophrenia, delusional disorder, brief psychotic disorder, schizophreniform disorder, schizoaffective disorder and shared psychotic disorder), and substance-related disorders (for example, alcohol dependence, amphetamine dependence, cannabis dependence, cocaine dependence, hallucinogen dependence, inhalant dependence, nicotine dependence, opioid dependence, phencyclidine dependence and sedative dependence).

For further details on neuropathic and neurodegenerative disorders, and the treatment thereof, see WO 2009/106855, the contents of which are incorporated herein by reference.

Treatment of Pain

The compounds of the present invention, as SRPK1 inhibitors, may also be used as therapeutic agents in treating other disorders in which the alternatively spliced $VEGF_{xxx}b$ isoform has been implicated. The compounds of the present invention, as SRPK1 inhibitors, may be used to alleviate pain, for example in a subject experiencing pain as a result of nerve injury or other neuronal abnormality. The compounds of the present invention, as SRPK1 inhibitors, may also be used to alleviate pain in a subject experiencing pain without nerve injury or other neuronal abnormality. The compounds of the present invention, as SRPK1 inhibitors, may be used to alleviate inflammatory or non-inflammatory pain in a subject experiencing pain. For example, it has been shown in WO 2011/148200, the contents of which are incorporated herein by reference, that $VEGF_{xxx}b$ has an analgesic effect on VEGFR2-mediated non-inflammatory pain in mammals.

VEGFR2-mediated non-inflammatory pain to be treated or prevented according to the present invention includes non-inflammatory neuropathic and nociceptive pain where the VEGFR2 receptor is involved in the cause or transmission of the pain. For example, the compounds according to the present invention are predicted to have activity against non-inflammatory allodynia and pain (antiallodynic and analgesic activity).

Pain states of this type include chronic pain, whether of the intermittent or constant form. Such pain states may include, for example, low back pain, neuralgia, atypical pains such as atypical facial pain, pain exhibited post-surgery, post-injury (for example, after surgery or injury causing nerve damage) or in association with cancer or with cancer therapy such as cytotoxic or radiation therapy, or neuropathy associated with diabetes (diabetic neuropathy, insulin neuritis) or other systemic or autoimmune disease or pathology, or the treatment thereof, alcoholism or HIV infection, ageing associated neuropathy, or neuropathy of unknown origin.

The activities of the proteins of the VEGFR2 agonists, for example the $VEGF_{xxx}b$ family, are predicted to both actively prevent and actively reverse VEGFR2-mediated non-inflammatory pain. However, in view of the anti-angiogenic activity of the proteins of the $VEGF_{xxx}b$ family, use of the compounds of the present invention will be restricted to pain in contexts where possible inhibition of angiogenesis would not be detrimental to the patient.

The compounds used in the present invention may be employed in association with one or more different pain treatment agent for the purpose of normalising the sensitivity towards pain of the subject treated (or being co-treated) with the said one or more different pain treatment agent. The term "normalising" means moving the subject's pain sensitivity towards normal levels, and may include enhancement of the sensitivity if the one or more different pain treatment agent causes an excessive reduction in feeling or in sensitivity towards pain.

The one or more different pain treatment agent may be selected from pain treatment agents currently known or yet to be devised. Such selection will be well within the skill of the person of ordinary skill in this art. Such combination treatments can enable fine control of pain sensitivity in subjects and minimisation of overall side effects according to the particular condition and needs of the subject.

For further details on pain, and the treatment thereof, see WO 2011/148200, the contents of which are incorporated herein by reference.

Reduction of Risk of Pre-Eclampsia

The compounds of the present invention, as SRPK1 inhibitors, may also be used as therapeutic agents in treating other disorders in which the alternatively spliced $VEGF_{xxx}b$ isoform has been implicated. For example, it has been shown in WO 2011/036429, the contents of which are incorporated herein by reference, that reduced $VEGF_{xxx}b$ levels in pregnant female mammals increase the risk of the female mammal developing pre-eclampsia.

Thus, compounds of the present invention may be used to increase $VEGF_{xxx}b$ levels in a pregnant female mammal so as to reduce the risk of pre-eclampsia the female mammal developing pre-eclampsia or a complication linked thereto, or of a fetus of the female mammal developing a fetal or neonatal deficiency linked to maternal pre-eclampsia.

Pre-eclampsia in humans can develop as early as 20 weeks of gestation. Pre-eclampsia that develops before about 34 weeks of gestation is normally referred to as "early pre-eclampsia" or "early-onset pre-eclampsia". Pre-eclampsia that develops after about 34 weeks of gestation is normally referred to as "late pre-eclampsia" or "late-onset pre-eclampsia". In addition, pre-eclampsia can be categorised as "severe pre-eclampsia" according to criteria established by the United Kingdom Royal College of Obstetricians and Gynaecologists. Under these criteria, a patient with "severe pre-eclampsia" will have systolic blood pressure (BP) greater than 169 mmHg or diastolic BP greater than 109 mmHg with proteinuria greater than 1 g/24 h; or will show occurrence of HELLP syndrome (haemolysis, elevated liver enzymes and low platelet count).

For further details on pre-eclampsia, and methods to reduce the risk of a pregnant female mammal developing developing pre-eclampsia or a complication linked thereto, or of a fetus of the female mammal developing a fetal or neonatal deficiency linked to maternal pre-eclampsia, see WO 2011/036429, the contest of which are incorporated herein by reference.

Active Compounds

Compounds of the present invention are as defined by Formula (I) and have been shown to be inhibitors of the kinase SRPK1, and are thus useful in treatments as described herein. The compounds of the present invention may be synthesised by any known method. An exemplary synthesis is described below in the Examples.

Co-Administration

The compounds of the present invention may, if desired, be co-administered with one or more additional active agent, for example one or more agent selected from, but not limited to, cholinesterase inhibitors, dopamine agonists (e.g. L-dopa), COMT inhibitors, MAO-B inhibitors, anti-cholinergics, acetylcholine agonists, serotonin agonists, AMPA receptor agonists, GABA receptor agonists, NMDA receptor agonists, β-adrenoceptor agonists, digoxin, dobutamine, anti-inflammatories, neurotrophic factors, statins, adenosine A2a receptor antagonists, aldose reductase inhibitors, immunomodulators, cannabinoid agonists, interferon or tricyclic anti-depressants.

Salts, Solvates, Hydrates and Prodrugs

As used herein, the term "salt" is not particularly limited, so long as it is a pharmaceutically acceptable salt which is formed with a compound according to the present invention. Such salts include, for example, inorganic acid salts, organic salts, inorganic base salts, organic base salts, and acidic or basic amino acid salts.

Examples of preferable inorganic acid salts include hydrochloride, hydrobromate, sulfate, nitrate, and phosphate. Examples of preferable organic salts include acetate, succinate, fumarate, maleate, tartrate, citrate, lactate, stearate, benzoate, methanesulfonate, and p-toluene sulfonate. Examples of preferable inorganic base salts include alkali metal salts, such as sodium salts and potassium salts; alkali earth metal salts, such as calcium salts and magnesium salts; aluminium salts; and ammonium salts. Examples of preferable organic base salts include diethylamine salts, diethanol amine salts, meglumine salts, and N,N'-dibenzylethylenediamine salts. Examples of preferable acidic amino acid salts include: aspartate and glutamate. Examples of preferable basic amino acid salts include: arginine salts, lysine salts, and ornithine salts.

When left in air, the compounds of the present invention sometimes absorb moisture, and are sometimes attached to absorbed water or converted to hydrates. Such hydrates are also included in the present invention.

Furthermore, compounds of the present invention are sometimes converted into solvates, absorbing some other solvents. Such solvates are also included in the present invention.

Any organic solvent may in principle be used to prepare a solvate of the compounds of the present invention. A solvate can include also water together with the one or more organic solvent. Thus, for example, the solvent may be selected from ketones, alcohols, ethers, esters, aromatic solvents, and, where possible, mixtures thereof with each other, with other organic solvents and/or with water.

Pharmaceutically acceptable prodrug forms of the compounds of formula (I) may be used in the present invention. "Pharmaceutically acceptable prodrugs" means those prodrugs of the compounds which are, within the scope of sound medical and vetinary judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group. Because of the ease with which the metabolically cleavable groups of the compounds are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396,1985; A Textbook of Drug Design and Development, Krogsgaard-Larsen and H. Bundgaard, ed., Chapter 5; Design and Applications of Prodrugs p. 113-191, 1991; Advanced Drug Delivery Reviews, H. Bundgard, 8, p. 1-38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A. C. S. Symposium Series, and Bioreversible Carriers in Drug Design, Edward B. Roche, ed., American Pharmaceutical Association and Pergamon Press, 1987, which are incorporated herein by reference.

Compositions and Administration

The compound according to the present invention may be administered in the form of a composition comprising the active agent and any suitable additional component. The composition may, for example, be a pharmaceutical composition (medicament), suitably for topical administration (e.g. as eyedrops or cream or lotion), or systemic administration such as enteral administration (e.g. in tablet, lozenge, dragee, capsule or liquid form) or parenteral administration (e.g. injection, implantation or infusion). The composition may alternatively, for example, be a foodstuff, food supplement, beverage or beverage supplement.

The term "pharmaceutical composition" or "medicament" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations. Techniques and formulations generally may be found in Remington, The Science and Practice of Pharmacy, Mack Publishing Co., Easton, PA, latest edition.

Liquid form preparations include solutions, suspensions, and emulsions. As an example may be mentioned water or water-propylene glycol solutions for parenteral injection or topical administration. Liquid preparations can also be formulated in solution in aqueous polyethylene glycol solution.

Also included are solid form preparations which are intended to be converted, shortly before use, to liquid form preparations for either topical, oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for topical or parenteral use.

The composition may be in a formulation intended for topical application. The formulation may be a gelling formulation to control release and therefore availability of the active agent following topical application. The formulation may contain one or more gelling agents, for example hydroxypropyl methylcellulose. The formulation may contain one or more surfactants, for example a non-ionic liquid polymer, examples of which include Tyloxapol, and the Pluronics® poloxamers from BASF. The formulation may contain one or more solubilizers, for example dextrose or sorbitol. The formulation may contain one or more antimicrobial or antiseptic agents, for example benzalkonium chloride. The aforementioned named gelling agents, surfactants, solubilizers and antimicrobial agents are listed purely by way of example and it will be appreciated that other agents to perform these functions are known.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The dosage regime for administration of the active agent may, for example, comprise a total dose of up to 1 µg, for example up to 500 ng, for example up to 50 ng, for example less than 20 ng of active agent in a dosing period ranging, for example, between 1 and 14 days. For example, a total dose of less than 18 ng, 17 ng, 16 ng, 15, ng, 14 ng, 13 ng, 12 ng, 11 ng or 10 ng may be administered.

The compound of Formula (I) or a pharmaceutically acceptable salt, solvate, hydrate or prodrug thereof may be administered in a therapeutically effective amount. A therapeutically effective amount of a compound of Formula (I) for topical administration for treatment of CNV may be at least about 5 µg/10 µl of delivery vehicle. Alternatively, a therapeutically effective amount may be at least about 100 µg/mL, for example at least about 200 µg/mL, at least about 300 µg/mL, at least about 400 µg/mL, at least about 500 µg/mL, at least about 600 µg/mL, at least about 700 µg/mL, at least about 800 µg/mL, at least about 900 µg/mL, or at least about 1000 µg/mL, Alternatively, a therapeutically effective amount may be at least about 1 mg/mL, for example at least about 2 mg/mL, at least about 3 mg/mL, at least about 4 mg/mL, at least about 5 mg/mL. Alternatively, a therapeutically effective amount may be less than about 5 mg/mL, for example less than about 4 mg/mL, less than about 3 mg/mL, less than about 2 mg/mL, less than about 1 mg/mL. The therapeutically effective amount may be administered daily, for a dosing period ranging, for example, between 1 and 14 days. The therapeutically effective amount may be a total daily dosage which may be divided and administered in portions during the day, for example twice daily.

A therapeutically effective amount of a compound of Formula (I) for anti-angiogenic treatment of a mammalian subject, or for use in treating or preventing microvascular hyperpermeability disorders, or in regulating the pro-angiogenic pro-permeability properties of $VEGF_{xxx}$ isoforms, or in supporting epithelial cell survival without increased permeability, or in reducing the nature (for example the number density and/or size) of fenestrations of epithelial filtration membranes, or for use in treating or preventing neuropathic and neurodegenerative disorders, or for use as a neuroprotective or neuroregenerative agent in vivo or in vitro, or for use in treating or preventing VEGFR2-mediated non-inflammatory pain, or for use in reducing the risk of a female mammal developing pre-eclampsia or a complication linked thereto, or of a fetus of the female mammal developing a fetal or neonatal deficiency linked to maternal pre-eclampsia may be calculated according to body mass of the subject to be treated, and may be at least about 20 mg/kg, for example at least about 30 mg/kg, at least about 40 mg/kg, at least about 50 mg/kg, at least about 60 mg/kg, at least about 70 mg/kg, at least about 80 mg/kg, at least about 90 mg/kg, at least about 100 mg/kg. Alternatively, the therapeutically effective amount may be less than about 100 mg/kg, for example less than about 90 mg/kg, less than about 80 mg/kg, less than about 70 mg/kg, less than about 60 mg/kg, less than about 50 mg/kg, less than about 40 mg/kg, less than about 30 mg/kg, or less than about 20 mg/kg, for example less than about 10 mg/kg, less than about 5 mg/kg.

"Treating or Preventing"

The expression "treating or preventing" and analogous terms used herein refers to all forms of healthcare intended to remove or avoid the disorder or to relieve its symptoms, including preventive, curative and palliative care, as judged according to any of the tests available according to the prevailing medical and psychiatric practice. An intervention that aims with reasonable expectation to achieve a particular result but does not always do so is included within the expression "treating or preventing". An intervention that succeeds in slowing or halting progression of a disorder is included within the expression "treating or preventing".

Certain neurological and psychiatric disorders are considered as "spectrum" conditions, in which individuals may exhibit some or all of a range of possible symptoms, or may exhibit only a mild form of the disorder. Furthermore, many neurological and psychiatric conditions are progressive, starting with relatively mildly abnormal symptoms and progressing to more severely abnormal symptoms. The present invention includes the treatment and prevention of all neurological and psychiatric conditions of whatever type and stage.

"Susceptible To"

The expression "susceptible to" and analogous terms used herein refers particularly to individuals at a higher than normal risk of developing a medical or psychiatric disorder, or a personality change, as assessed using the known risk factors for the individual or disorder. Such individuals may, for example, be categorised as having a substantial risk of developing one or more particular disorders or personality changes, to the extent that medication would be prescribed and/or special dietary, lifestyle or similar recommendations would be made to that individual.

"Non-Therapeutic Method"

The expression "non-therapeutic method" used herein refers particularly to an intervention performed on an individual who is neurologically or psychologically within the normal range, to normalise or enhance or improve a function of the neurological or psychological kind.

A neurological function that may suitably be treated non-therapeutically may include, for example, cognition (including thinking, reasoning, memory, recall, imagining and learning), concentration and attention, particularly towards the milder end of the scale of conditions, and mild abnormal behavioural or personality traits. A psychological function that may suitably be treated non-therapeutically may include, for example, human behaviour, mood, personality and social function, for example grief, anxiety, depression, moodiness, moroseness, teenage moods, disrupted sleep patterns, vivid dreaming, nightmares, and sleepwalking.

There is a borderline between diagnosable neurological and psychiatric disorders and (non-diagnosable) neurological and psychological functions within the normal range. Therefore, in addition to the examples of neurological and psychological functions given above that are treatable according to the non-therapeutic methods of the present invention, mild forms of neurological and psychiatric disorders, that are non-diagnosable because the associated behaviours or thoughts do not cause significant distress to the individual or are not disruptive of his or her everyday functioning, are also to be considered as conditions treatable non-therapeutically according to the present invention.

"Normalise"

The expression "normalise" and analogous terms used herein refers particularly to a physiological adjustment towards a condition characteristic of general normal neurological or psychiatric health, whether or not a condition is actually reached that would be characterised as normal.

Mammals

Besides being useful for human treatment, the present invention is also useful in a range of mammals. Such mammals include non-human primates (e.g. apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g. rabbits, rats, mice, hamsters, gerbils or guinea pigs). Where the disorder or function to be treated is exclusive to humans, then it will be understood that the mammal to be treated is a human. The same applies respectively to any other mammalian species if the disorder or function to be treated is exclusive to that species.

BRIEF DESCRIPTION OF THE DRAWINGS

Embodiments of the present invention will now be described, purely by way of example, and with reference to the accompanying Figures, in which:

FIGS. 1(a) and (b) show the effect of a compound of the invention on lesion size in a laser-induced mouse model of CNV.

METHODS

Synthetic Protocols

General synthetic protocols for compounds are shown in Schemes 1-3, and described in detail below, in which the substituents are as defined herein. Variations of this protocol to synthesize other compounds described herein are within the wherewithal of the skilled person.

Scheme 1
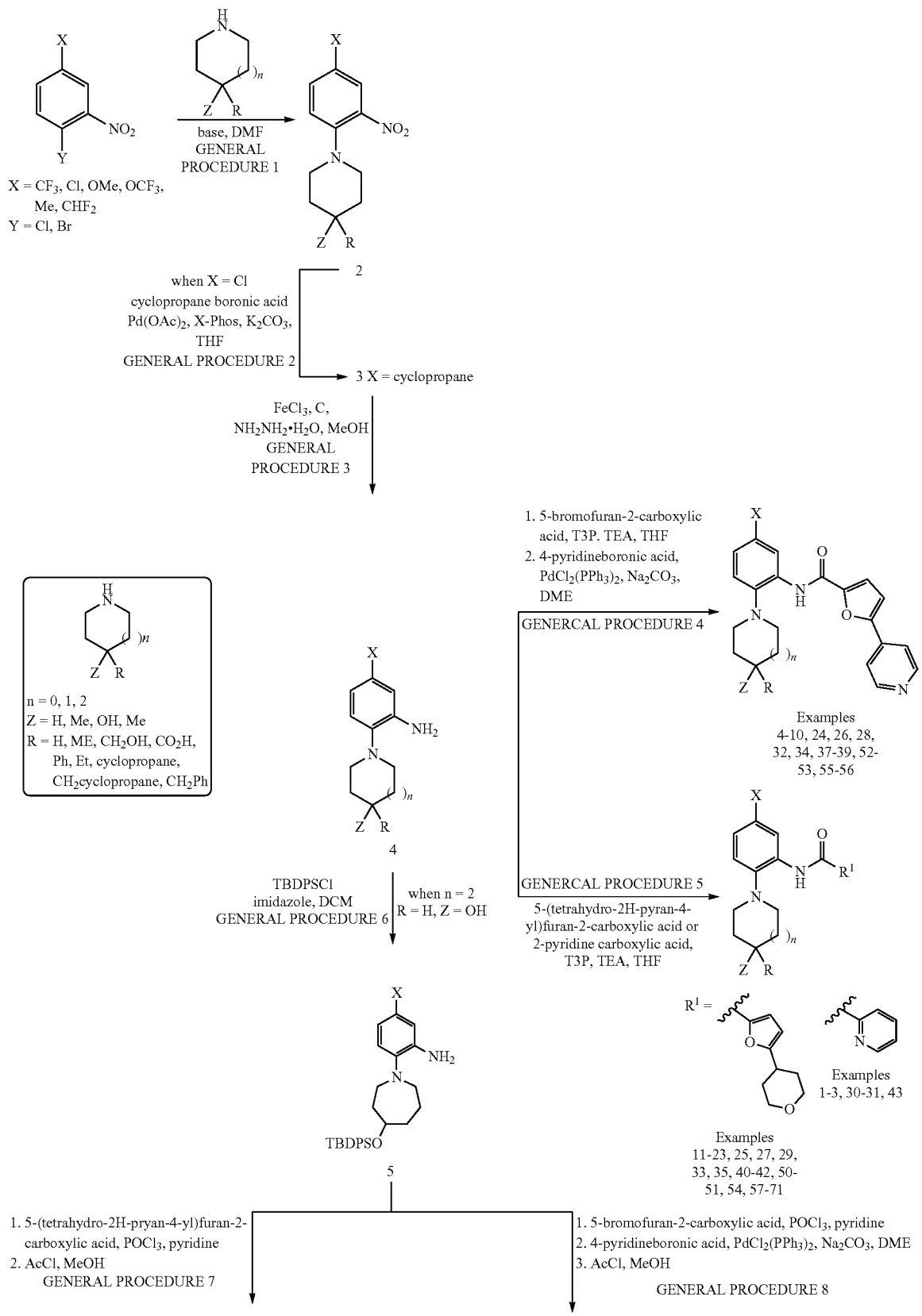

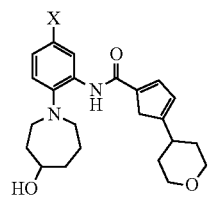
Examples 47-49
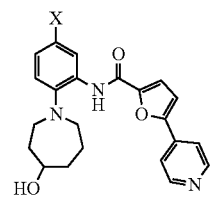
Examples 44-46
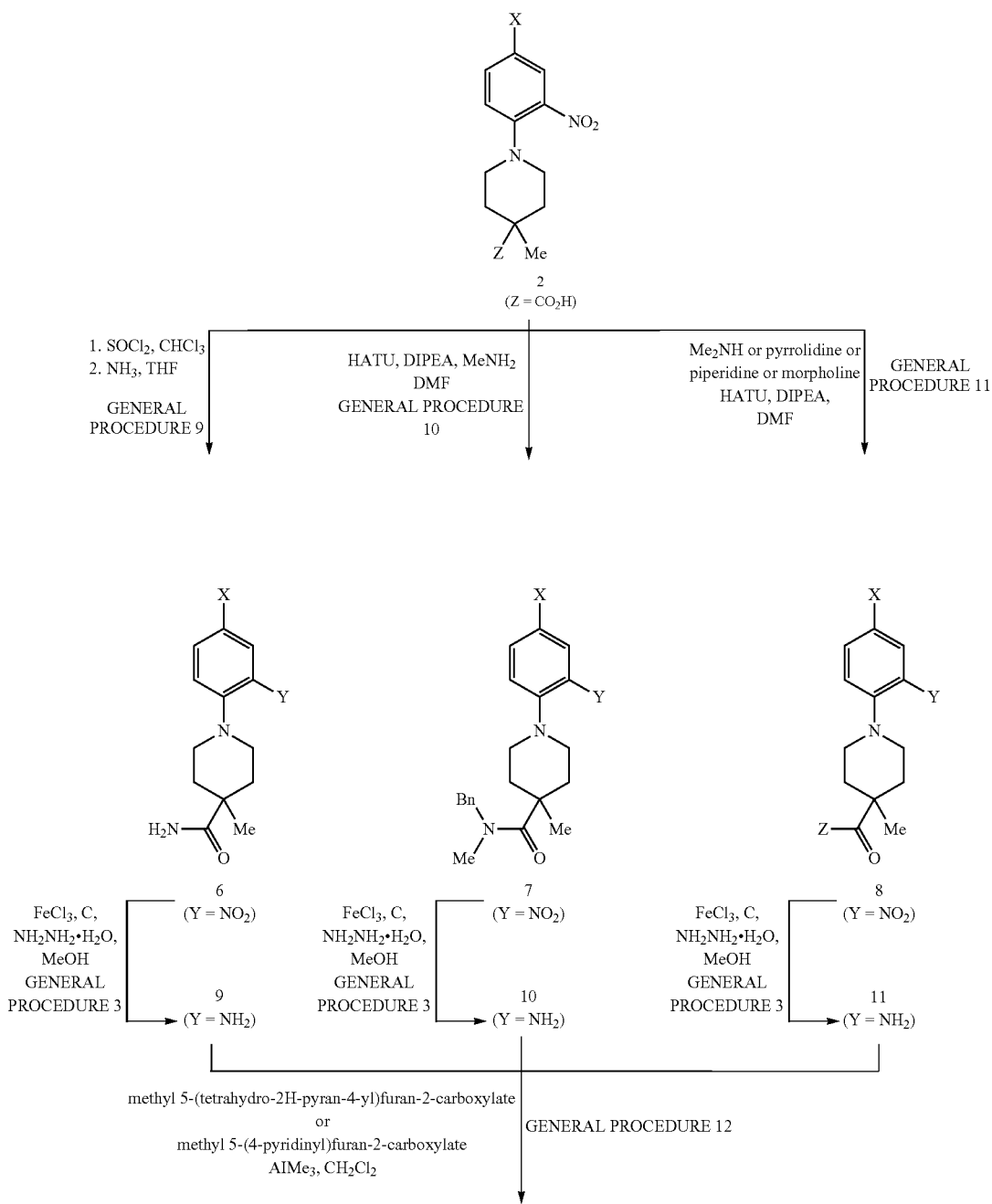

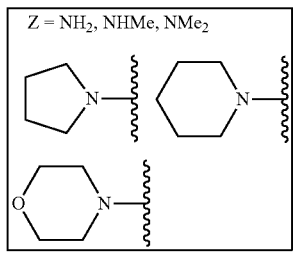
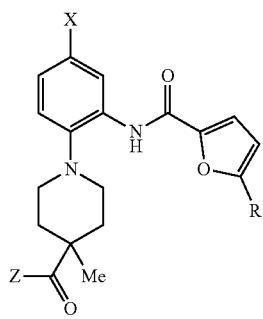
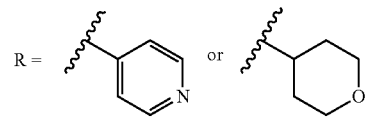
Examples 72-77, 84-90
X = CF₃, Cl, Me, OMe, cyclopropyl
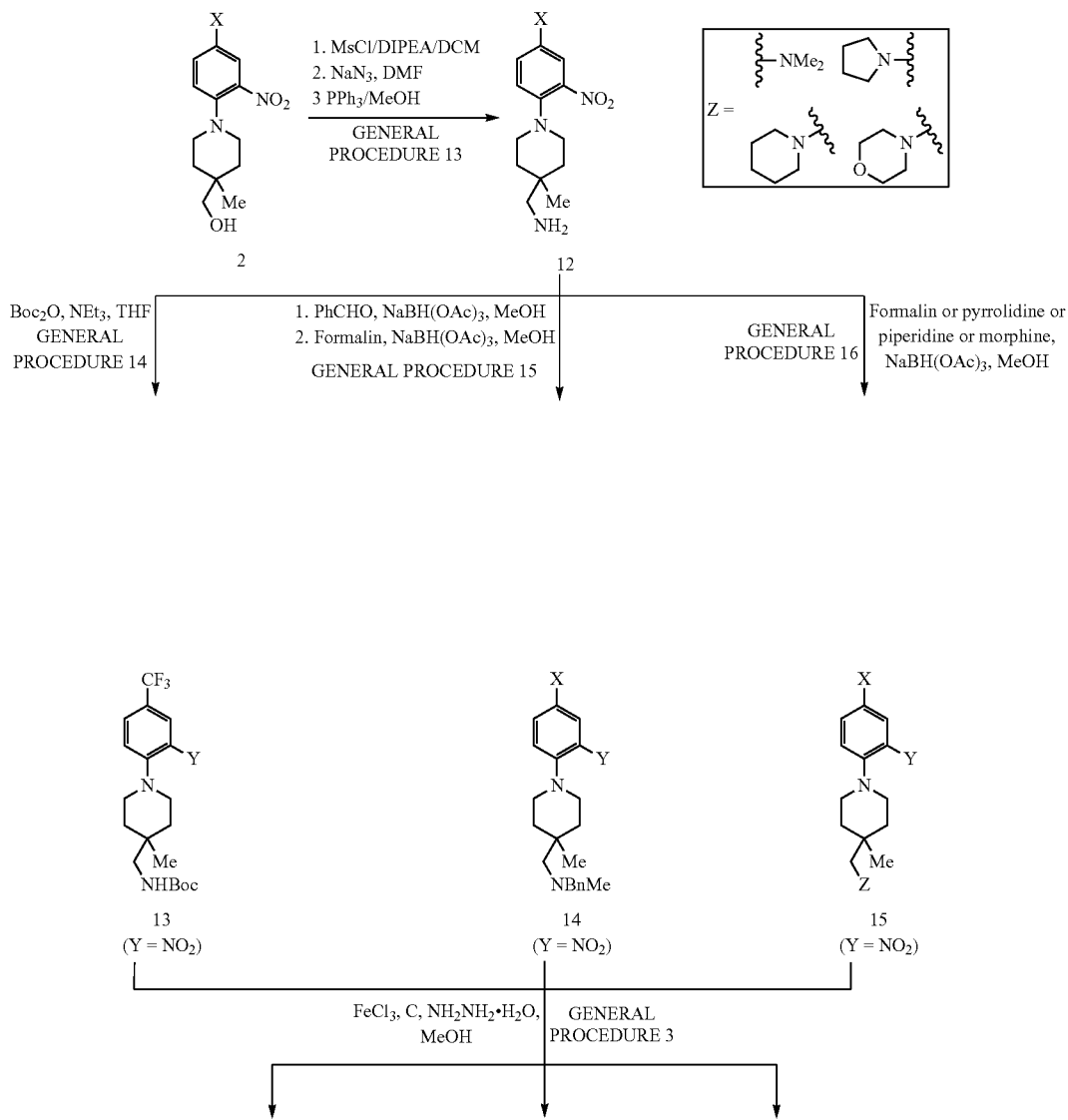
Scheme 3

1. 5-(tetrahydro-2H-pyran-4-yl)
   furan-2-carboxylic acid, POCl₃,
   pyridine
2. HCl, dioxane 16 (Y = NH₂)

17 (Y = NH₂)    18 (Y = NH₂)

GENERAL PROCEDURE 17

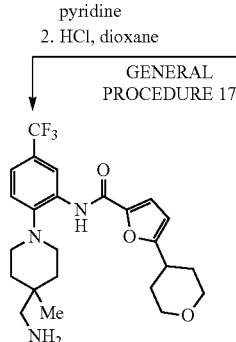

Example 81

1. 5-bromofuran-2-
   carboxylic acid, POCl₃,
   pyridine
2. 4-pyridineboronic acid,
   PdCl₂(PPh₃)₂, NaCO₃,
   DME
3. HCl, dioxane

GENERAL PROCEDURE 18

GENERAL PROCEDURE 12 methyl 5-(tetrahydro-2H-pyran-4-yl)furan-2-carboxylate
or
methyl 5-(4-pyridinyl)furan-2-carboxylate
AlMe₃, CH₂Cl₂

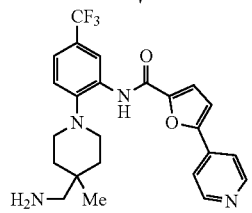

Example 78

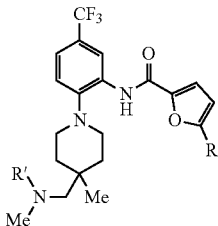

19 (R' = Bn)

H₂, Pd/BaSO₄
MeOH
GENERAL PROCEDURE 19

19 (R' = H)

Examples 79, 82

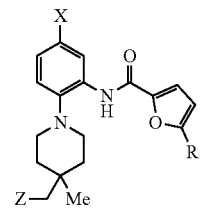

Examples 80, 83, 91-97

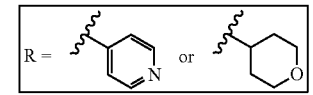

General Procedure 1—Nucleophilic Aromatic Substitution

A solution of the substituted nitrobenzene 1 (1 equiv.), saturated azaheterocycle 2 (1.1 equiv.) and solid sodium carbonate (2.5 equiv.) in anhydrous THF (3M) was heated at reflux for 16 h. The solution was allowed to cool to room temperature and the reaction solution was filtered through a pad of Celite, eluting with ethyl acetate. The organic filtrate was concentrated under reduced pressure. The resulting crude material was purified by flash chromatography on silica using a mixture of ethyl acetate in hexane as the eluent to afford the title product 2 (X=Cl, CF₃, OMe, OCF₃, Me, CHF₂).

General Procedure 2—Synthesis of Cyclopropane Building Blocks

Palladium (II) acetate (4.65 mol %) and X-phos (10 mol %) were added to a stirred suspension of chloro compounds 3 (0.35 g, 1.29 mmol), cyclopropylboronic acid (3.8 equiv.) and potassium carbonate (3 equiv.) in THF (0.18M). After nitrogen purging for 30 min, the resulting reaction mixture was heated to 70° C. for 2 h. The reaction mixture was allowed to cool down to room temperature, then filtered through a short pad of Celite, eluting with ethyl acetate. The filtrate was concentrated under reduced pressure. The residue was poured into water (30 mL) and extracted with ethyl acetate (×3). The organic extracts were combined and washed with brine, then dried over anhydrous Na₂SO₄. The solvent was removed under reduced pressure. The resulting crude material was purified by flash chromatography on silica using a mixture of ethyl acetate in hexane as the eluent to afford the title product 3 (X=cyclopropyl).

General Procedure 3—Reduction of Nitro Compounds

Hydrazine hydrate (25 equiv.) was added dropwise to a solution of compound 2 (X=Cl, CF₃, OMe, OCF₃, Me, CHF₂) or 3 (X=cyclopropane) (1 equiv.), iron(III) chloride hexahydrate (0.24 equiv.) and charcoal (0.05 g per millimole of starting material) in methanol (0.1M) at 0° C. The resulting reaction mixture was heated at reflux for 1 h. The reaction mixture was allowed to cool to room temperature then filtered through a short pad of Celite, eluting with ethyl acetate. The filtrate was removed under reduced pressure. The residue was diluted with water (70 mL) and extracted with ethyl acetate (×3). The organic extracts were combined and dried over anhydrous Na₂SO₄. The solvent was removed under reduced pressure and the resulting crude material was purified by flash chromatography on silica using a mixture of ethyl acetate in hexane as the eluent to afford the title product 4.

General Procedure 4—Synthesis of 5-(4-Pyridyl)Furan Analogs (Examples 4-10, 24, 26, 28, 32, 34, 37-42, 52-53, 55-56)

(a) Triethylamine (2 equiv.) and T3P (1.5 equiv.) were added to a solution of the aniline from general procedure 3 (1 equiv.) and 5-bromofuran-2-carboxylic acid (1.2 equiv.) in ethyl acetate (0.25M). The resulting reaction mixture was heated at reflux for 2 h. The reaction mixture was allowed to cool to room temperature. The reaction mixture was diluted with water and extracted with ethyl acetate (×3). The organic extracts were combined and dried over anhydrous $Na_2SO_4$. The solvent was removed under reduced pressure. The resulting crude material was purified by flash chromatography on silica using a mixture of ethyl acetate in hexane as an eluent to afford the title product.

(b) A solution of bromide (1.3 equiv.), pyridine-4-boronic acid (1 equiv.), $PdCl_2(PPh_3)_2$ (0.042 equiv.), 2 M aqueous sodium carbonate solution (2.8 equiv.) in 1,2-dimethoxyethane (0.08 M) was heated at reflux for 17 h under a nitrogen atmosphere. The reaction mixture was cooled to room temperature and excess DME was removed under reduced pressure. The pH of the residue was adjusted to pH ~1 using 2 M aqueous hydrochloric acid solution. The solution was extracted with dichloromethane (×3). The dichloromethane extracts were discarded. The remaining aqueous solution was neutralized to pH ~9 using solid sodium bicarbonate and extracted with ethyl acetate (×3). The organic extracts were combined and washed with water and brine, then dried over anhydrous $Na_2SO_4$. The solvent was removed under reduced pressure. The resulting crude material was purified by flash chromatography on silica using mixtures of ethyl acetate in hexane as the eluent to afford the title product.

General Procedure 5—Acylation of Anilines (Examples 1-3, 11-23, 25, 27, 29-31, 33, 35-36, 40-42, 50-51, 57)

Triethylamine (2 equiv.) and T3P (1.5 equiv.) were added to a solution of the aniline from general procedure 3 (1 equiv.) and 5-(tetrahydro-2H-pyran-4-yl)furan-2-carboxylic acid (1.2 equiv.) in ethyl acetate (0.25M). The resulting reaction mixture was heated at reflux for 2 h. The reaction mixture was allowed to cool to room temperature. The reaction mixture was diluted with water and extracted with ethyl acetate (×3). The organic extracts were combined and dried over anhydrous $Na_2SO_4$. The solvent was removed under reduced pressure. The resulting crude material was purified by flash chromatography on silica using a mixture of ethyl acetate in hexane as an eluent to afford the title product.

General Procedure 6—Silylation of Azapanols

Imidazole (2.5 equiv,) was added in one portion to a solution of azepan-4-ol 5 (1 equiv.) in dichloromethane (0.16M) at room temperature. tert-Butyl(chloro)diphenylsilane (1.35 equiv.) was then added and the resulting reaction mixture was stirred at room temperature for 1 h. The reaction mixture was diluted with water (50 mL) and extracted with dichloromethane (×3). The organic extracts were combined and washed with water and brine, then dried over anhydrous $Na_2SO_4$. The solvent was removed under reduced pressure. The resulting crude material was purified by chromatography on silica using a mixture of ethyl acetate in hexane as the eluent to afford the title product 7.

General Procedure 7—Acylation of Azapanol Scaffold (Examples 47-49)

(a) Pyridine (10 equiv.) and phosphorous oxychloride (7.2 equiv.) were added to a solution of 5-(tetrahydro-2H-pyran-4-yl)furan-2-carboxylic acid (1 equiv.) in dichloromethane (3 mL) at 0° C. under a nitrogen atmosphere. A solution of aniline (6) (1.33 equiv.) in dichloromethane (0.26M) was added to the mixture, and the resulting reaction mixture was stirred at room temperature for 1 h. The reaction mixture was acidified with dilute HCl solution and extracted with dichloromethane (×3). The organic extracts were combined and washed with water and brine, then dried over anhydrous $Na_2SO_4$. The solvent was removed under reduced pressure. The resulting crude material was purified by flash chromatography on silica using a mixture of ethyl acetate in hexane as the eluent to afford the title product.

(b) In a sealed vial, methanol (54 equiv.) and acetyl chloride (0.34 equiv.) were stirred for 20 min at 0° C. temperature under a nitrogen atmosphere, then the resulting mixture was added dropwise to a stirred solution of the amide (1 equiv.) in methanol (0.15M) at 0° C. The resulting reaction mixture was heated at 80° C. for 1 h. After cooling to room temperature, the reaction mixture was diluted with saturated sodium bicarbonate solution and extracted with ethyl acetate (×3). The organic extracts were combined and washed with water and brine, then dried over anhydrous $Na_2SO_4$. The solvent was removed under reduced pressure. The resulting crude material was purified by preparative HPLC using 10 mM ammonium bicarbonate in water and acetonitrile as mobile phase.

General Procedure 8—Synthesis of 5-(4-Pyridyl)Furan Analogs of the Azapanol Scaffold (Examples 44-46)

(a) Triethylamine (2 equiv.) and T3P (1.5 equiv.) were added to a solution of the aniline from general procedure 3 (1 equiv.) and 5-bromofuran-2-carboxylic acid (1.2 equiv.) in ethyl acetate (0.25M). The resulting reaction mixture was heated at reflux for 2 h. The reaction mixture was allowed to cool to room temperature. The reaction mixture was diluted with water and extracted with ethyl acetate (×3). The organic extracts were combined and dried over anhydrous $Na_2SO_4$. The solvent was removed under reduced pressure. The resulting crude material was purified by flash chromatography on silica using a mixture of ethyl acetate in hexane as an eluent to afford the title product.

(b) A solution of bromide (1 equiv.), pyridine-4-boronic acid (1.2 equiv.), $PdCl_2(PPh_3)_2$ (0.05 equiv), 2 M aqueous sodium carbonate solution (2 equiv.) in 1,2-dimethoxyethane (0.08 M) was heated at reflux for 17 h under a nitrogen atmosphere. The reaction mixture was cooled to room temperature and excess DME was removed under reduced pressure. The pH of the residue was adjusted to pH ~1 using 2 M aqueous hydrochloric acid solution. The solution was extracted with dichloromethane (×3). The dichloromethane extracts were discarded. The remaining aqueous solution was neutralized to pH ~9 using solid sodium bicarbonate and extracted with ethyl acetate (×3). The organic extracts were combined and washed with water and brine, then dried over anhydrous $Na_2SO_4$. The solvent was removed under reduced pressure. The resulting crude material was purified by flash chromatography on silica using mixtures of ethyl acetate in hexane as the eluent to afford the title product.

(c) In a sealed vial, methanol (54 equiv.) and acetyl chloride (0.34 equiv.) were stirred for 20 min at 0° C. temperature under a nitrogen atmosphere, then the resulting mixture was added dropwise to a stirred solution of the amide (1 equiv.) in methanol (0.15M) at 0° C. The resulting reaction mixture was heated at 80° C. for 1 h. After cooling to room temperature, the reaction mixture was diluted with saturated sodium bicarbonate solution and extracted with ethyl acetate (×3). The organic extracts were combined and washed with water and brine, then dried over anhydrous $Na_2SO_4$. The solvent was removed under reduced pressure. The resulting crude material was purified by preparative HPLC using 10 mM ammonium bicarbonate in water and acetonitrile as mobile phase.

General Procedure 9—Synthesis of Primary Amide Precursors

A solution of acid 2 (1 equiv.) and thionyl chloride (1.5 equiv.) in chloroform (0.18 M) was heated at reflux for 1 h. After concentration under reduced vacuum, the residue obtained was dissolved in THF and the resulting reaction mixture was purged with ammonia gas for 2 h at room temperature. The resulting reaction mixture was quenched with water and extracted with ethyl acetate (×3). The organic extracts were combined and washed with brine, then dried over anhydrous $Na_2SO_4$. The solvent was removed under reduced pressure and the resulting crude material was purified by flash chromatography on silica using 80% ethyl acetate in hexane as an eluent.

General Procedure 10—Synthesis of N-Methyl Amide Precursors

N,N-diisopropylamine (3.1 equiv.) and HATU (1.5 equiv.) were added to a solution of the acid (2) (1 equiv.) in DMF (0.3 M) at 0° C. under a nitrogen atmosphere and was stirred for 15 min. A solution of methylamine solution in THF (2M, 1.2 equiv.) was added to the reaction mixture and the mixture was stirred for 2 h. The resulting reaction mixture was diluted with water and extracted with ethyl acetate (×3). The organic extracts were combined and washed with brine, then dried over anhydrous $Na_2SO_4$. The solvent was removed under reduced pressure. The resulting crude material was purified by flash chromatography on silica using 30% ethyl acetate in hexane as the eluent.

General Procedure 11—Synthesis of N,N-Dimethyl Amide Precursors

N,N-Diisopropylamine (3.1 equiv.) and HATU (1.5 equiv.) were added to a solution of the acid (2) (1 equiv.) in DMF (0.3 M) at 0° C. under a nitrogen atmosphere and was stirred for 15 min. A solution of methylamine solution in THF (2M, 1.2 equiv.) was added to the reaction mixture and the mixture was stirred for 2 h. The resulting reaction mixture was diluted with water and extracted with ethyl acetate (×3). The organic extracts were combined and washed with brine, then dried over anhydrous $Na_2SO_4$. The solvent was removed under reduced pressure to afford material that was of sufficient purity to use in the next step.

General Procedure 12—Synthesis of Examples 72-77, 84-90

A 2.0 M solution of trimethylaluminium in toluene (3 equiv.) was added dropwise to a solution of aniline (9 or 10 or 11) (1 equiv.) in dichloromethane (0.075 M) at 0° C. under a nitrogen atmosphere. The mixture was stirred at room temperature for 1 h after which, a solution of either methyl 5-(tetrahydro-2H-pyran-4-yl)furan-2-carboxylate or methyl 5-(4-pyridinyl)furan-2-carboxylate (1 equiv.) in dichloromethane (0.15 M) was added dropwise at room temperature under a nitrogen atmosphere. The resulting reaction mixture was stirred at room temperature for 16 h, then diluted with saturated aqueous sodium bicarbonate solution and extracted with dichloromethane (×3). The organic extracts were combined, brine washed and dried over anhydrous $Na_2SO_4$. The solvent was removed under reduced pressure and the resulting crude material was purified by flash chromatography on silica using 2% methanol in chloroform as the eluent.

General Procedure 13—Synthesis of Aminomethyl Substituted Piperazine Precursors (a) N,N-Diisopropylethylamine (1.7 equiv.) and mesyl chloride (1.1 equiv.) were added to a solution of piperidine 2 (Z=$CO_2H$) (1 equiv.) in dichloromethane (1 M) at 0° C. under a nitrogen atmosphere and the resulting reaction mixture was stirred at room temperature overnight. Upon quenching with saturated ammonium bicarbonate solution, the aqueous solution was extracted with ethyl acetate (×3). The organic extracts were combined and washed with 5% citric acid solution, then dried over anhydrous $Na_2SO_4$. The solvent was removed under reduced pressure to afford material that was of sufficient purity to use in the next step.

(b) Sodium azide (5 equiv.) was added to a solution of mesyl derivative (4) (1 equiv.) in DMF (0.34 M) and the resultant mixture was heated at 110° C. for 16 h. Upon cooling, the resulting reaction mixture was quenched with cold water and extracted with ethyl acetate (×3). The organic extracts were combined and washed with cold brine (×2), then dried over anhydrous $Na_2SO_4$. The solvent was removed under reduced pressure to afford the azide that was of sufficient purity to use in the next step.

(c) Triphenylphosphine (1 equiv.) was added to a solution of the azide (1 equiv.) in dry methanol (1.1 M) and the resulting reaction mixture was heated at reflux for 15 min. Upon cooling to room temperature, the reaction mixture was concentrated under reduced pressure, diluted with cold water (100 mL) and the resulting aqueous solution was extracted with ethyl acetate (×3). The organic extracts were combined and washed with cold brine (×2), then dried over anhydrous $Na_2SO_4$. The solvent was removed under reduced pressure. The resulting crude material was purified by flash chromatography on silica using 5% methanol in chloroform as the eluent to afford the amine 12.

General Procedure 14—Boc Protection of Amines

Boc anhydride (1.2 equiv.) and triethylamine (1.5 equiv.) were added to a solution of amine 12 (1 equiv.) in THF (0.39 M) at room temperature under a nitrogen atmosphere and the resulting reaction mixture was stirred at room temperature for 2 h. The reaction mixture was quenched with water and extracted with ethyl acetate (×3). The organic extracts were combined and washed with brine (×2), then dried over anhydrous $Na_2SO_4$. The solvent was removed under reduced pressure and the resulting crude material was purified by flash chromatography on silica using 10% ethyl acetate in hexane as the eluent.

General Procedure 15—Synthesis of Benzyl Protected Methylamines (a) A solution of aniline 12 (1 equiv.) and benzaldehyde (1 equiv.) in methanol (0.24 M) was stirred at ambient temperature for 30 min under a nitrogen atmosphere, then sodium triacetoxyborohydride (2 equiv.) was added portionwise to the reaction mixture at 0° C. After stirring at room temperature for 16 h, the reaction mixture was diluted with saturated sodium bicarbonate solution and extracted with ethyl acetate (×3). The organic extracts were combined and washed with brine, then dried over anhydrous $Na_2SO_4$. The solvent was removed under reduced pressure and the resulting crude material was purified by column chromatography on silica using 35% ethyl acetate in hexane as the eluent.

(b) A solution of the benzylamine (1 equiv.), formalin (37-41% w/v aqueous solution of formaldehyde) (10 equiv) in methanol (0.14 M) was stirred at ambient temperature for 30 min under nitrogen atmosphere. Then sodium triacetoxyborohydride (2 equiv.) was added portionwise into the reaction mixture at 0° C. The resulting reaction mixture was allowed to stir at room temperature for 1 h. The reaction mixture was diluted with saturated sodium bicarbonate solution and extracted with ethyl acetate (×3). The organic extracts were combined and washed with brine, then dried over anhydrous Na$_2$SO$_4$. The solvent was removed under reduced pressure. The resulting crude material was purified by column chromatography on silica using 35% ethyl acetate in hexane as the eluent.

General Procedure 16—Reductive Amination to Synthesise Dimethylaminomethyl Piperazine Precursors A solution of the benzylamine (1 equiv.), formalin (37-41% w/v aqueous solution of formaldehyde) (10 equiv) in methanol (0.14 M) was stirred at ambient temperature for 30 min under nitrogen atmosphere. Then sodium triacetoxyborohydride (2 equiv.) was added portionwise into the reaction mixture at 0° C. The resulting reaction mixture was allowed to stir at room temperature for 1 h. The reaction mixture was diluted with saturated sodium bicarbonate solution and extracted with ethyl acetate (×3). The organic extracts were combined and washed with brine, then dried over anhydrous Na$_2$SO$_4$. The solvent was removed under reduced pressure. The resulting crude material was purified by column chromatography on silica using 35% ethyl acetate in hexane as the eluent.

General Procedure 17—Synthesis of Example 81

(a) Pyridine (10 equiv.) and phosphorous oxychloride (7.2 equiv.) were added to a solution of 5-(tetrahydro-2H-pyran-4-yl)furan-2-carboxylic acid (1 equiv.) in dichloromethane (0.18 M) at 0° C. under a nitrogen atmosphere. A solution of aniline (1.33 equiv.) in dichloromethane (0.11 M) was added to the mixture, and the resulting reaction mixture was stirred at room temperature for 1 h. The reaction mixture was slowly poured into ice cold water; basified up to pH ~8 with saturated ammonium bicarbonate solution (50 mL) and extracted with dichloromethane (×3). The organic extracts were combined and washed with saturated potassium hydrogen sulfate solution (×2) and brine, then dried over anhydrous Na$_2$SO$_4$. The solvent was removed under reduced pressure and the resulting crude material was purified by flash chromatography on silica using 20% ethyl acetate in hexane as the eluent.

(b) 4N HCl in dioxane (10 equiv.) was added dropwise to a solution of the amide (0.22 g, 0.38 mmol) in dioxane (0.19 M) at 0° C. under a nitrogen atmosphere and the resulting reaction mixture was stirred at room temperature for 2 h. The reaction mixture was neutralized to pH ~9 using saturated aqueous sodium bicarbonate solution, extracted with ethyl acetate (×4). The organic extracts were combined and washed with saturated aqueous sodium bicarbonate solution, then dried over anhydrous Na$_2$SO$_4$. The solvent was removed under reduced pressure. The resulting crude material was purified by preparative HPLC using 10 mM ammonium bicarbonate in water and acetonitrile as mobile phase to generate the title compound.

General Procedure 18—Synthesis of Example 78

(a) To a solution of 5-bromofuran-2-carboxylic acid (9) (0.246 g, 1.29 mmol) in dichloromethane (7 mL) were added pyridine (1.02 g, 12.90 mmol) and phosphorous oxychloride (1.39 g, 9.03 mmol) at 0° C. temperature under nitrogen atmosphere. Then to above reaction mixture was added a solution of aniline (8) (0.5 g, 1.29 mmol) in dichloromethane (8 mL) and the resulting reaction mixture was stirred at room temperature for 15 min. The reaction mixture was slowly poured into ice cold water; basified up to pH ~8 with saturated ammonium bicarbonate solution (50 mL) and extracted with dichloromethane (×3). The organic extracts were combined and washed with saturated potassium hydrogen sulfate (×2) and brine, then dried over anhydrous Na$_2$SO$_4$. The solvent was removed under reduced pressure. The resulting crude material was purified by flash chromatography on silica using 8% ethyl acetate in hexane as the eluent.

(b) A solution of bromide (1 equiv.), pyridine-4-boronic acid (1.2 equiv.), PdCl$_2$(PPh$_3$)$_2$ (0.05 equiv), 2 M aqueous sodium carbonate solution (2 equiv.) in 1,2-dimethoxyethane (0.08 M) was heated at reflux for 17 h under a nitrogen atmosphere. The reaction mixture was cooled to room temperature and excess DME was removed under reduced pressure. The pH of the residue was adjusted to pH ~1 using 2 M aqueous hydrochloric acid solution. The solution was extracted with dichloromethane (×3). The dichloromethane extracts were discarded. The remaining aqueous solution was neutralized to pH ~9 using solid sodium bicarbonate and extracted with ethyl acetate (×3). The organic extracts were combined and washed with water and brine, then dried over anhydrous Na$_2$SO$_4$. The solvent was removed under reduced pressure. The resulting crude material was purified by flash chromatography on silica using mixtures of ethyl acetate in hexane as the eluent to afford the title product.

(c) 4N HCl in dioxane (10 equiv.) was added dropwise to a solution of the amide (0.22 g, 0.38 mmol) in dioxane (0.19 M) at 0° C. under a nitrogen atmosphere and the resulting reaction mixture was stirred at room temperature for 2 h. The reaction mixture was neutralized to pH ~9 using saturated aqueous sodium bicarbonate solution, extracted with ethyl acetate (×4). The organic extracts were combined and washed with saturated aqueous sodium bicarbonate solution, then dried over anhydrous Na$_2$SO$_4$. The solvent was removed under reduced pressure. The resulting crude material was purified by preparative HPLC using 10 mM ammonium bicarbonate in water and acetonitrile as mobile phase to generate the title compound.

General Procedure 19—Hydrogenolysis of Benzylamine—Synthesis of Examples 79 and 82.

A solution of benzyl derivative (11) (1 equiv.) in methanol (1 M) was added to a slurry of Rosenmund catalyst (20% w/w) in methanol (1 M) under a nitrogen atmosphere. The resulting reaction mixture was allowed to stir under a hydrogen atmosphere at room temperature for 6 h.

The resulting reaction solution was filtered through a short pad of Celite, washed with methanol. The solvent was removed under reduced pressure and the resulting crude material was purified by preparative HPLC using 10 mM ammonium bicarbonate in water and acetonitrile as mobile phase.

Analytical data for all compounds is presented in Table 2.

Unless otherwise indicated, compounds in Table 2 and Table 3 having a stereocentre in the pyrrolidine or azepane ring were synthesised and tested as the racemic mixture of the R- and S-enantiomers.

In Vitro SRPK1 Assay

Candidate compounds were tested for SRPK1 inhibition using a Kinase-Glo assay as described previously in WO 2017/064512 A1.

CYP Inhibition Assay

Protocol Summary:

TABLE 1

| CYP Inhibition Protocol | |
| --- | --- |
| Test System | Human Liver Microsomes (CYP 1A2, 2C9, 2C19, 2D6 and 3A4) |
| Test compound | 30.00, 9.99, 3.33, 1.11, 0.37 and 0.12 µM |
| Incubation Time | 10 minutes |
| No of Replicates | Two (2) |
| Final Protein | 0.2 mg/mL |
| Substrates | CYP1A2 (Tacrine), CYP2C9 (Diclofenac), CYP2C19 (S-Mephenytoin), CYP2D6 (Dextromethorphan) and CYP3A4 (Midazolam), |
| Inhibitors | CYP1A2 (Alphanaphthaflavone), CYP2C9 (Sulfaphenazole), CYP2C19 (N-3-Benzyl nirvanol), CYP2D6 (Quinidine) and CYP3A4 (Ketoconazole) |
| Final NADPH | 1 mM |
| Potassium Phosphate | 100 mM |
| Final DMSO | <0.3% |
| Result | % Activity, % inhibition and $IC_{50}$ |
| Bioanalysis | LC-MS/MS |

Assay Procedure:

158 µL of Human Liver Microsomes working stock solution is added to a reaction plate (0.253 mg/mL, 158 µL/well). 2 µL of test compound/Positive Inhibitor working solutions is then added to the reaction plate (2 µL/well). For control, 2 µL of Acetonitrile (ACN) containing DMSO (without inhibitor) is added to the reaction plate. 20 µL of substrate pool is added to all the wells of the reaction plate. The samples are mixed in a vortexer and pre-incubated at 37° C. for 20 min. The NADPH solution is pre-warmed at 37° C. for 5 min. 20 µL of pre-warmed NADPH solution is added to the reaction plate and then incubated at 37° C. for 10 min. The reaction is terminated by adding cold ACN (200 µL/well) to the reaction mixture and centrifuging at 4,000 rpm for 20 minutes. After centrifugation, supernatant is separated and analyzed by LC-MS/MS.

% inhibition and $IC_{50}$ are calculated using Graphpad Prism software.

Results from the SRPK1 assay and CYP inhibition assay are presented in Table 3.

As reference compounds, the following compounds were tested:

Reference Example 1—N-(2-(4-(Pyridin-2-ylmethyl)piperazin-1-yl)-5-trifluoromethyl)phenyl)-5-(pyridin-4-yl)furan-2-carboxamide;

Reference Example 2—N-(2-(4-(furan-2-ylmethyl)piperazin-1-yl)-5-(trifluoromethyl)phenyl)-5-(pyridin-4-yl)furan-2-carboxamide;

Reference Example 3—N-(2-(4-((1H-pyrazol-3-yl)methyl)piperazin-1-yl)-5-(trifluoromethyl)-phenyl)-5-(tetrahydro-2H-pyran-4-yl)furan-2-carboxamide;

Reference Example 4—N-(2-(4-(oxazol-4-ylmethyl)piperazin-1-yl)-5-(trifluoromethyl)phenyl)-5-(pyridin-4-yl)furan-2-carboxamide; and Reference Example 5: 5-(pyridin-4-yl)-N-(2-(5-(thiazol-2-ylmethyl)piperazin-1-yl)-5-(trifluoromethyl)phenyl)furan-2-carboxamide.

As can be seen, all compounds of the present invention are not only potent inhibitors of SRPK1 but also exhibit acceptable levels of CYP inhibition, unlike the reference compounds. In terms of acceptable levels of CYP inhibition, it is generally held that the less potently a candidate compound inhibits any CYP enzyme, the fewer the risks of unfavourable drug-drug interactions or other side effects associated with toxicity. Furthermore, acceptable levels of CYP activity can be measured as a function of SRPK1 activity for a particular compound. In particular, compounds which are less potent CYP inhibitors than they are SRPK1 inhibitors and are at least 100 times less potent in this regard (as determined with reference to $IC_{50}$ measurements) are also considered advantageous compounds which represent a clinically significant improvement over the prior art compounds.

More generally, if a candidate drug compound has an $IC_{50}$ of greater than 1 µM (1000 nM) for any of the core CYP enzymes associated with drug metabolism (CYP1A2, CYP2C9, CYP2C19, CYP2D6 and CYP3A4) then the risk of any unfavourable drug-drug interactions or other toxicity issues is considered low enough to be acceptable. A CYP activity profile of greater than 10 µM (10000 nM) for any of the tested CYPs is particularly preferred.

While these core CYPs are responsible for metabolizing over 95% of drugs and other xenobiotic substances, within this core group CYP2D6 and CYP3A4 are considered most important. Even moderately potent inhibitors of these two enzymes in particular are therefore not considered suitable candidate drugs for systemic administration.

It should be noted that for topical applications, such as the topical treatment of ocular neovascularization, CYP activity is of a lesser concern, as a compound administered topically (such as to the eye) is not likely to be metabolized in the liver, where the majority of CYP activity takes place.

In Vivo Angiogenesis Assay: Laser-Induced Choroidal Neovascularisation (CNV) Protocol 6-8 week-old female C57/B6 mice were anesthetized with an intraperitoneal injection of a mixture of 50 mg/kg ketamine and 0.5 mg/kg medetomidine. The pupils were immediately dilated by topical (eyedrop) application with a dilator such as 5% phenylephrine hydrochloride and 1% tropicamide. Four photocoagulation lesions were delivered with a green Merilas 532α laser (450 mW, 130 ms) between the "large" retinal vessels in clear space with no vessels in a peripapillary distribution at a distance of 1-2 disc-diameters in each eye. Only clean laser lesions with a subretinal bubble at the time of treatment were included in the study. Immediately following laser photocoagulation the animals were given topical eye drops of candidate compounds twice daily (2 mg/mL, 10 eyes held for 30 seconds to prevent animal wiping drop away).

After one week, mice were anesthetized with an intraperitoneal injection of a mixture of 50 mg/kg ketamine and 0.5 mg/kg medetomidine. The pupils were immediately dilated by topical (eyedrop) application with a dilator such as 5% phenylephrine hydrochloride and 1% tropicamide. Mice were administered an intraperitoneal injection of sodium fluorescein (10%). Phase contrast and green fluorescent fundus images were taken with an angiography microscope and camera with each lesion in focus. The mice were killed by a schedule 1 method and eyes were either unfixed for retinal dissection and protein extraction, or fixed and enucleated and choroids stained and examined.

The optical density of each well was measured immediately, using a microplate reader set to 450 nm.

FIG. 1(a) shows that Compound 12 has improved anti-angiogenic activity on lesion size and the same efficacy as reference compounds in a laser-induced mouse model of CNV, with the optical images on which the data is based shown in FIG. 1(b).

TABLE 2

Analytical data

| Example | Structure | Data |
|---|---|---|
| 1 | [structure: 4-CF₃ phenyl, 2-(4-hydroxy-4-methylpiperidin-1-yl), N-H picolinamide] | N-(2-(4-hydroxy-4-methylpiperidin-1-yl)-5-(trifluoromethyl)phenyl)picolinamide<br>$^1$H NMR (400 MHz, DMSO-d$_6$) δ 1.27 (s, 3H), 1.70-1.73 (m, 2H), 1.85 (t, J = 10 Hz, 2H), 2.83-2.86 (m, 2H), 3.03-3.08 (m, 2H), 4.41 (s, 1H), 7.46 (br s, 2H), 7.73 (dd, J = 4.8, 6.4 Hz, 1H), 8.13 (m, 1H), 8.21 (m, 1H), 8.75-8.79 (m, 2H), 11.00 (s, 1H).<br>HPLC purity: 100%<br>MS (ESI-MS): m/z calcd for C$_{19}$H$_{21}$F$_3$N$_3$O$_2$ [MH]$^+$ 380.16, found 380.29 |
| 2 | [structure: 4-Cl phenyl, 2-(4-hydroxy-4-methylpiperidin-1-yl), N-H picolinamide] | N-(5-chloro-2-(4-hydroxy-4-methylpiperidin-1-yl)-phenyl)picolinamide<br>$^1$H NMR (400 MHz, DMSO-d$_6$) δ 1.25 (s, 3H), 1.67-1.71 (m, 2H), 1.78-1.81 (m, 2H), 2.72-2.75 (m, 2H), 2.99 (t, J = 10 Hz, 2H), 7.15 (d, J = 6.4 Hz, 1H), 7.29 (d, J = 8.4 Hz, 1H), 7.70-7.73 (m, 1H), 8.09-8.20 (m, 2H), 8.48 (s, 1H), 8.74 (m, 1H), 11.06 (s, 1H).<br>HPLC purity: 97.25%<br>MS (ESI-MS): m/z calcd for C$_{18}$H$_{21}$$^{35}$ClN$_3$O$_2$ [MH]$^+$ 346.13, found 346.23 |
| 3 | [structure: 4-cyclopropyl phenyl, 2-(4-hydroxy-4-methylpiperidin-1-yl), N-H picolinamide] | N-(5-cyclopropyl-2-(4-hydroxy-4-methylpiperidin-1-yl)phenyl)-picolinamide<br>$^1$H NMR (400 MHz, DMSO-d$_6$) δ 0.61-0.69 (m, 2H), 0.86-0.97 (m, 2H), 1.25 (s, 3H), 1.66-1.70 (m, 2H), 1.77-1.84 (m, 2H), 1.88-1.94 (m, 1H), 2.69-2.71 (m, 2H), 2.50-2.99 (m, 2H), 4.30 (s, 1H), 6.83 (dd, J = 2, 8.4 Hz, 1H), 7.16 (d, J = 8 Hz, 1H), 7.67-7.71 (m, 1H), 8.10 (m, 1H), 8.18-8.22 (m, 2H), 8.73 (d, J = 4.4 Hz, 1H), 11.08 (s, 1H).<br>HPLC purity: 100%<br>MS (ESI-MS): m/z calcd for C$_{21}$H$_{26}$N$_3$O$_2$ [MH]$^+$ 352.20, found 352.17 |

TABLE 2-continued

| Analytical data | | |
|---|---|---|
| Example | Structure | Data |
| 4 | | N-(2-(4-hydroxy-4-methylpiperidin-1-yl)-5-(trifluoromethyl)phenyl)-5-(pyridin-4-yl)furan-2-carboxamide<br>$^1$H NMR (400 MHz, DMSO-$d_6$) δ 1.23 (s, 3H), 1.70-1.81 (m, 4H), 2.86 (d, J = 11.6 Hz, 2H), 3.06 (t, J = 9.6 Hz, 2H), 4.46 (s, 1H), 7.50-7.51 (m, 3H), 7.56 (d, J = 3.6 Hz, 1H), 7.85 (d, J = 5.6 Hz, 2H), 8.55 (s, 1H), 8.70 (d, J = 6 Hz, 2H), 9.71 (s, 1H).<br>HPLC purity: 99.02%<br>MS (ESI-MS): m/z calcd for $C_{23}H_{23}F_3N_3O_3$ [MH]$^+$ 446.17, found 446.42 |
| 5 | | N-(5-chloro-2-(4-hydroxy-4-methylpiperidin-1-yl)phenyl)-5-(pyridin-4-yl)furan-2-carboxamide<br>$^1$H NMR (400 MHz, DMSO-$d_6$) δ 1.23 (s, 3H), 1.70-1.80 (m, 4H), 2.74-2.77 (m, 2H), 2.97-3.03 (m, 2H), 4.47 (s, 1H), 7.20 (dd, J = 2.4, 8.8 Hz, 1H), 7.37 (d, J = 8.4 Hz, 1H), 7.49 (d, J = 3.6, 1H), 7.56 (d, J = 3.6 Hz, 1H), 7.83-7.85 (m, 2H), 8.33 (d, J = 2.4 Hz, 1H), 8.69-8.73 (m, 2H), 9.76 (s, 1H).<br>HPLC purity: 100%<br>MS (ESI-MS): m/z calcd for $C_{22}H_{23}{}^{35}ClN_3O_3$ [MH]$^+$ 412.14, found 411.97 |
| 6 | | N-(5-cyclopropyl-2-(4-hydroxy-4-methylpiperidin-1-yl)phenyl)-5-(pyridin-4-yl)furan-2-carboxamide<br>$^1$H NMR (400 MHz, DMSO-$d_6$) δ 0.61-0.65 (m, 2H), 0.93-0.97 (m, 2H), 1.23 (s, 3H), 1.70-1.77 (m, 4H), 1.88-1.94 (m, 1H), 2.68-2.72 (m, 2H), 2.95-3.01 (m, 2H), 4.44 (s, 1H), 6.86 (dd, J = 1.6, 8 Hz, 1H), 7.22 (d, J = 8 Hz, 1H), 7.43 (d, J = 3.6 Hz, 1H), 7.55 (d, J = 4 Hz, 1H), 7.83-7.84 (m, 2H), 8.06 (d, J = 2 Hz, 1H), 8.70 (d, J = 6 Hz, 2H), 9.77 (s, 1H).<br>HPLC purity: 100%<br>MS (ESI-MS): m/z calcd for $C_{25}H_{28}N_3O_3$ [MH]$^+$ 418.21, found 418.20 |
| 7 | | N-(5-(difluoromethyl)-2-(4-hydroxy-4-methyl-piperidin-1-yl)phenyl)-5-(pyridin-4-yl)furan-2-carboxamide<br>$^1$H NMR (400 MHz, DMSO-$d_6$) δ 1.22 (s, 3H), 1.70-1.80 (m, 4H), 2.80-2.83 (m, 2H), 3.01-3.06 (m, 2H), 4.47 (s, 1H), 7.05 (t, J = 56 Hz, 1H), 7.35 (d, J = 8 Hz, 1H), 7.45 (d, J = 7.6 Hz, 1H), 7.49 (d, J = 3.6 Hz, 1H), 7.56 (d, J = 3.6 Hz, 1H), 7.85 (d, J = 6 Hz, 2H), 8.46 (s, 1H), 8.70 (d, J = 5.6 Hz, 2H), 9.73 (s, 1H).<br>HPLC purity: 96.71%<br>MS (ESI-MS): m/z calcd for $C_{23}H_{24}F_2N_3O_3$ [MH]$^+$ 428.18, found 428.19 |

TABLE 2-continued

| Example | Structure | Data |
|---|---|---|
| 8 | 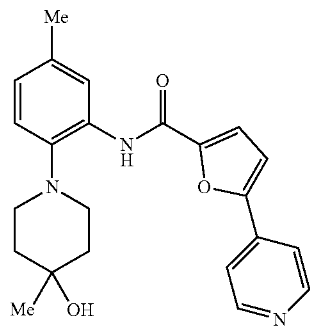 [SMILES: Cc1ccc(N2CCC(C)(O)CC2)c(NC(=O)c2ccc(-c3ccncc3)o2)c1] | N-(2-(4-hydroxy-4-methylpiperidin-1-yl)-5-methylphenyl)-5-(pyridin-4-yl)furan-2-carboxamide<br>$^1$H NMR (400 MHz, DMSO-d$_6$) δ 1.23 (s, 3H), 1.73-1.78 (m, 4H), 2.30 (s, 3H), 2.69-2.72 (m, 2H), 2.95-3.00 (m, 2H), 4.45 (s, 1H), 6.94-6.96 (m, 1H), 7.24 (d, J = 8 Hz, 1H), 7.44 (d, J = 3.6 Hz, 1H), 7.55 (d, J = 3.6 Hz, 1H), 7.84 (d, J = 5.6 Hz, 2H), 8.14 (s, 1H), 8.70 (d, J = 4.4 Hz, 2H), 9.78 (s, 1H).<br>HPLC purity: 97.55%<br>MS (ESI-MS): m/z calcd for C$_{23}$H$_{26}$N$_3$O$_3$ [MH]$^+$ 392.20, found 392.24 |
| 9 | 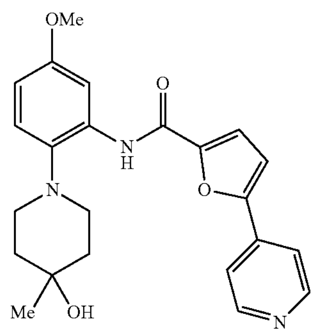 [SMILES: COc1ccc(N2CCC(C)(O)CC2)c(NC(=O)c2ccc(-c3ccncc3)o2)c1] | N-(2-(4-hydroxy-4-methylpiperidin-1-yl)-5-methoxyphenyl)-5-(pyridin-4-yl)furan-2-carboxamide<br>$^1$H NMR (400 MHz, DMSO-d$_6$) δ 1.25 (s, 3H), 1.73-1.74 (m, 4H), 2.67-2.70 (m, 2H), 2.97-2.98 (m, 2H), 3.75 (s, 3H), 4.47 (s, 1H), 6.71 (dd, J = 2.8, 8.8 Hz, 1H), 7.31 (d, J = 8.8 Hz, 1H), 7.44 (d, J = 3.6 Hz, 1H), 7.55 (d, J = 4 Hz, 1H), 7.83 (dd, J = 0.8, 4.8 Hz, 2H), 7.99 (d, J = 2.8 Hz, 1H), 8.69 (dd, J = 0.8, 4.8 Hz, 2H), 9.91 (s, 1H).<br>HPLC purity: 100%<br>MS (ESI-MS): m/z calcd for C$_{23}$H$_{26}$N$_3$O$_4$ [MH]$^+$ 408.19, found 408.26 |
| 10 | 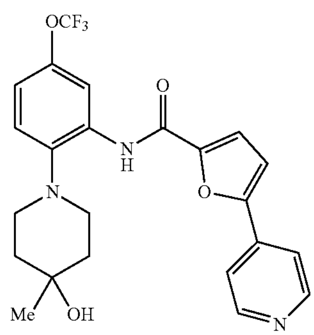 [SMILES: CC1(O)CCN(c2ccc(OC(F)(F)F)cc2NC(=O)c2ccc(-c3ccncc3)o2)CC1] | N-(2-(4-hydroxy-4-methylpiperidin-1-yl)-5-(trifluoromethoxy)phenyl)-5-(pyridin-4-yl)furan-2-carboxamide<br>$^1$H NMR (400 MHz, DMSO-d$_6$) δ 1.25 (s, 3H), 1.72-1.82 (m, 4H), 2.77-2.80 (m, 2H), 3.00-3.06 (m, 2H), 4.45 (s, 1H), 7.13-7.15 (m, 1H), 7.45-7.49 (m, 2H), 7.56 (d, J = 3.6 Hz, 1H), 7.84 (d, J = 6 Hz, 2H), 8.31 (s, 1H), 8.70 (d, J = 5.6 Hz, 2H), 9.80 (s, 1H).<br>HPLC purity: 95.95%<br>MS (ESI-MS): m/z calcd for C$_{23}$H$_{23}$F$_3$N$_3$O$_4$ [MH]$^+$ 462.16, found 462.00 |
| 11 | 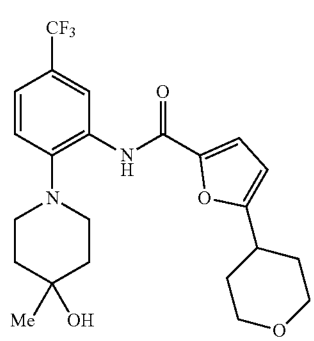 [SMILES: CC1(O)CCN(c2ccc(C(F)(F)F)cc2NC(=O)c2ccc(C3CCOCC3)o2)CC1] | N-(2-(4-hydroxy-4-methylpiperidin-1-yl)-5-(trifluoromethyl)-phenyl)-5-(tetrahydro-2H-pyran-4-yl)furan-2-carboxamide<br>$^1$H NMR (400 MHz, DMSO-d$_6$) δ 1.23 (s, 3H), 1.67-1.79 (m, 6H), 1.91-1.95 (dd, J = 1.6, 12.8 Hz, 2H), 2.80 (d, J = 11.6 Hz, 2H), 3.02-3.08 (m, 3H), 3.45 (td, J = 2, 11.6 Hz, 2H), 3.93 (dd, J = 2.4, 11.6 Hz, 2H), 4.43 (s, 1H), 6.46-6.47 (m, 1H), 7.25 (d, J = 3.6 Hz, 1H), 7.44-7.50 (m, 2H), 8.63 (s, 1H), 9.45 (s, 1H).<br>HPLC purity: 98.26%<br>MS (ESI-MS): m/z calcd for C$_{23}$H$_{28}$F$_3$N$_2$O$_4$ [MH]$^+$ 453.20, found 453.38 |

TABLE 2-continued

Analytical data

| Example | Structure | Data |
|---|---|---|
| 12 | 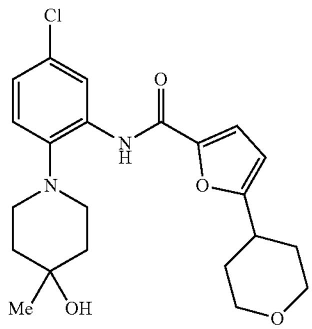 | N-(5-cyclopropyl-2-(4-hydroxy-4-methylpiperidin-1-yl)phenyl)-5-(pyridin-4-yl)furan-2-carboxamide<br>$^1$H NMR (400 MHz, DMSO-$d_6$) δ 1.22 (s, 3H), 1.66-1.76 (m, 6H), 1.92 (dd, J = 1.6, 12.8 Hz, 2H), 2.68-2.71 (m, 2H), 2.97-3.08 (m, 3H), 3.45 (td, J = 2, 11.6 Hz, 2H), 3.93 (dd, J = 2.4, 11.6 Hz, 2H), 4.41 (s, 1H), 6.46 (dd, J = 0.4, 3.2 Hz, 1H), 7.15 (dd, J = 2.4, 8.4 Hz, 1H), 7.23 (d, J = 3.2 Hz, 1H), 7.34 (d, J = 8.4 Hz, 1H), 8.37 (s, 1H), 9.55 (s, 1H).<br>HPLC purity: 99.25%<br>MS (ESI-MS): m/z calcd for $C_{22}H_{28}{}^{35}ClN_2O_4$ [MH]$^+$ 419.17, found 419.03 |
| 13 | 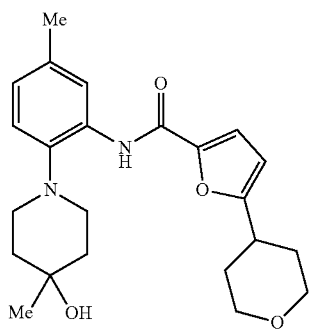 [SMILES: Cc1ccc(N2CCC(C)(O)CC2)c(NC(=O)c2ccc(C3CCOCC3)o2)c1] | N-(2-(4-hydroxy-4-methylpiperidin-1-yl)-5-methylphenyl)-5-(tetrahydro-2H-pyran-4-yl)furan-2-carboxamide<br>$^1$H NMR (400 MHz, DMSO-$d_6$) δ 1.22 (s, 3H), 1.66-1.76 (m, 6H), 1.93 (dd, J = 2, 12.8 Hz, 2H), 2.28 (s, 3H), 2.65 (dd, J = 4, 7.6 Hz, 2H), 2.95-3.07 (m, 3H), 3.45 (td, J = 2, 11.6 Hz, 2H), 3.93 (dd, J = 2.4, 11.6 Hz, 2H), 4.37 (s, 1H), 6.43 (dd, J = 0.8, 3.6 Hz, 1H), 6.91 (dd, J = 1.6, 8 Hz, 1H), 7.17-7.21 (m, 2H), 8.17 (d, J = 1.2 Hz, 1H), 9.58 (s, 1H).<br>HPLC purity: 100%<br>MS (ESI-MS): m/z calcd for $C_{23}H_{31}N_2O_4$ [MH]$^+$ 399.23, found 399.27 |
| 14 | 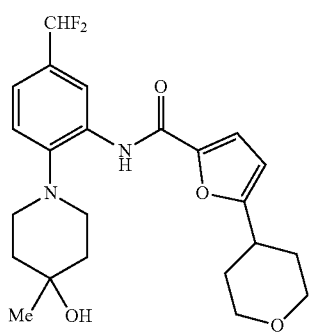 | N-(5-(difluoromethyl)-2-(4-hydroxy-4-methyl-piperidin-1-yl)phenyl)-5-(tetrahydro-2H-pyran-4-yl)furan-2-carboxamide<br>$^1$H NMR (400 MHz, DMSO-$d_6$) δ 1.23 (s, 3H), 1.67-1.78 (m, 6H), 1.93 (dd, J = 2, 12.8 Hz, 2H), 2.75 (dd, J = 3.6, 8 Hz, 2H), 3.00-3.08 (m, 3H), 3.45 (td, J = 2, 11.6 Hz, 2H), 3.92-3.95 (m, 2H), 4.42 (s, 1H), 6.45 (dd, J = 0.8, 3.6 Hz, 1H), 7.03 (t, J = 56 Hz, 1H), 7.23 (d, J = 3.6 Hz, 1H), 7.30 (d, J = 7.6 Hz, 1H), 7.42 (d, J = 8.4 Hz, 1H), 8.52 (s, 1H), 9.50 (s, 1H).<br>HPLC purity: 96.04%<br>MS (ESI-MS): m/z calcd for $C_{23}H_{29}F_2N_2O_4$ [MH]$^+$ 435.21, found 435.25 |
| 15 | 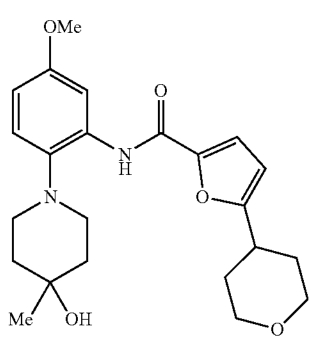 [SMILES: COc1ccc(N2CCC(C)(O)CC2)c(NC(=O)c2ccc(C3CCOCC3)o2)c1] | N-(2-(4-hydroxy-4-methylpiperidin-1-yl)-5-methoxyphenyl)-5-(tetrahydro-2H-pyran-4-yl)furan-2-carboxamide<br>$^1$H NMR (400 MHz, DMSO-$d_6$) δ 1.22 (s, 3H), 1.68-1.77 (m, 5H), 1.93 (d, J = 11.2 Hz, 2H), 2.55-3.64 (m, 3H), 2.96-3.05 (m, 3H), 3.42-3.48 (m, 2H), 3.74 (s, 3H), 3.93 (dd, J = 2.4, 11.2 Hz, 2H), 4.38 (s, 1H), 6.44 (dd, J = 0.8, 3.6 Hz, 1H), 6.66 (dd, J = 2.8, 8.8 Hz, 1H), 7.18 (d, J = 3.6 Hz, 1H), 7.26 (d, J = 8.8 Hz, 1H), 7.99 (d, J = 2.8 Hz, 1H), 9.73 (s, 1H).<br>HPLC purity: 99.74%<br>MS (ESI-MS): m/z calcd for $C_{23}H_{31}N_2O_5$ [MH]$^+$ 415.22, found 415.27 |

TABLE 2-continued

Analytical data

| Example | Structure | Data |
|---|---|---|
| 16 | 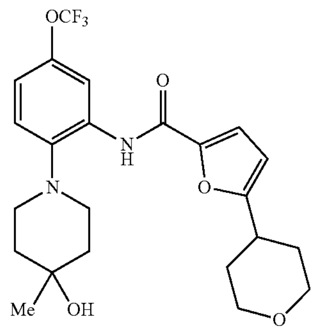 [SMILES: CC1(O)CCN(c2ccc(OC(F)(F)F)cc2NC(=O)c2ccc(C3CCOCC3)o2)CC1] | N-(2-(4-hydroxy-4-methylpiperidin-1-yl)-5-(trifluoromethoxy)phenyl)-5-(tetrahydro-2H-pyran-4-yl)furan-2-carboxamide<br>$^1$H NMR (400 MHz, DMSO-$d_6$) δ 1.23 (s, 3H), 1.67-1.77 (m, 6H), 1.93 (dd, J = 1.6, 8.8 Hz, 2H), 2.71-2.73 (m, 2H), 3.00-3.05 (m, 3H), 3.45 (td, J = 2, 11.6 Hz, 2H), 3.93 (dd, J = 2.4, 11.6 Hz, 2H), 4.42 (s, 1H), 6.46 (dd, J = 0.8, 3.6 Hz, 1H), 7.08-7.10 (m, 1H), 7.24 (d, J = 3.6 Hz, 1H), 7.43 (d, J = 8.8 Hz, 1H), 8.33 (d, J = 2 Hz, 1H), 9.60 (s, 1H).<br>HPLC purity: 99.96%<br>MS (ESI-MS): m/z calcd for $C_{23}H_{28}F_3N_2O_5$ [MH]$^+$ 469.20, found 469.16 |
| 17 | 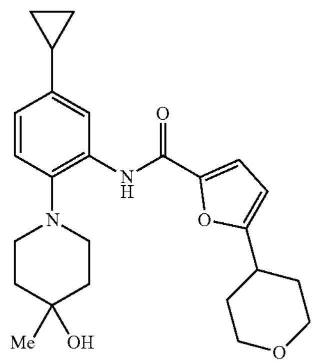 [SMILES: CC1(O)CCN(c2ccc(C3CC3)cc2NC(=O)c2ccc(C3CCOCC3)o2)CC1] | N-(5-cyclopropyl-2-(4-hydroxy-4-methylpiperidin-1-yl)phenyl)-5-(tetrahydro-2H-pyran-4-yl)furan-2-carboxamide<br>$^1$H NMR (400 MHz, DMSO-$d_6$) δ 0.59-0.63 (m, 2H), 0.91-0.96 (m, 2H), 1.22 (s, 3H), 1.66-1.76 (m, 6H), 1.87-1.94 (m, 3H), 2.63-2.66 (m, 2H), 2.95-3.07 (m, 3H), 3.45 (dd, J = 9.6, 11.6 Hz, 2H), 3.93 (dd, J = 2, 11.6 Hz, 2H), 4.38 (s, 1H), 6.43 (d, J = 2.8 Hz, 1H), 6.81 (dd, J = 2, 81 Hz, 1H), 7.16-7.20 (m, 2H), 8.09 (d, J = 2 Hz, 1H), 9.57 (s, 1H).<br>HPLC purity: 98.96%<br>MS (ESI-MS): m/z calcd for $C_{25}H_{33}N_2O_4$ [MH]$^+$ 425.24, found 425.24 |
| 18 | 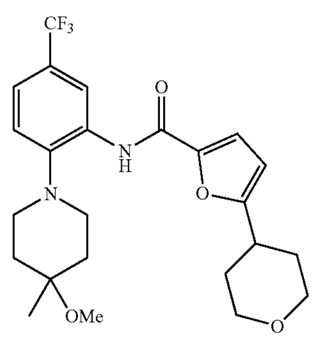 [SMILES: COC1(C)CCN(c2ccc(C(F)(F)F)cc2NC(=O)c2ccc(C3CCOCC3)o2)CC1] | N-(2-(4-methoxy-4-methylpiperidin-1-yl)-5-(trifluoromethyl)-phenyl)-5-(tetrahydro-2H-pyran-4-yl)furan-2-carboxamide<br>$^1$H NMR (400 MHz, DMSO-$d_6$) δ 1.21 (s, 3H), 1.67-1.77 (m, 4H), 1.91-1.94 (m, 4H), 2.81 (d, J = 11.6 Hz, 2H), 2.95 (d, J = 9.6 Hz, 2H), 3.02-3.08 (m, 1H), 3.17 (s, 3H), 3.45 (dd, J= 10, 11.6 Hz, 2H), 3.94 (dd, J = 2, 11.6 Hz, 2H), 6.47 (d, J = 3.2 Hz, 1H), 7.25 (d, J = 3.6 Hz, 1H), 7.44-7.50 (m, 2H), 8.63 (s, 1H), 9.45 (s, 1H).<br>HPLC purity: 100%<br>MS (ESI-MS): m/z calcd for $C_{24}H_{30}F_3N_2O_4$ [MH]$^+$ 467.22, found 467.16 |
| 19 | 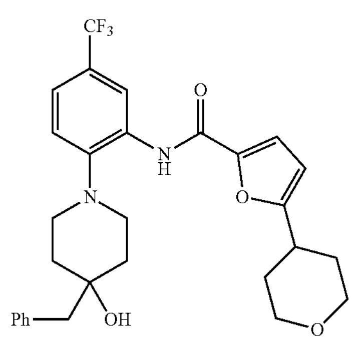 [SMILES: O=C(Nc1cc(C(F)(F)F)ccc1N1CCC(O)(Cc2ccccc2)CC1)c1ccc(C2CCOCC2)o1] | N-(2-(4-hydroxy-4-methylazepan-1-yl)-5-(trifluoromethyl)phenyl)-5-(pyridin-4-yl)furan-2-carboxamide<br>$^1$H NMR (400 MHz, DMSO-$d_6$) δ 1.61 (d, J = 12.8 Hz, 2H), 1.74-1.83 (m, 4H), 1.98 (dd, J = 2, 13.2 Hz, 2H), 2.76 (s, 2H), 2.83 (d, J = 11.2 Hz, 2H), 3.02 (t, J = 10.8 Hz, 2H), 3.11 (m, 1H), 3.50 (td, J = 2, 11.6 Hz, 2H), 3.98 (dd, J = 2, 11.6 Hz, 2H), 4.44 (s, 1H), 6.48-6.49 (m, 1H), 7.22-7.31 (m, 6H), 7.46-7.49 (m, 2H), 8.62 (s, 1H), 9.48 (s, 1H).<br>HPLC purity: 98.51%<br>MS (ESI-MS): m/z calcd for $C_{29}H_{31}F_3N_2O_4$ [MH]$^+$ 528.22, found 529.05 |

TABLE 2-continued

Analytical data

| Example | Structure | Data |
|---|---|---|
| 20 | 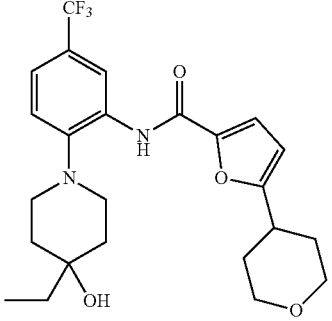 [SMILES: CCC1(O)CCN(c2ccc(C(F)(F)F)cc2NC(=O)c2ccc(C3CCOCC3)o2)CC1] | N-(2-(4-ethyl-4-hydroxypiperidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 0.91 (t, J = 7.6 Hz, 3H), 1.48 (q, J = 7.6 Hz, 2H), 1.66-1.76 (m, 6H), 1.92 (dd, J = 1.6, 12.8 Hz, 2H), 2.82 (d, J = 11.2 Hz, 2H), 3.00-3.09 (m, 3H), 3.43 (td, J = 2, 11.6 Hz, 2H), 3.93 (dd, J = 2, 11.6 Hz, 2H), 4.21 (s, 1H), 6.46 (dd, J = 0.8, 3.6 Hz, 1H), 7.25 (d, J = 3.6 Hz, 1H), 7.44-7.49 (m, 2H), 8.64 (s, 1H), 9.41 (s, 1H).<br>HPLC purity: 99.89%<br>MS (ESI-MS): m/z calcd for $C_{24}H_{30}F_3N_2O_4$ [MH]$^+$ 467.22, found 467.11 |
| 21 | 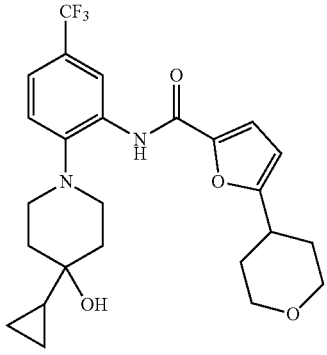 [SMILES: O=C(Nc1cc(C(F)(F)F)ccc1N1CCC(O)(C2CC2)CC1)c1ccc(C2CCOCC2)o1] | N-(2-(4-cyclopropyl-4-hydroxypiperidin-1-yl)-5-(trifluoromethyl)-phenyl)-5-(tetrahydro-2H-pyran-4-yl)furan-2-carboxamide<br>$^1$H NMR (400 MHz, DMSO-$d_6$) δ 0.24-0.29 (m, 2H), 0.38-0.42 (m, 2H), 0.87-0.91 (m, 1H), 1.66-1.85 (m, 6H), 1.93 (dd, J = 1.6, 12.8 Hz, 2H), 2.86 (d, J = 11.6 Hz, 2H), 3.04 (m, 3H), 3.42 (td, J = 1.6, 11.6 Hz, 2H), 3.91 (dd, J = 2.4, 11.6 Hz, 2H), 4.01 (s, 1H), 6.47 (dd, J = 0.8, 3.6 Hz, 1H), 7.26 (d, J = 3.6 Hz, 1H), 7.47 (s, 2H), 8.64 (s, 1H), 9.71 (s, 1H).<br>HPLC purity: 95.52%<br>MS (ESI-MS): m/z calcd for $C_{25}H_{30}F_3N_2O_4$ [MH]$^+$ 479.22, found 479.17 |
| 22 | 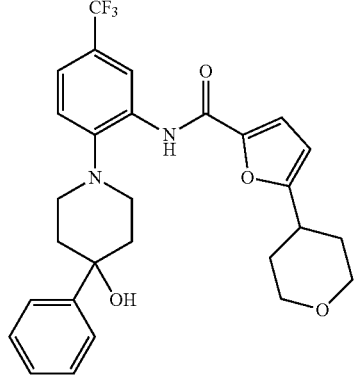 [SMILES: O=C(Nc1cc(C(F)(F)F)ccc1N1CCC(O)(c2ccccc2)CC1)c1ccc(C2CCOCC2)o1] | N-(2-(4-hydroxy-4-phenylpiperidin-1-yl)-5-(trifluoromethyl)-phenyl)-5-(tetrahydro-2H-pyran-4-yl)furan-2-carboxamide<br>$^1$H NMR (400 MHz, DMSO-$d_6$) δ 1.58-1.65 (m, 2H), 1.81-1.89 (m, 4H), 2.19-2.26 (m, 2H), 2.90-2.98 (m, 3H), 3.16-3.27 (m, 4H), 3.75 (dd, J = 2, 11.6 Hz, 2H), 5.15 (s, 1H), 6.44 (dd, J = 0.8, 3.6 Hz, 1H), 7.26-7.31 (m, 2H), 7.40 (t, J = 7.2 Hz, 2H), 7.48-7.54 (m, 2H), 7.58-7.60 (m, 2H), 8.65 (s, 1H), 9.38 (s, 1H).<br>HPLC purity: 100%<br>MS (ESI-MS): m/z calcd for $C_{28}H_{30}F_3N_2O_4$ [MH]$^+$ 515.22, found 515.03 |
| 23 | 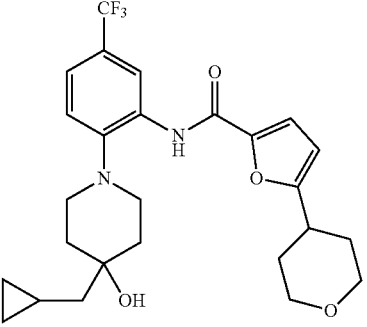 [SMILES: O=C(Nc1cc(C(F)(F)F)ccc1N1CCC(O)(CC2CC2)CC1)c1ccc(C2CCOCC2)o1] | N-(2-(4-(cyclopropylmethyl)-4-hydroxypiperidin-1-yl)-5-(trifluoromethyl)phenyl)-5-(tetrahydro-2H-pyran-4-yl)furan-2-carboxamide<br>$^1$H-NMR (400 MHz, DMSO-$d_6$) δ 0.04-0.07 (m, 2H), 0.44-0.48 (m, 2H), 0.86-0.90 (m, 1H), 1.40 (d, J = 6.4 Hz, 2H), 1.64-1.82 (m, 6H), 1.90 (dd, J = 2, 13.2 Hz, 2H), 2.80-2.83 (m, 2H), 2.99-3.10 (m, 3H), 3.41 (td, J = 2, 11.6 Hz, 2H), 3.90 (dd, J = 2, 11.6 Hz, 2H), 4.34 (s, 1H), 6.47 (d, J = 3.6 Hz, 1H), 7.25 (d, J = 3.2 Hz, 1H), 7.45-7.51 (m, 2H), 8.64 (s, 1H), 9.45 (s, 1H).<br>HPLC: 99.60%<br>MS (ESI-MS): m/z calcd for, $C_{26}H_{32}F_3N_2O_4$ [MH]$^+$ 493.23, found 493.00 |

TABLE 2-continued

Analytical data

| Example | Structure | Data |
|---|---|---|
| 24 | 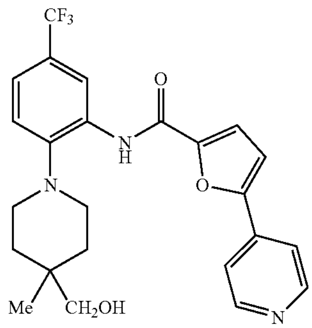 [SMILES: CC1(CO)CCN(c2ccc(C(F)(F)F)cc2NC(=O)c2ccc(-c3ccncc3)o2)CC1] | N-(2-(4-(hydroxymethyl)-4-methylpiperidin-1-yl)-5-(trifluoromethyl)phenyl)-5-(pyridin-4-yl)furan-2-carboxamide<br>$^1$H NMR (400 MHz, DMSO-d$_6$) δ 0.99 (s, 3H), 1.46-1.49 (m, 2H), 1.76-1.80 (m, 2H), 2.92-2.95 (m, 4H), 3.29 (d, J = 5.2 Hz, 2H), 4.69 (t, J = 5.2 Hz, 1H), 7.50-7.57 (m, 4H), 7.87 (dd, J = 1.6, 4.8 Hz, 2H), 8.60 (d, J = 1.6 Hz, 1H), 8.72 (dd, J = 1.6, 4.4 Hz, 2H), 9.63 (s, 1H).<br>HPLC purity: 98.90%<br>MS (ESI-MS): m/z calcd for C$_{24}$H$_{25}$F$_3$N$_3$O$_3$ [MH]$^+$ 460.18, found 460.19 |
| 25 | 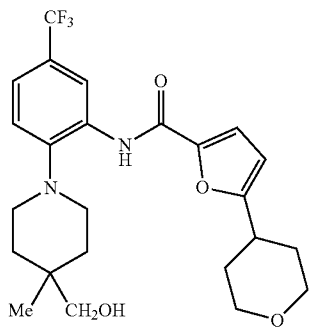 [SMILES: CC1(CO)CCN(c2ccc(C(F)(F)F)cc2NC(=O)c2ccc(C3CCOCC3)o2)CC1] | N-(2-(4-(hydroxymethyl)-4-methylpiperidin-1-yl)-5-(trifluoro methyl)phenyl)-5-(tetrahydro-2H-pyran-4-yl)furan-2-carboxamide<br>$^1$H NMR (400 MHz, DMSO-d$_6$) δ 0.99 (s, 3H), 1.45-1.48 (m, 2H), 1.65-1.77 (m, 4H), 1.95 (dd, J = 2, 12.8 Hz, 2H), 2.87-2.90 (m, 4H), 3.03-3.09 (m, 1H), 3.28 (d, J = 4.8 Hz, 2H), 3.47 (td, J = 2, 11.6 Hz, 2H), 3.92-3.96 (m, 2H), 4.62 (t, J = 4.8 Hz, 1H), 6.46 (dd, J = 0.8, 3.6 Hz, 1H), 7.25 (d, J = 3.6 Hz, 1H), 7.46 (dd, J = 1.6, 8.4 Hz, 1H), 7.52 (d, J = 8.4 Hz, 1H), 8.65 (d, J = 1.6 Hz, 1H), 9.40 (s, 1H).<br>HPLC purity: 98.01%<br>MS (ESI-MS): m/z calcd for C$_{24}$H$_{30}$F$_3$N$_2$O$_4$ [MH]$^+$ 467.22, found 467.11 |
| 26 | 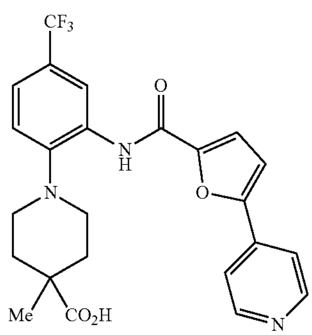 [SMILES: CC1(C(=O)O)CCN(c2ccc(C(F)(F)F)cc2NC(=O)c2ccc(-c3ccncc3)o2)CC1] | 4-methyl-1-(2-(5-(pyridin-4-yl)furan-2-carboxamido)-4-(trifluoromethyl)phenyl)-piperidine-4-carboxylic acid<br>$^1$H NMR (400 MHz, DMSO-d$_6$) δ 1.26 (s, 3H), 1.69-1.74 (m, 2H), 2.18-2.22 (m, 2H), 2.80-2.84 (m, 2H), 3.02-3.03 (m, 2H), 7.05-7.51 (m, 3H), 7.57 (d, J = 4 Hz, 1H), 7.85 (d, J = 6 Hz, 2H), 8.58 (s, 1H), 8.71 (d, J = 6 Hz, 2H), 9.68 (s, 1H), 12.50 (s, 1H).<br>HPLC purity: 100%<br>MS (ESI-MS): m/z calcd for C$_{24}$H$_{23}$F$_3$N$_3$O$_4$ [MH]$^+$ 474.16, found 474.12 |
| 27 | 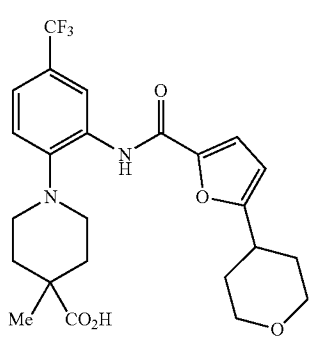 [SMILES: CC1(C(=O)O)CCN(c2ccc(C(F)(F)F)cc2NC(=O)c2ccc(C3CCOCC3)o2)CC1] | 4-methyl-1-(2-(5-(tetrahydro-2H-pyran-4-yl)furan-2-carboxamido)-4-(trifluoromethyl)phenyl)-piperidine-4-carboxylic acid<br>$^1$H NMR (400 MHz, DMSO-d$_6$) δ 1.25 (s, 3H), 1.63-1.76 (m, 4H), 1.92-1.95 (m, 2H), 2.19-2.22 (m, 2H), 2.78 (t, J = 9.6 Hz, 2H), 2.96-3.05 (m, 3H), 3.43-3.49 (m, 2H), 3.94 (d, J = 9.2 Hz, 2H), 6.47 (d, J = 3.2 Hz, 1H), 7.26 (d, J = 3.6 Hz, 1H), 7.45 (br s, 2H), 8.64 (s, 1H), 9.42 (s, 1H), 12.45 (br s, 1H).<br>HPLC purity: 95.73%<br>MS (ESI-MS): m/z calcd for C$_{24}$H$_{28}$F$_3$N$_2$O$_5$ [MH]$^+$ 481.20, found 481.13 |

TABLE 2-continued

Analytical data

| Example | Structure | Data |
|---|---|---|
| 28 | 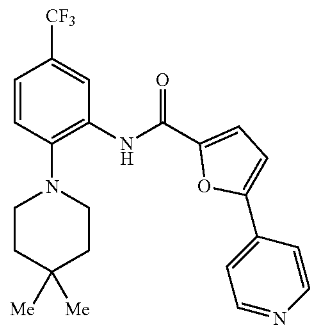 [SMILES: CC1(C)CCN(c2ccc(C(F)(F)F)cc2NC(=O)c2ccc(-c3ccncc3)o2)CC1] | N-(2-(4,4-dimethylpiperidin-1-yl)-5-(trifluoromethyl)phenyl)-5-(pyridin-4-yl)furan-2-carboxamide<br>$^1$H NMR (400 MHz, DMSO-d$_6$) δ 1.04 (s, 6H), 1.61 (t, J = 5.2 Hz, 4H), 2.92 (t, J = 5.2 Hz, 4H), 7.50-7.57 (m, 4H), 7.87 (dd, J = 1.6, 4.4 Hz, 2H), 8.57 (s, 1H), 8.71 (dd, J = 1.6, 4.8 Hz, 2H), 9.65 (s, 1H).<br>HPLC purity: 100%<br>MS (ESI-MS): m/z calcd for C$_{24}$H$_{25}$F$_3$N$_3$O$_2$ [MH]$^+$ 444.19, found 444.12 |
| 29 | 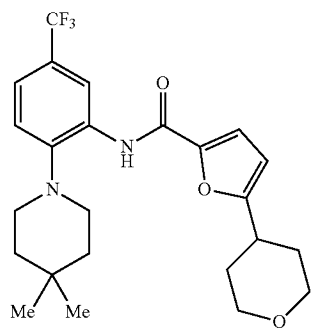 [SMILES: CC1(C)CCN(c2ccc(C(F)(F)F)cc2NC(=O)c2ccc(C3CCOCC3)o2)CC1] | N-(2-(4,4-dimethylpiperidin-1-yl)-5-(trifluoromethyl)phenyl)-5-(tetrahydro-2H-pyran-4-yl)furan-2-carboxamide<br>$^1$H NMR (400 MHz, CDCl$_3$) δ 1.09 (s, 6H), 1.66 (t, J = 5.2 Hz, 4H), 1.87-1.91 (m, 2H), 2.02-2.05 (m, 2H), 2.91 (t, J = 5.2 Hz, 4H), 2.98-3.02 (m, 1H), 3.56 (td, J = 2, 11.6 Hz, 2H), 4.10 (dd, J = 2.4, 12 Hz, 2H), 6.25 (d, J = 3.2 Hz, 1H), 7.21 (d, J = 3.2 Hz, 1H), 7.30-7.37 (m, 2H), 8.86 (s, 1H), 9.43 (br s, 1H).<br>HPLC purity: 99.41%<br>MS (ESI-MS): m/z calcd for C$_{24}$H$_{30}$F$_3$N$_2$O$_3$ [MH]$^+$ 451.22, found 451.13 |
| 30 | 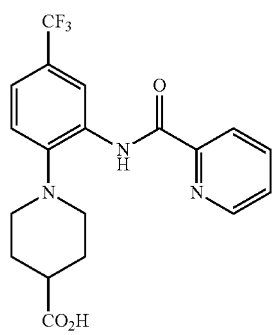 [SMILES: O=C(Nc1cc(C(F)(F)F)ccc1N1CCC(C(=O)O)CC1)c1ccccn1] | 1-(2-(picolinamido)-4-(trifluoromethyl)phenyl)-piperidine-4-carboxylic acid<br>$^1$H NMR (400 MHz, DMSO-d$_6$) δ 1.92-2.04 (m, 5H), 2.79-2.84 (m, 2H), 3.09-3.11 (m, 2H), 7.42 (J = 8.4 Hz, 1H), 7.47-7.49 (m, 1H), 7.72-7.75 (m, 1H), 7.73 (m, 1H), 8.22 (d, J = 8 Hz, 1H), 8.70 (d, J = 4 Hz, 1H), 8.80 (d, J = 1.2 Hz, 1H), 10.97 (s, 1H), 12.32 (s, 1H).<br>HPLC purity: 99.80%<br>MS (ESI-MS): m/z calcd for C$_{19}$H$_{19}$F$_3$N$_3$O$_3$ [MH]$^+$ 394.14, found 394.25 |
| 31 | 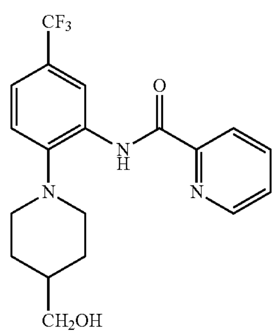 [SMILES: O=C(Nc1cc(C(F)(F)F)ccc1N1CCC(CO)CC1)c1ccccn1] | N-(2-(4-(hydroxymethyl)piperidin-1-yl)-5-(trifluoromethyl)phenyl)picolinamide<br>$^1$H NMR (400 MHz, DMSO-d$_6$) δ 1.53-1.56 (m, 3H), 1.84 (d, J = 9.2 Hz, 2H), 2.74 (t, J = 11.4 Hz, 2H), 3.10-3.13 (m, 2H), 3.40 (br s, 2H), 4.58 (t, J = 5.2 Hz, 1H), 7.42-7.49 (m, 2H), 7.72-7.75 (m, 1H), 8.13 (t, J = 7.2 Hz, 1H), 8.20-8.22 (m, 1H), 8.75 (d, J = 4 Hz, 1H), 8.80 (s, 1H), 11.00 (s, 1H).<br>HPLC purity: 100%<br>MS (ESI-MS): m/z calcd for C$_{19}$H$_{21}$F$_3$N$_3$O$_2$ [MH]$^+$ 380.15, found 380.22 |

TABLE 2-continued

Analytical data

| Example | Structure | Data |
|---|---|---|
| 32 | 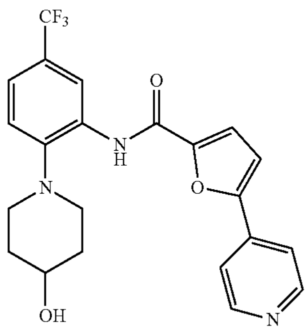 [SMILES: O=C(Nc1cc(C(F)(F)F)ccc1N1CCC(O)CC1)c1ccc(-c2ccncc2)o1] | N-(2-(4-hydroxypiperidin-1-yl)-5-(trifluoromethyl)-phenyl)-5-(pyridin-4-yl)furan-2-carboxamide<br>$^1$H NMR (400 MHz, DMSO-d$_6$) δ 1.73 (dd, J = 9.2, 18 Hz, 2H), 1.96-1.99 (m, 2H), 2.82 (t, J = 9.6 Hz, 2H), 3.07-3.10 (m, 2H), 3.74-375 (m, 1H), 4.89 (d, J = 2.8 Hz, 1H), 7.47-7.51 (m, 3H), 7.56 (d, J = 3.6 Hz, 1H), 7.88 (d, J = 5.6 Hz, 2H), 8.52 (s, 1H), 8.70 (d, J = 5.2 Hz, 2H), 9.83 (s, 1H).<br>HPLC purity: 100%<br>MS (ESI-MS): m/z calcd for C$_{22}$H$_{21}$F$_3$N$_3$O$_3$ [MH]$^+$ 432.15, found 432.20 |
| 33 | 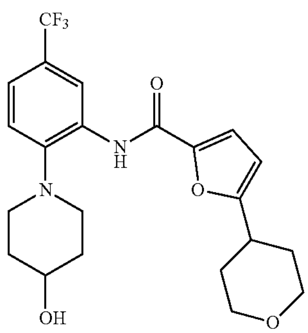 [SMILES: O=C(Nc1cc(C(F)(F)F)ccc1N1CCC(O)CC1)c1ccc(C2CCOCC2)o1] | N-(2-(4-hydroxypiperidin-1-yl)-5-(trifluoromethyl)-phenyl)-5-(tetrahydro-2H-pyran-4-yl)furan-2-carboxamide<br>$^1$H NMR (400 MHz, DMSO-d$_6$) δ 1.64-1.76 (m, 4H), 1.95-1.98 (m, 4H), 2.78 (t, J = 9.2 Hz, 2H), 3.02-3.08 (m, 3H), 3.47 (dd, J = 9.2, 11.6 Hz, 2H), 3.71-3.72 (m, 1H), 3.93 (d, J = 10 Hz, 2H), 4.81 (d, J = 3.2 Hz, 1H), 6.46 (d, J = 3.2 Hz, 1H), 7.26 (d, J = 3.6 Hz, 1H), 7.45 (br s, 2H), 8.57 (s, 1H), 9.49 (s, 1H).<br>HPLC purity: 99.63%<br>MS (ESI-MS): m/z calcd for C$_{22}$H$_{26}$F$_3$N$_2$O$_4$ [MH]$^+$ 439.18, found 439.17 |
| 34 | 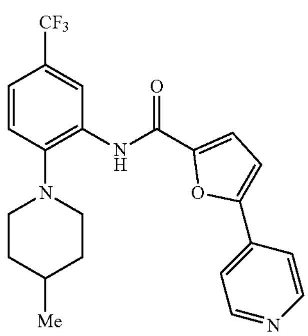 [SMILES: CC1CCN(c2ccc(C(F)(F)F)cc2NC(=O)c2ccc(-c3ccncc3)o2)CC1] | N-(2-(4-methylpiperidin-1-yl)-5-(trifluoromethyl)-phenyl)-5-(pyridin-4-yl)furan-2-carboxamide<br>$^1$H NMR (400 MHz, DMSO-d$_6$) δ 1.00 (d, J = 6.4 Hz, 3H), 1.42-1.51 (m, 2H), 1.54-1.59 (m, 1H), 1.79-1.82 (m, 2H), 2.73-2.78 (m, 2H), 3.07-3.10 (m, 2H), 7.45-7.52 (m, 3H), 7.57 (d, J = 3.6 Hz, 1H), 7.87 (dd, J = 1.6, 4.8 Hz, 2H), 8.56 (d, J = 1.6 Hz, 1H), 8.71 (dd, J = 1.6, 4.4 Hz, 2H), 9.69 (s, 1H).<br>HPLC purity: 98.07%<br>MS (ESI-MS): m/z calcd for C$_{23}$H$_{23}$F$_3$N$_3$O$_2$ [MH]$^+$ 430.17, found 430.27 |
| 35 | 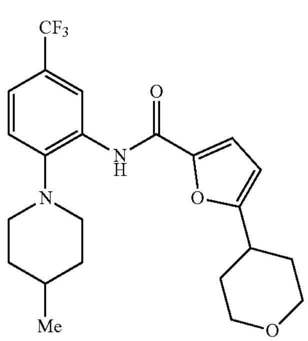 [SMILES: CC1CCN(c2ccc(C(F)(F)F)cc2NC(=O)c2ccc(C3CCOCC3)o2)CC1] | N-(2-(4-methylpiperidin-1-yl)-5-(trifluoromethyl)-phenyl)-5-(tetrahydro-2H-pyran-4-yl)furan-2-carboxamide<br>$^1$H NMR (400 MHz, DMSO-d$_6$) δ 1.01 (d, J = 6.4 Hz, 3H), 1.40-1.47 (m, 2H), 1.55-1.60 (m, 1H), 1.69-1.84 (m, 4H), 1.93 (dd, J = 2, 12.8 Hz, 2H), 2.75 (dd, J = 9.6, 11.6 Hz, 2H), 3.00-3.09 (m, 3H), 3.46 (td, J = 2, 11.6 Hz, 2H), 3.93-3.96 (m, 2H), 6.47 (d, J = 0.8, 3.6 Hz, 1H), 7.25 (d, J = 3.2 Hz, 1H), 7.46 (d, J = 1.2 Hz, 2H), 8.64 (s, 1H), 9.46 (s, 1H).<br>HPLC purity: 97.81%<br>MS (ESI-MS): m/z calcd for C$_{23}$H$_{28}$F$_3$N$_2$O$_3$ [MH]$^+$ 437.21, found 437.06 |

TABLE 2-continued

Analytical data

| Example | Structure | Data |
|---|---|---|
| 36 | 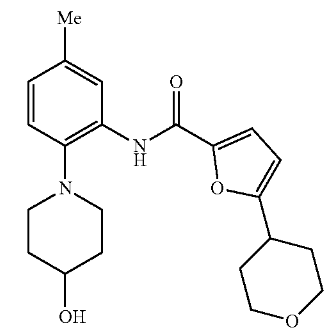 | N-(2-(4-hydroxypiperidin-1-yl)-5-methylphenyl)-5-(tetrahydro-2H-pyran-4-yl)furan-2-carboxamide<br>$^1$H NMR (400 MHz, DMSO-d$_6$) δ 1.63-1.75 (m, 4H), 1.91-1.99 (m, 4H), 2.28 (s, 3H), 2.67-2.72 (m, 2H), 2.88-2.91 (m, 2H), 3.00-3.08 (m, 1H), 3.46 (td, J = 2, 11.6 Hz, 2H), 3.68-3.69 (m, 1H), 3.91-3.94 (m, 2H), 4.76 (d, J = 3.2 Hz, 1H), 6.43 (dd, J = 0.8, 3.2 Hz, 1H), 6.90 (dd, J = 1.2, 8 Hz, 1H), 7.16-7.18 (m, 2H), 8.13 (d, J = 1.6 Hz, 1H), 9.61 (s, 1H).<br>HPLC purity: 99.00%<br>MS (ESI-MS): m/z calcd for C$_{22}$H$_{29}$N$_2$O$_4$ [MH]$^+$ 485.21, found 485.18 |
| 37 | 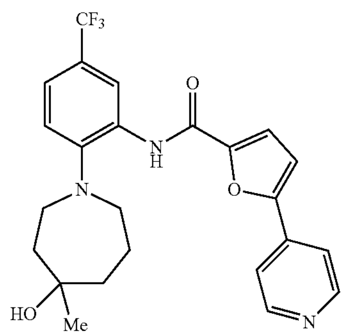 [SMILES: CC1(O)CCCN(c2ccc(C(F)(F)F)cc2NC(=O)c2ccc(-c3ccncc3)o2)CC1] | N-(2-(4-hydroxy-4-methylazepan-1-yl)-5-(trifluoromethyl)phenyl)-5-(pyridin-4-yl)furan-2-carboxamide<br>$^1$H NMR (400 MHz, DMSO-d$_6$) δ 1.11 (s, 3H), 1.63-1.77 (m, 4H), 1.89-1.95 (m, 1H), 2.00-2.02 (m, 1H), 2.99-3.13 (m, 2H), 3.19-3.32 (m, 2H), 4.30 (s, 1H), 7.31 (d, J = 8.8 Hz, 1H), 7.46-7.53 (m, 3H), 7.92 (d, J = 6 Hz, 2H), 8.06 (s, 1H), 8.68-8.70 (m, 2H), 9.92 (s, 1H).<br>HPLC purity: 99.67%<br>MS (ESI-MS): m/z calcd for C$_{24}$H$_{25}$F$_3$N$_3$O$_3$ [MH]$^+$ 460.18, found 460.19 |
| 38 | 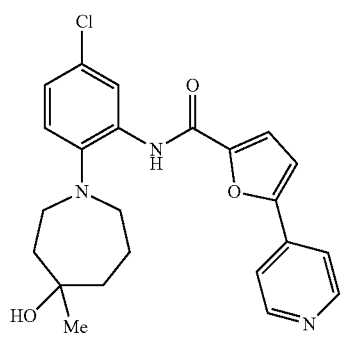 | N-(5-chloro-2-(4-hydroxy-4-methylazepan-1-yl)phenyl)-5-(pyridin-4-yl)furan-2-carboxamide<br>$^1$H NMR (400 MHz, DMSO-d$_6$) δ 1.16 (s, 3H), 1.60-1.64 (m, 1H), 1.74-1.80 (m, 2H), 1.84-1.96 (m, 3H), 2.83-2.88 (m, 1H), 2.95 (td, J = 3.2, 8.8 Hz, 1H), 3.00-3.11 (m, 1H), 3.12-3.15 (m, 1H), 4.38 (s, 1H), 7.18 (dd, J = 2.4, 8.4 Hz, 1H), 7.31 (d, J = 8.4 Hz, 1H), 7.48 (d, J = 3.6 Hz, 1H), 7.55 (d, J = 3.6 Hz, 1H), 7.89 (dd, J = 1.6, 4.4 Hz, 2H), 8.16 (d, J = 2.4 Hz, 1H), 8.69-8.70 (m, 2H), 9.84 (s, 1H).<br>HPLC purity: 100%<br>MS (ESI-MS): m/z calcd for C$_{23}$H$_{25}$$^{35}$ClN$_3$O$_3$ [MH]$^+$ 426.16, found 425.99 |
| 39 | 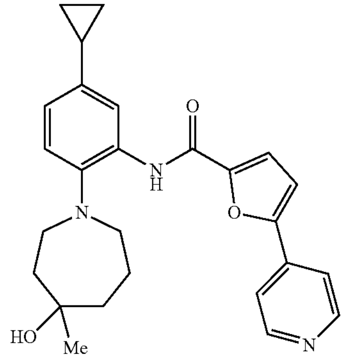 [SMILES: CC1(O)CCCN(c2ccc(C3CC3)cc2NC(=O)c2ccc(-c3ccncc3)o2)CC1] | N-(5-cyclopropyl-2-(4-hydroxy-4-methylazepan-1-yl)phenyl)-5-(pyridin-4-yl)-furan-2-carboxamide<br>$^1$H NMR (400 MHz, DMSO-d$_6$) δ 0.60-0.64 (m, 2H), 0.91-0.96 (m, 2H), 1.16 (s, 3H), 1.60-1.62 (m, 1H), 1.80 (t, J = 4.8 Hz, 2H), 1.84-1.98 (m, 4H), 2.80-2.85 (m, 1H), 2.88-2.92 (m, 1H), 2.96-3.00 (m, 1H), 3.05-3.10 (m, 1H), 4.36 (s, 1H), 6.84 (dd, J = 2, 8 Hz, 1H), 7.18 (d, J = 8 Hz, 1H), 7.43 (d, J = 4 Hz, 1H), 7.54 (d, J = 3.6 Hz, 1H), 7.88 (d, J = 6 Hz, 2H), 7.93 (d, J = 1.6 Hz, 1H), 8.69 (d, J = 6 Hz, 2H), 9.81 (s, 1H).<br>HPLC purity: 98.84%<br>MS (ESI-MS): m/z calcd for C$_{26}$H$_{30}$F$_3$N$_3$O$_3$ [MH]$^+$ 432.23, found 432.15 |

| Example | Structure | Data |
| --- | --- | --- |
| 40 | 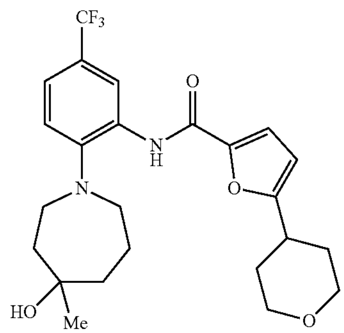 [SMILES: CC1(O)CCCN(c2ccc(C(F)(F)F)cc2NC(=O)c2ccc(C3CCOCC3)o2)CC1] | N-(2-(4-hydroxy-4-methylazepan-1-yl)-5-(trifluoromethyl)phenyl)-5-(tetrahydro-2H-pyran-4-yl)furan-2-carboxamide<br>$^1$H NMR (400 MHz, DMSO-d$_6$) δ 1.19 (s, 3H), 1.59-1.68 (m, 3H), 1.71-1.90 (m, 4H), 1.93-1.96 (m, 3H), 2.89-2.93 (m, 1H), 3.00-3.10 (m, 3H), 3.22-3.27 (m, 1H), 3.42-3.51 (m, 3H), 3.93 (dd, J = 2, 11.6 Hz, 2H), 4.32 (s, 1H), 6.44 (d, J = 2.8 Hz, 1H), 7.24 (d, J = 3.6 Hz, 1H), 7.39 (d, J = 8.8 Hz, 1H), 7.44 (dd, J = 1.6, 8.4 Hz, 1H), 8.35 (d, J = 1.6 Hz, 1H), 9.56 (s, 1H).<br>HPLC purity: 100%<br>MS (ESI-MS): m/z calcd for C$_{24}$H$_{30}$F$_3$N$_2$O$_4$ [MH]$^+$ 467.22, found 467.11 |
| 41 | 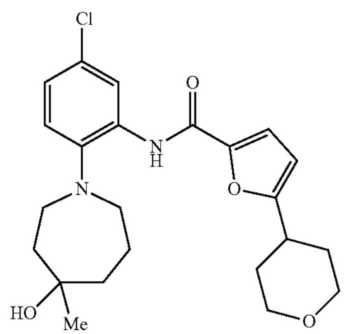 [SMILES: CC1(O)CCCN(c2ccc(Cl)cc2NC(=O)c2ccc(C3CCOCC3)o2)CC1] | N-(5-chloro-2-(4-hydroxy-4-methylazepan-1-yl)phenyl)-5-(tetrahydro-2H-pyran-4-yl)furan-2-carboxamide<br>$^1$H NMR (400 MHz, DMSO-d$_6$) δ 1.20 (s, 3H), 1.61-1.74 (m, 3H), 1.80-1.85 (m, 4H), 1.93-1.96 (m, 3H), 2.75-2.79 (m, 1H), 2.93 (t, J = 5.6 Hz, 2H), 3.01-3.08 (m, 1H), 3.12-3.15 (m, 1H), 3.41-3.47 (m, 2H), 3.92-3.94 (m, 2H), 4.33 (s, 1H), 6.45 (d, J = 3.6 Hz, 1H), 7.14 (dd, J = 2.4, 8.4 Hz, 1H), 7.24 (d, J = 3.2 Hz, 1H), 7.32 (d, J = 8.4 Hz, 1H), 8.30 (d, J = 2.4 Hz, 1H), 9.61 (s, 1H).<br>HPLC purity: 100%<br>MS (ESI-MS): m/z calcd for C$_{23}$H$_{30}$$^{35}$ClN$_2$O$_4$ [MH]$^+$ 433.19, found 433.15 |
| 42 | 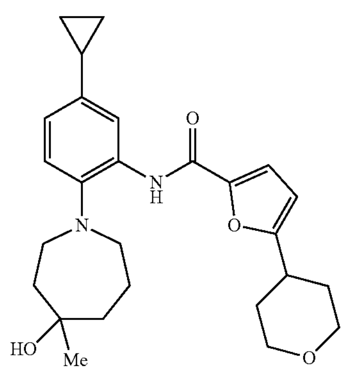 [SMILES: CC1(O)CCCN(c2ccc(C3CC3)cc2NC(=O)c2ccc(C3CCOCC3)o2)CC1] | N-(5-cyclopropyl-2-(4-hydroxy-4-methylazepan-1-yl)phenyl)-5-(tetrahydro-2H-pyran-4-yl)furan-2-carboxamide<br>$^1$H NMR (400 MHz, DMSO-d$_6$) δ 0.58-0.62 (m, 2H), 0.90-0.95 (m, 2H), 1.20 (s, 3H), 1.60-1.73 (m, 3H), 1.80-1.96 (m, 8H), 2.71-2.75 (m, 1H), 2.88-2.90 (m, 2H), 3.03-3.11 (m, 2H), 3.44 (td, J = 1.6, 11.6 Hz, 2H), 3.93 (dd, J = 2, 11.6 Hz, 2H), 4.30 (s, 1H), 6.43 (dd, J = 0.8, 3.6 Hz, 1H), 6.80 (dd, J = 2, 8 Hz, 1H), 7.16-7.20 (m, 2H), 8.04 (d, J = 2 Hz, 1H), 9.57 (s, 1H).<br>HPLC purity: 100%<br>MS (ESI-MS): m/z calcd for C$_{26}$H$_{35}$N$_2$O$_4$ [MH]$^+$ 439.26, found 439.16 |
| 43 | 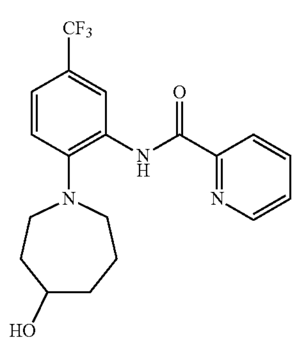 [SMILES: O=C(Nc1cc(C(F)(F)F)ccc1N1CCCC(O)CC1)c1ccccn1] | N-(2-(4-hydroxyazepan-1-yl)-5-(trifluoromethyl)phenyl)picolinamide<br>$^1$H NMR (400 MHz, DMSO-d$_6$) δ 1.69-1.72 (m, 1H), 1.78-1.84 (m, 1H), 1.87-1.91 (m, 2H), 2.03-2.07 (m, 2H), 2.99-3.06 (m, 3H), 3.11-3.16 (m, 1H), 3.99-4.02 (m, 1H), 4.63 (d, J = 3.6 Hz, 1H), 7.46 (br s, 2H), 7.72-7.75 (m, 1H), 8.11-8.14 (m, 1H), 8.21 (d, J = 7.6 Hz, 1H), 8.74-8.76 (m, 2H), 11.13 (s, 1H).<br>HPLC purity: 98.05%<br>MS (ESI-MS): m/z calcd for C$_{19}$H$_{21}$F$_3$N$_3$O$_2$ [MH]$^+$ 380.15, found 380.25 |

TABLE 2-continued

Analytical data

| Example | Structure | Data |
|---|---|---|
| 44 | 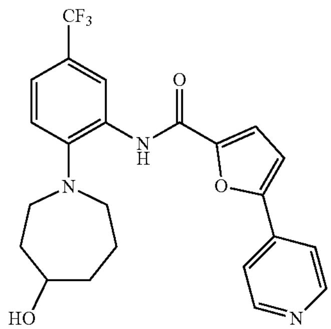 [SMILES: O=C(Nc1cc(C(F)(F)F)ccc1N1CCCC(O)CC1)c1ccc(-c2ccncc2)o1] | N-(2-(4-hydroxyazepan-1-yl)-5-(trifluoromethyl)-phenyl)-5-(pyridin-4-yl)furan-2-carboxamide<br>$^1$H NMR (400 MHz, DMSO-d$_6$) δ 1.67-1.73 (m, 2H), 1.76-1.82 (m, 1H), 1.86-1.91 (m, 2H), 2.00-2.05 (m, 1H), 3.09-3.17 (m, 3H), 3.24-3.28 (m, 1H), 3.85-3.86 (m, 1H), 4.60 (d, J = 3.6 Hz, 1H), 7.33 (d, J = 8.4 Hz, 1H), 7.46-7.50 (m, 2H), 7.53 (d, J = 4 Hz, 1H), 7.89-7.91 (m, 2H), 8.06 (d, J = 1.6 Hz, 1H), 8.70 (dd, J = 1.6, 4.8 Hz, 2H), 9.92 (s, 1H).<br>HPLC purity: 99.63%<br>MS (ESI-MS): m/z calcd for C$_{23}$H$_{28}$F$_3$N$_2$O$_4$ [MH]$^+$ 446.17, found 446.02 |
| 45 | 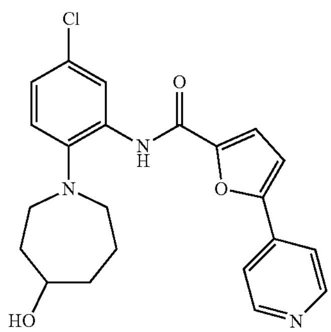 [SMILES: O=C(Nc1cc(Cl)ccc1N1CCCC(O)CC1)c1ccc(-c2ccncc2)o1] | N-(5-chloro-2-(4-hydroxyazepan-1-yl)phenyl)-5-(pyridin-4-yl)furan-2-carboxamide<br>$^1$H NMR (400 MHz, DMSO-d$_6$) δ 1.68-2.08 (m, 6H), 2.97-3.05 (m, 4H), 3.94 (br s, 1H), 4.66 (d, J = 3.2 Hz, 1H), 7.18 (dd, J = 2, 8.8 Hz, 1H), 7.31 (d, J = 8.8 Hz, 1H), 7.49 (d, J = 3.6 Hz, 1H), 7.55 (d, J = 3.6 Hz, 1H), 7.87 (d, J =5.6 Hz, 2H), 8.19 (d, J = 2 Hz, 1H), 8.70 (d, J = 5.6 Hz, 2H), 9.82 (s, 1H).<br>HPLC purity: 100%<br>MS (ESI-MS): m/z calcd for C$_{22}$H$_{23}$$^{35}$ClN$_3$O$_3$ [MH]$^+$ 412.14, found 412.07 |
| 46 | 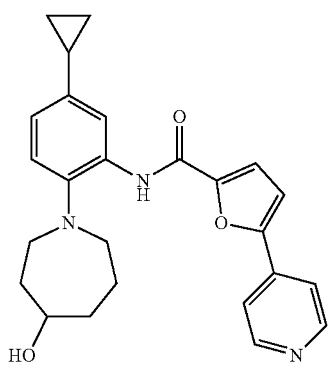 [SMILES: O=C(Nc1cc(C2CC2)ccc1N1CCCC(O)CC1)c1ccc(-c2ccncc2)o1] | N-(5-cyclopropyl-2-(4-hydroxyazepan-1-yl)phenyl)-5-(pyridin-4-yl)furan-2-carboxamide<br>$^1$H NMR (400 MHz, DMSO-d$_6$) δ 0.60-0.63 (m, 2H), 0.92-0.96 (m, 2H), 1.65-1.69 (m, 1H), 1.74-1.84 (m, 2H), 1.86-1.96 (m, 3H), 2.06-2.10 (m, 1H), 2.88-3.05 (m, 4H), 3.93-3.96 (m, 1H), 4.64 (d, J = 3.2 Hz, 1H), 6.85 (dd, J = 2, 8 Hz, 1H), 7.18 (d, J = 8 Hz, 1H), 7.43 (d, J = 3.6 Hz, 1H), 7.54 (d, J = 3.6 Hz, 1H), 7.86 (d, J = 5.6 Hz, 2H), 7.96 (s, 1H), 8.70 (d, J = 6 Hz, 2H), 9.78 (s, 1H).<br>HPLC purity: 98.57%<br>MS (ESI-MS): m/z calcd for C$_{25}$H$_{28}$N$_3$O$_3$ [MH]$^+$ 418.21, found 418.08 |
| 47 | 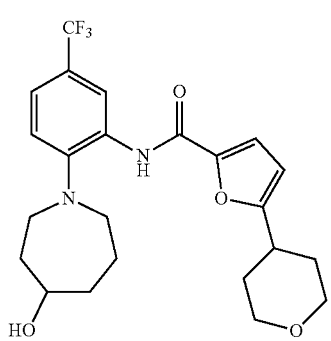 [SMILES: O=C(Nc1cc(C(F)(F)F)ccc1N1CCCC(O)CC1)c1ccc(C2CCOCC2)o1] | N-(2-(4-hydroxyazepan-1-yl)-5-(trifluoromethyl)-phenyl)-5-(tetrahydro-2H-pyran-4-yl)furan-2-carboxamide<br>$^1$H NMR (400 MHz, DMSO-d$_6$) δ 1.63-1.79 (m, 5H), 1.91-2.03 (m, 5H), 2.99-3.06 (m, 4H), 3.08-3.17 (m, 1H), 3.46 (td, J = 2, 11.6 Hz, 2H), 3.88-3.94 (m, 3H), 4.60 (d, J = 3.6 Hz, 1H), 6.44 (d, J = 3.2 Hz, 1H), 7.25 (d, J = 3.2 Hz, 1H), 7.40 (d, J = 8.4 Hz, 1H), 7.45 (dd, J = 2, 8.4 Hz, 1H), 8.37 (d, J = 2 Hz, 1H), 9.62 (s, 1H).<br>HPLC purity: 97.36%<br>MS (ESI-MS): m/z calcd for C$_{23}$H$_{28}$F$_3$N$_2$O$_4$ [MH]$^+$ 453.20, found 453.03 |

TABLE 2-continued

Analytical data

| Example | Structure | Data |
|---|---|---|
| 48 | 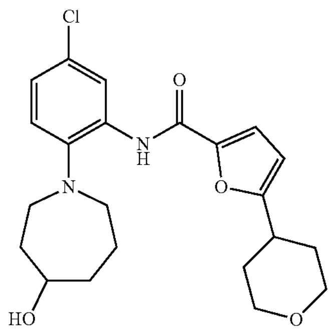 [SMILES: O=C(Nc1cc(Cl)ccc1N1CCCC(O)CC1)c1ccc(C2CCOCC2)o1] | N-(5-chloro-2-(4-hydroxyazepan-1-yl)phenyl)-5-(tetrahydro-2H-pyran-4-yl)furan-2-carboxamide<br>$^1$H NMR (400 MHz, DMSO-$d_6$) δ 1.63-1.80 (m, 5H), 1.87-2.04 (m, 5H), 2.88-3.07 (m, 5H), 3.46 (td, J = 2, 11.6 Hz, 2H), 3.91-3.94 (m, 3H), 4.60 (d, J = 3.6 Hz, 1H), 6.44 (dd, J = 0.8, 3.6 Hz, 1H), 7.14 (dd, J = 2.4, 8.4 Hz, 1H), 7.24 (d, J = 3.6 Hz, 1H), 7.32 (d, J = 8.4 Hz, 1H), 8.31 (d, J = 2.4 Hz, 1H), 9.67 (br s, 1H).<br>HPLC purity: 98.89%<br>MS (ESI-MS): m/z calcd for $C_{22}H_{28}{}^{35}ClN_2O_4$ [MH]$^+$ 419.17, found 419.18 |
| 49 | 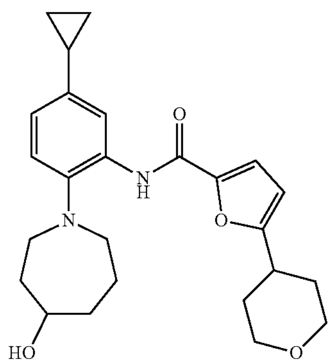 [SMILES: O=C(Nc1cc(C2CC2)ccc1N1CCCC(O)CC1)c1ccc(C2CCOCC2)o1] | N-(5-cyclopropyl-2-(4-hydroxyazepan-1-yl)phenyl)-5-(tetrahydro-2H-pyran-4-yl)furan-2-carboxamide<br>$^1$H NMR (400 MHz, DMSO-$d_6$) δ 0.59-0.62 (m, 2H), 0.91-0.95 (m, 2H), 1.64-1.85 (m, 5H), 1.86-1.99 (m, 6H), 2.87-3.06 (m, 5H), 3.46 (td, J = 2, 11.6 Hz, 2H), 3.91-3.94 (m, 3H), 4.57 (d, J = 3.6 Hz, 1H), 6.42 (dd, J = 0.8, 3.6 Hz, 1H), 6.80 (dd, J = 2, 8.4 Hz, 1H), 7.15-7.17 (m, 2H), 8.05 (d, J = 2 Hz, 1H), 9.67 (s, 1H).<br>HPLC purity: 98.21%<br>MS (ESI-MS): m/z calcd for $C_{25}H_{33}N_2O_4$ [MH]$^+$ 425.24, found 425.14 |
| 50 | 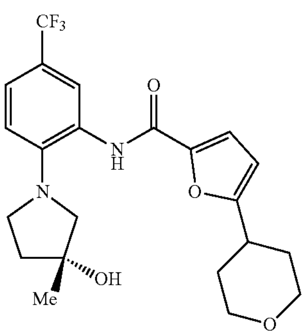 [SMILES: C[C@@]1(O)CCN(c2ccc(C(F)(F)F)cc2NC(=O)c2ccc(C3CCOCC3)o2)C1] | (R)-N-(2-(3-hydroxy-3-methylpyrrolidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 1.27 (s, 3H), 1.63-1.85 (m, 4H), 1.89-1.92 (m, 2H), 2.96-3.02 (m, 1H), 3.20-3.23 (m, 1H), 3.33-3.41 (m, 2H), 3.42-3.48 (m, 2H), 3.52-3.59 (m, 1H), 3.90-3.93 (m, 2H), 4.79 (s, 1H), 6.36 (d, J = 2.8 Hz, 1H), 6.84 (d, J = 8.4 Hz, 1H), 7.20 (d, J = 3.2 Hz, 1H), 7.39-7.41 (m, 2H), 9.80 (s, 1H).<br>HPLC purity: 99.96%<br>MS (ESI-MS): m/z calcd for $C_{22}H_{26}F_3N_2O_4$ [MH]$^+$ 439.18, found 439.21 |
| 51 | 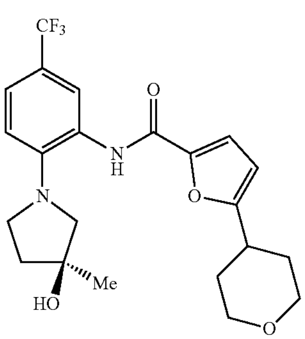 [SMILES: C[C@]1(O)CCN(c2ccc(C(F)(F)F)cc2NC(=O)c2ccc(C3CCOCC3)o2)C1] | (S)-N-(2-(3-hydroxy-3-methylpyrrolidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 1.27 (s, 3H), 1.64-1.85 (m, 4H), 1.89-1.92 (m, 2H), 2.96-3.02 (m, 1H), 3.21-3.23 (m, 1H), 3.37-3.39 (m, 2H), 3.42-3.47 (m, 2H), 3.52-3.56 (m, 1H), 3.90-3.92 (m, 2H), 4.78 (s, 1H), 6.36 (d, J = 3.2 Hz, 1H), 6.84 (d, J = 9.2 Hz, 1H), 7.20 (d, J = 3.2 Hz, 1H), 7.39-7.41 (m, 2H), 9.79 (s, 1H).<br>HPLC purity: 99.15%<br>MS (ESI-MS): m/z calcd for $C_{22}H_{26}F_3N_2O_4$ [MH]$^+$ 439.18, found 439.21 |

TABLE 2-continued

Analytical data

| Example | Structure | Data |
|---|---|---|
| 52 | 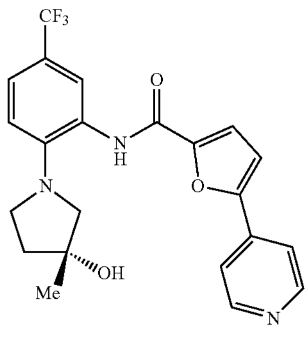 [SMILES: C[C@@]1(O)CCN(c2ccc(C(F)(F)F)cc2NC(=O)c2ccc(-c3ccncc3)o2)C1] | (R)-N-(2-(3-hydroxy-3-methylpyrrolidin-1-yl)-5-(trifluoromethyl)phenyl)-5-(pyridin-4-yl)furan-2-carboxamide<br>$^1$H NMR (400 MHz, DMSO-$d_6$) δ 1.26 (s, 3H), 1.78-1.85 (m, 2H), 3.25-3.27 (m, 1H), 3.37-4.00 (m, 2H), 3.56-3.60 (m, 1H), 4.79 (s, 1H), 6.83 (d, J = 8.4 Hz, 1H), 7.43-7.49 (m, 4H), 7.93 (d, J = 4.8 Hz, 2H), 8.69 (d, J = 4 Hz, 2H), 10.22 (s, 1H).<br>HPLC purity: 98.77%<br>MS (ESI-MS): m/z calcd for $C_{22}H_{21}F_3N_3O_3$ [MH]$^+$ 432.15, found 432.17 |
| 53 | 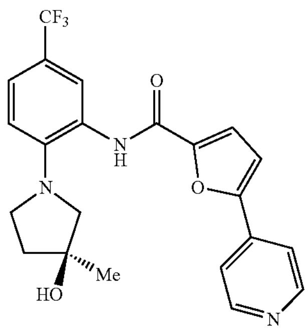 [SMILES: C[C@]1(O)CCN(c2ccc(C(F)(F)F)cc2NC(=O)c2ccc(-c3ccncc3)o2)C1] | (S)-N-(2-(3-hydroxy-3-methylpyrrolidin-1-yl)-5-(trifluoromethyl)phenyl)-5-(pyridin-4-yl)furan-2-carboxamide<br>$^1$H NMR (400 MHz, DMSO-$d_6$) δ 1.26 (s, 3H), 1.77-1.86 (m, 2H), 3.25-3.27 (m, 1H), 3.37-4.10 (m, 2H), 3.59-3.60 (m, 1H), 4.79 (s, 1H), 6.86 (d, J = 8.4 Hz, 1H), 7.41-7.45 (m, 3H), 7.49 (d, J = 3.6 Hz, 1H), 7.93 (d, J = 6 Hz, 2H), 8.69 (dd, J = 1.6, 4.8 Hz, 2H), 10.22 (s, 1H).<br>HPLC purity: 95.02%<br>MS (ESI-MS): m/z calcd for $C_{22}H_{21}F_3N_3O_3$ [MH]$^+$ 432.15, found 432.05 |
| 54 | 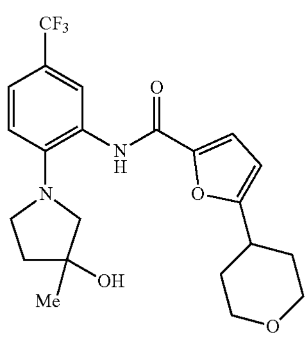 [SMILES: CC1(O)CCN(c2ccc(C(F)(F)F)cc2NC(=O)c2ccc(C3CCOCC3)o2)C1] | N-(2-(3-hydroxy-3-methylpyrrolidin-1-yl)-5-(trifluoromethyl)-phenyl)-5-(tetrahydro-2H-pyran-4-yl)furan-2-carboxamide<br>$^1$H NMR (400 MHz, DMSO-$d_6$) δ 1.27 (s, 3H), 1.63-1.73 (m, 2H), 1.77-1.92 (m, 4H), 2.96-3.02 (m, 1H), 3.22 (d, J = 10 Hz, 1H), 3.32-3.34 (m, 2H), 3.45 (t, J = 10 Hz, 2H), 3.52-3.59 (m, 1H), 3.91 (d, J = 10.4 Hz, 2H), 4.78 (s, 1H), 6.36 (d, J = 2.8 Hz, 1H), 6.84 (d, J = 9.6 Hz, 1H), 7.20 (d, J = 3.2 Hz, 1H), 7.39-7.41 (m, 2H), 9.78 (s, 1H).<br>HPLC purity: 95.10%<br>MS (ESI-MS): m/z calcd for $C_{22}H_{26}F_3N_2O_4$ [MH]$^+$ 439.18, found 439.06 |
| 55 | 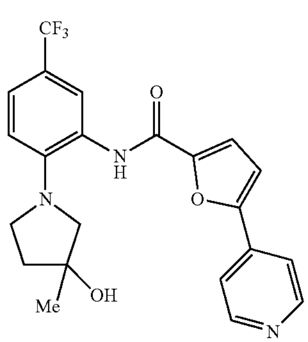 [SMILES: CC1(O)CCN(c2ccc(C(F)(F)F)cc2NC(=O)c2ccc(-c3ccncc3)o2)C1] | N-(2-(3-hydroxy-3-methylpyrrolidin-1-yl)-5-(trifluoromethyl)-phenyl)-5-(pyridin-4-yl)furan-2-carboxamide<br>$^1$H NMR (400 MHz, DMSO-$d_6$) δ 1.26 (s, 3H), 1.75-1.86 (m, 2H), 3.26 (d, J = 10 Hz, 1H), 3.39 (d, J = 9.6 Hz, 2H), 3.56-3.62 (m, 1H), 4.79 (s, 1H), 6.86 (d, J = 8.4 Hz, 1H), 7.40-7.49 (m, 4H), 7.92 (d, J = 5.6 Hz, 2H), 8.68 (d, J = 6 Hz, 2H), 10.21 (s, 1H).<br>HPLC purity: 99.83%<br>MS (ESI-MS): m/z calcd for $C_{22}H_{21}F_3N_3O_3$ [MH]$^+$ 432.15, found 432.00 |

TABLE 2-continued

| Example | Structure | Data |
|---|---|---|
| 56 | 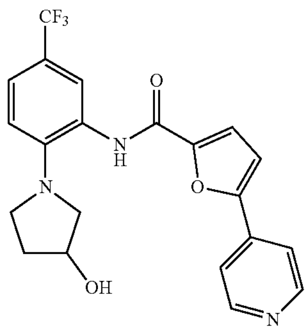 [SMILES: O=C(Nc1cc(C(F)(F)F)ccc1N1CCC(O)C1)c1ccc(-c2ccncc2)o1] | N-(2-(3-hydroxypyrrolidin-1-yl)-5-(trifluoromethyl)-phenyl)-5-(pyridin-4-yl)furan-2-carboxamide<br>$^1$H NMR (400 MHz, DMSO-d$_6$) δ 1.82-1.83 (m, 1H), 1.89-1.93 (m, 1H), 3.18 (d, J = 9.6 Hz, 1H), 3.35-3.39 (m, 1H), 3.50-3.60 (m, 2H), 4.29 (br s, 1H), 4.63 (br s, 1H), 6.90 (d, J = 8.8 Hz, 1H), 7.42 (s, 1H), 7.46 (d, J = 8.8 Hz, 1H), 7.54 (d, J = 3.6 Hz, 1H), 7.96 (d, J = 3.6 Hz, 1H), 8.54 (d, J = 6.8 Hz, 2H), 9.01 (d, J = 6.8 Hz, 2H), 10.56 (s, 1H).<br>HPLC purity: 98.74%<br>MS (ESI-MS): m/z calcd for C$_{21}$H$_{19}$F$_3$N$_3$O$_3$ [MH]$^+$ 418.14, found 418.13 |
| 57 | 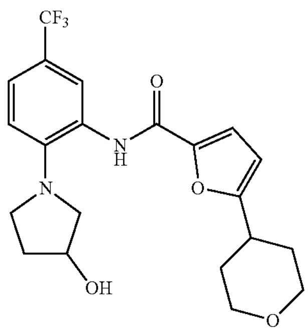 [SMILES: O=C(Nc1cc(C(F)(F)F)ccc1N1CCC(O)C1)c1ccc(C2CCOCC2)o1] | N-(2-(3-hydroxypyrrolidin-1-yl)-5-(trifluoromethyl)-phenyl)-5-(tetrahydro-2H-pyran-4-yl)furan-2-carboxamide<br>$^1$H NMR (400 MHz, DMSO-d$_6$) δ 1.65-1.72 (m, 2H), 1.82-1.83 (m, 1H), 1.90-1.93 (m, 3H), 2.97-2.99 (m, 1H), 3.15 (d, J = 10.4 Hz, 1H), 3.00-3.33 (m, 1H), 3.41-3.50 (m, 3H), 3.56 (dd, J = 4.8, 10.4 Hz, 1H), 3.89-3.92 (m, 2H), 4.29 (br s, 1H), 4.96 (d, J = 3.6 Hz, 1H), 6.35 (d, J = 2.8 Hz, 1H), 6.87 (d, J = 8.8 Hz, 1H), 7.21 (d, J = 3.6 Hz, 1H), 7.38-7.42 (m, 2H), 9.83 (s, 1H).<br>HPLC purity: 95.21%<br>MS (ESI-MS): m/z calcd for C$_{21}$H$_{24}$F$_3$N$_2$O$_4$ [MH]$^+$ 425.17, found 425.19 |
| 58 | 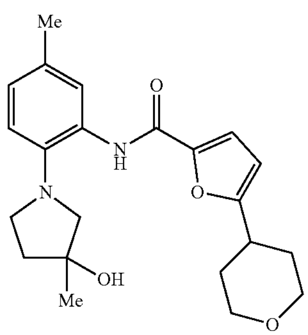 | N-(2-(3-hydroxy-3-methylpyrrolidin-1-yl)-5-methylphenyl)-5-(tetrahydro-2H-pyran-4-yl)-furan-2-carboxamide<br>$^1$H NMR (400 MHz, DMSO-d$_6$) δ 1.31 (s, 3H), 1.63-1.72 (m, 2H), 1.80-1.93 (m, 4H), 2.23 (s, 3H), 2.96-3.02 (m, 2H), 3.10-3.15 (m, 2H), 3.27-3.32 (m, 2H), 3.44 (td, J = 2, 11.2 Hz, 2H), 3.92-3.93 (m, 2H), 4.75 (s, 1H), 6.36 (d, J = 2.8 Hz, 1H), 6.86-6.92 (m, 2H), 7.19 (d, J = 3.2 Hz, 1H), 7.42 (s, 1H), 9.43 (s, 1H).<br>HPLC purity: 98.49%<br>MS (ESI-MS): m/z calcd for C$_{22}$H$_{29}$N$_2$O$_4$ [MH]$^+$ 385.21, found 385.32 |
| 59 | 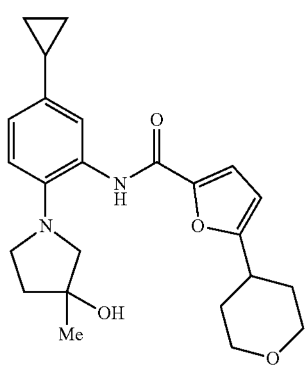 [SMILES: CC1(O)CCN(c2ccc(C3CC3)cc2NC(=O)c2ccc(C3CCOCC3)o2)C1] | N-(5-cyclopropyl-2-(3-hydroxy-3-methyl-pyrrolidin-1-yl)phenyl)-5-(tetrahydro-2H-pyran-4-yl)furan-2-carboxamide<br>$^1$H NMR (400 MHz, DMSO-d$_6$) δ 0.55-0.57 (m, 2H), 0.86-0.89 (m 2H), 1.30 (s, 3H), 1.65-1.69 (m, 2H), 1.80-1.92 (m, 5H), 2.98-3.02 (m, 2H), 3.10-3.12 (m, 2H), 3.29-3.31 (m, 1H), 3.42-3.47 (m, 2H), 3.91 (d, J = 9.6 Hz, 2H), 4.76 (s, 1H), 6.36 (d, J = 3.2 Hz, 1H), 6.80-6.87 (m, 2H), 7.18 (d, J = 2.8 Hz, 1H), 7.30 (s, 1H), 9.44 (s, 1H).<br>HPLC purity: 96.86%<br>MS (ESI-MS): m/z calcd for C$_{24}$H$_{31}$N$_2$O$_4$ [MH]$^+$ 411.22, found 411.22 |

TABLE 2-continued

Analytical data

| Example | Structure | Data |
|---|---|---|
| 60 | 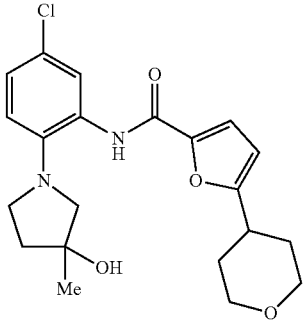 [SMILES: CC1(O)CCN(c2ccc(Cl)cc2NC(=O)c2ccc(C3CCOCC3)o2)C1] | N-(5-chloro-2-(3-hydroxy-3-methylpyrrolidin-1-yl)phenyl)-5-(tetrahydro-2H-pyran-4-yl)furan-2-carboxamide<br>$^1$H NMR (400 MHz, DMSO-$d_6$) δ 1.28 (s, 3H), 1.65-1.70 (m, 2H), 1.79-1.92 (m, 4H), 2.95-3.01 (m, 1H), 3.06 (d, J = 9.6 Hz, 1H), 3.19-3.23 (m, 2H), 3.39-3.47 (m, 3H), 3.91 (d, J = 10 Hz, 2H), 4.77 (s, 1H), 6.37 (d, J = 3.2 Hz, 1H), 6.86 (d, J = 8.8 Hz, 1H), 7.13 (dd, J = 2.4, 8.8 Hz, 1H), 7.22 (d, J = 3.2 Hz, 1H), 7.42 (d, J = 2.4 Hz, 1H), 9.61 (s, 1H).<br>HPLC purity: 99.38%<br>MS (ESI-MS): m/z calcd for $C_{21}H_{26}ClN_2O_4$ [MH]$^+$ 405.15, found 405.11 |
| 61 | 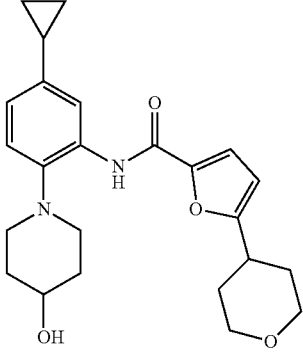 [SMILES: O=C(Nc1cc(C2CC2)ccc1N1CCC(O)CC1)c1ccc(C2CCOCC2)o1] | N-(5-cyclopropyl-2-(4-hydroxypiperidin-1-yl)phenyl)-5-(tetrahydro-2H-pyran-4-yl)furan-2-carboxamide<br>$^1$H NMR (400 MHz, DMSO-$d_6$) δ 0.60-0.63 (m, 2H), 0.92-1.96 (m, 2H), 1.62-1.75 (m, 4H), 1.86-1.99 (m, 5H), 2.68 (d, J = 9.6 Hz, 2H), 2.88-2.91 (m, 2H), 3.03-3.04 (m, 1H), 3.46 (td, J = 2, 11.6 Hz, 2H), 3.67-3.68 (m, 1H), 3.91-3.94 (m, 2H), 4.77 (d, J = 3.2 Hz, 1H), 6.43 (dd, J = 0.8, 3.6 Hz, 1H), 6.80 (dd, J = 2.4, 8.4 Hz, 1H), 7.15-7.17 (m, 2H), 8.05 (d, J = 2 Hz , 1H), 9.60 (s, 1H).<br>HPLC purity: 97.67%<br>MS (ESI-MS): m/z calcd for $C_{24}H_{31}N_2O_4$ [MH]$^+$ 411.23, found 411.17 |
| 62 | 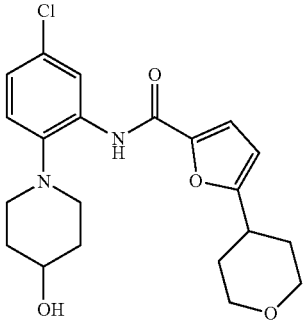 [SMILES: O=C(Nc1cc(Cl)ccc1N1CCC(O)CC1)c1ccc(C2CCOCC2)o1] | N-(5-chloro-2-(4-hydroxypiperidin-1-yl)phenyl)-5-(tetrahydro-2H-pyran-4-yl)furan-2-carboxamide<br>$^1$H NMR (400 MHz, DMSO-$d_6$) δ 1.60-1.75 (m, 4H), 1.91-1.98 (m, 4H), 2.68-2.74 (m, 2H), 2.92-2.95 (m, 2H), 3.01-3.07 (m, 1H), 3.46 (td, J = 2, 11.6 Hz, 2H), 3.69-3.70 (m, 1H), 3.91-3.94 (m, 2H), 4.80 (d, J = 3.2 Hz, 1H), 6.45 (dd, J = 0.8, 3.6 Hz, 1H), 7.14 (dd, J = 2.4, 8.4 Hz, 1H), 7.24 (d, J = 3.6 Hz, 1H), 7.31 (d, J = 8.4 Hz, 1H), 8.32 (d, J = 2.4 Hz, 1H), 9.59 (s, 1H).<br>HPLC purity: 97.88%<br>MS (ESI-MS): m/z calcd for $C_{21}H_{26}ClN_2O_4$ [MH]$^+$ 405.16, found 405.06 |
| 63 | 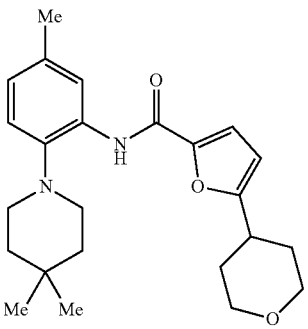 | N-(2-(4,4-dimethylpiperidin-1-yl)-5-methylphenyl)-5-(tetrahydro-2H-pyran-4-yl)furan-2-carboxamide<br>$^1$H NMR (400 MHz, DMSO-$d_6$) δ 1.03 (s, 6H), 1.55-1.58 (m, 4H), 1.68-1.78 (m, 2H), 1.94 (dd, J = 2, 12.4 Hz, 2H), 2.28 (s, 3H), 2.76-2.79 (m, 4H), 3.01-3.07 (m, 1H), 3.45 (td, J = 2, 11.6 Hz, 2H), 3.94 (dd, J = 2, 11.6 Hz, 2H), 6.44 (d, J = 0.4, 3.2 Hz, 1H), 6.91 (dd, J = 2, 8 Hz, 1H), 7.17 (d, J = 3.2 Hz, 1H), 7.26 (d, J = 8 Hz, 1H), 8.18 (d, J = 1.6 Hz, 1H), 9.54 (s, 1H).<br>HPLC purity: 99.29%<br>MS (ESI-MS): m/z calcd for $C_{24}H_{33}N_2O_3$ [MH]$^+$ 397.25, found 397.19 |

TABLE 2-continued

| Example | Structure | Data |
|---|---|---|
| 64 | 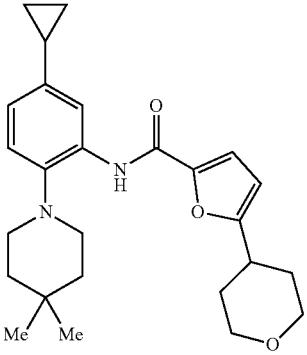 | N-(5-cyclopropyl-2-(4,4-dimethylpiperidin-1-yl)phenyl)-5-(tetrahydro-2H-pyran-4-yl)furan-2-carboxamide<br>$^1$H NMR (400 MHz, DMSO-$d_6$) δ 0.61-0.62 (m, 2H), 0.93-0.95 (m, 2H), 1.02 (s, 6H), 1.56 (br s, 4H), 1.72-1.75 (m, 2H), 1.89-1.96 (m, 3H), 2.77 (br s, 4H), 3.04 (br s, 1H), 3.40-3.48 (m, 2H), 3.93-3.95 (m, 2H), 6.44 (d, J = 3.2 Hz, 1H), 6.81 (d, J = 8.4 Hz, 1H), 7.16 (d, J = 3.2 Hz, 1H), 7.25 (d, J = 8.4 Hz, 1H), 8.10 (s, 1H), 9.52 (s, 1H).<br>HPLC purity: 95.55%<br>MS (ESI-MS): m/z calcd for $C_{26}H_{35}N_2O_3$ [MH]$^+$ 423.26, found 423.19 |
| 65 | 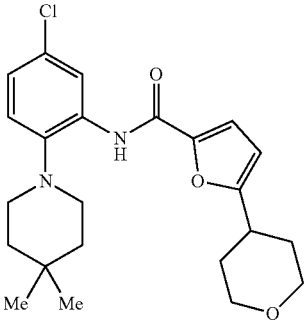 [SMILES: CC1(C)CCN(c2ccc(Cl)cc2NC(=O)c2ccc(C3CCOCC3)o2)CC1] | N-(5-chloro-2-(4,4-dimethylpiperidin-1-yl)phenyl)-5-(tetrahydro-2H-pyran-4-yl)furan-2-carboxamide<br>$^1$H NMR (400 MHz, DMSO-$d_6$) δ 1.03 (s, 6H), 1.56-1.58 (m, 4H), 1.68-1.79 (m, 2H), 1.92-1.95 (m, 2H), 2.79-2.82 (m, 4H), 3.02-3.08 (m, 1H), 3.42-3.48 (m, 2H), 3.94 (dd, J = 2.4, 11.6 Hz, 2H), 6.46 (d, J = 2.8 Hz, 1H), 7.15 (dd, J = 2.4, 8.4 Hz, 1H), 7.23 (d, J = 3.2 Hz, 1H), 7.41 (d, J = 8.4 Hz, 1H), 8.38 (d, J = 2.4 Hz, 1H), 9.51 (s, 1H).<br>HPLC purity: 98.94%<br>MS (ESI-MS): m/z calcd for $C_{23}H_{30}ClN_2O_3$ [MH]$^+$ 417.19, found 417.22 |
| 66 | 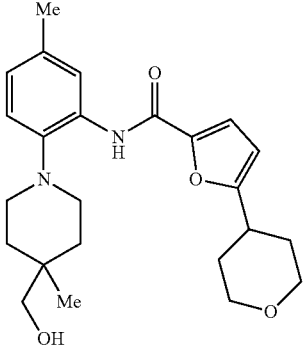 [SMILES: Cc1ccc(N2CCC(C)(CO)CC2)c(NC(=O)c2ccc(C3CCOCC3)o2)c1] | N-(2-(4-(hydroxymethyl)-4-methylpiperidin-1-yl)-5-methylphenyl)-5-(tetrahydro-2H-pyran-4-yl)furan-2-carboxamide<br>$^1$H NMR (400 MHz, DMSO-$d_6$) δ 0.98 (s, 3H), 1.42-1.46 (m, 2H), 1.66-1.74 (m, 4H), 1.95 (dd, J = 2, 12.8 Hz, 2H), 2.28 (s, 3H), 2.73-2.80 (m, 4H), 3.01-3.04 (m, 1H), 3.27 (d, J = 5.2 Hz, 2H), 3.46 (td, J = 2, 11.6 Hz, 2H), 3.94 (dd, J = 2, 11.2 Hz, 2H), 4.60 (t, J = 5.2 Hz, 1H), 6.43 (dd, J = 0.8, 3.6 Hz, 1H), 6.91 (dd, J = 1.6, 8 Hz, 1H), 7.17 (d, J = 3.2 Hz, 1H), 7.25 (d, J = 8 Hz, 1H), 8.17 (d, J = 1.6 Hz, 1H), 9.53 (s, 1H).<br>HPLC purity: 99.47%<br>MS (ESI-MS): m/z calcd for $C_{24}H_{33}N_2O_4$ [MH]$^+$ 413.24, found 413.32 |
| 67 | 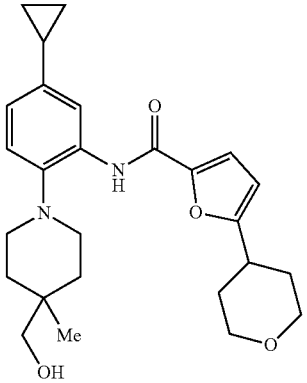 [SMILES: CC1(CO)CCN(c2ccc(C3CC3)cc2NC(=O)c2ccc(C3CCOCC3)o2)CC1] | N-(5-cyclopropyl-2-(4-(hydroxymethyl)-4-methylpiperidin-1-yl)phenyl)-5-(tetrahydro-2H-pyran-4-yl)furan-2-carboxamide<br>$^1$H NMR (400 MHz, DMSO-$d_6$) δ 0.59-0.63 (m, 2H), 0.91-0.96 (m, 2H), 0.98 (s, 3H), 1.42-1.45 (m, 2H), 1.65-1.75 (m, 4H), 1.87-1.97 (m, 3H), 2.73-2.81 (m, 4H), 3.02-3.06 (m, 1H), 3.27 (d, J = 5.2 Hz, 2H), 3.46 (td, J = 1.6, 11.6 Hz, 2H), 3.94 (dd, J = 2.4, 11.6 Hz, 2H), 4.60 (t, J = 5.2 Hz, 1H), 6.43 (dd, J = 0.8, 3.6 Hz, 1H), 6.81 (dd, J = 2, 8.4 Hz, 1H), 7.16 (d, J = 3.2 Hz, 1H), 7.23 (d, J = 8.4 Hz, 1H), 8.10 (d, J = 2 Hz, 1H), 9.51 (s, 1H).<br>HPLC purity: 99.87%<br>MS (ESI-MS): m/z calcd for $C_{26}H_{35}N_2O_4$ [MH]$^+$ 439.26, found 439.32 |

TABLE 2-continued

Analytical data

| Example | Structure | Data |
|---|---|---|
| 68 | 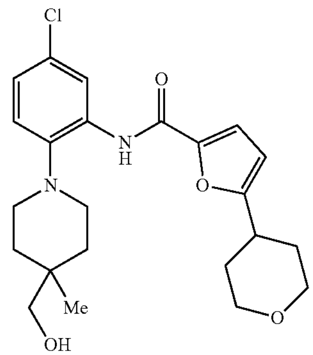 [SMILES: CC1(CO)CCN(c2ccc(Cl)cc2NC(=O)c2ccc(C3CCOCC3)o2)CC1] | N-(5-chloro-2-(4-(hydroxymethyl)-4-methyl-piperidin-1-yl)phenyl)-5-(tetrahydro-2H-pyran-4-yl)furan-2-carboxamide<br>$^1$H NMR (400 MHz, DMSO-$d_6$) δ 0.98 (s, 3H), 1.43-1.46 (m, 2H), 1.66-1.75 (m, 4H), 1.94 (dd, J = 1.6, 12.4 Hz, 2H), 2.77-2.83 (m, 4H), 3.05-3.07 (m, 1H), 3.27 (d, J = 5.2 Hz, 2H), 3.44-3.49 (m, 2H), 3.93 (dd, J = 2.4, 11.6 Hz, 2H), 4.61 (t, J = 5.2 Hz, 1H), 6.45-6.46 (m, 1H), 7.15 (dd, J = 2.4, 8.4 Hz, 1H), 7.23 (d, J = 3.6 Hz, 1H), 7.38 (d, J = 8.4 Hz, 1H), 8.37 (d, J = 2.4 Hz, 1H), 9.50 (s, 1H).<br>HPLC purity: 98.12%<br>MS (ESI-MS): m/z calcd for $C_{23}H_{30}ClN_2O_4$ [MH]$^+$ 433.18, found 433.15 |
| 69 | 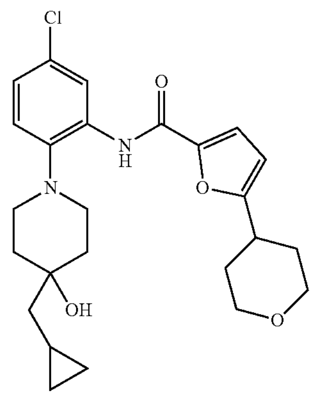 [SMILES: O=C(Nc1cc(Cl)ccc1N1CCC(O)(CC2CC2)CC1)c1ccc(C2CCOCC2)o1] | N-(5-chloro-2-(4-(cyclopropylmethyl)-4-hydroxypiperidin-1-yl)phenyl)-5-(tetrahydro-2H-pyran-4-yl)furan-2-carboxamide<br>$^1$H NMR (400 MHz, DMSO-$d_6$) δ 1.38 (s, 6H), 1.67-1.75 (m, 2H), 1.94-1.97 (m, 2H), 2.67 (br s, 4H), 2.93 (br s, 4H), 3.01-3.05 (m, 1H), 3.46-3.49 (m, 2H), 3.93-3.96 (m, 2H), 6.46 (d, J = 2.8 Hz, 1H), 7.24 (br s, 2H), 7.48-7.52 (m, 2H), 7.77-7.78 (m, 2H), 8.50 (d, J = 4 Hz, 1H), 8.64 (s, 1H), 9.38 (s, 1H).<br>HPLC purity: 98.83%<br>MS (ESI-MS): m/z calcd for $C_{29}H_{34}F_3N_4O_3$ [MH]$^+$ 543.26, found 543.26 |
| 70 | 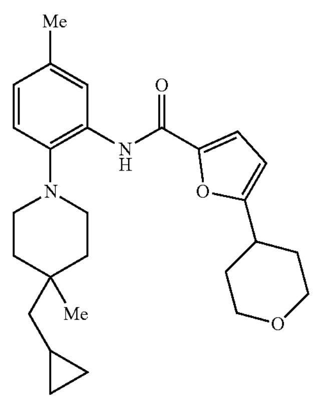 [SMILES: Cc1ccc(N2CCC(C)(CC3CC3)CC2)c(NC(=O)c2ccc(C3CCOCC3)o2)c1] | N-(2-(4-(cyclopropylmethyl)-4-hydroxypiperidin-1-yl)-5-methylphenyl)-5-(tetrahydro-2H-pyran-4-yl)furan-2-carboxamide<br>$^1$H-NMR (400 MHz, DMSO-$d_6$) δ 0.02-0.06 (m, 2H), 0.42-0.46 (m, 2H), 0.85-0.89 (m, 1H), 1.38 (d, J = 6.8 Hz, 2H), 1.63-1.79 (m, 6H), 1.88 (dd, J = 1.6, 12.8 Hz, 2H), 2.28 (s, 3H), 2.63-2.67 (m, 2H), 2.96-3.04 (m, 3H), 3.39 (td, J = 1.6, 11.6 Hz, 2H), 3.89 (dd, J = 2.4, 11.6 Hz, 2H), 4.27 (s, 1H), 6.42 (dd, J = 0.8, 3.2 Hz, 1H), 6.90 (d, J = 1.2, 8 Hz, 1H), 7.16 (d, J = 3.6 Hz, 1H), 7.20 (d, J = 8 Hz, 1H), 8.16 (d, J= 1.6 Hz, 1H), 9.57 (s, 1H).<br>HPLC: 99.35%<br>MS (ESI-MS): m/z calcd for, $C_{26}H_{35}N_2O_4$ [MH]$^+$ 439.26, found 439.32z |
| 71 | 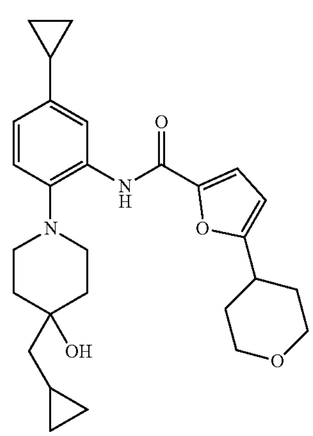 [SMILES: O=C(Nc1cc(C2CC2)ccc1N1CCC(O)(CC2CC2)CC1)c1ccc(C2CCOCC2)o1] | N-(5-cyclopropyl-2-(4-(cyclopropylmethyl)-4-hydroxypiperidin-1-yl)phenyl)-5-(tetrahydro-2H-pyran-4-yl)furan-2-carboxamide<br>$^1$H-NMR (400 MHz, DMSO-$d_6$) δ 0.03-0.04 (m, 2H), 0.42-0.46 (m, 2H), 0.58-0.62 (m, 2H), 0.88-0.95 (m, 3H), 1.38 (d, J = 6.8 Hz, 2H), 1.63-1.78 (m, 6H), 1.85-1.90 (m, 3H), 2.64 (d, J = 11.2 Hz, 2H), 2.98-3.03 (m, 3H), 3.39-3.42 (m, 2H), 3.88 (dd, J = 2.4, 11.6 Hz, 2H), 4.26 (s, 1H), 6.42 (d, J = 3.2 Hz, 1H), 7.81 (dd, J = 2, 8 Hz, 1H), 7.15 (d, J = 3.6 Hz, 1H), 7.19 (d, J = 8.4 Hz, 1H), 8.08 (d, J = 1.6 Hz, 1H), 9.55 (s, 1H).<br>HPLC: 98.87%<br>MS (ESI-MS): m/z calcd for, $C_{28}H_{37}N_2O_4$ [MH]$^+$ 465.28, found 465.32z |

TABLE 2-continued

Analytical data

| Example | Structure | Data |
|---|---|---|
| 72 | 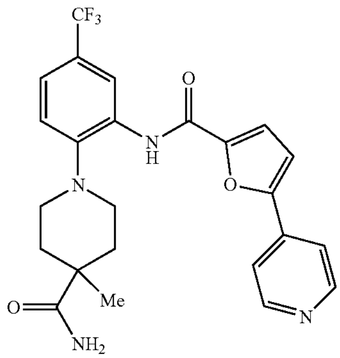 [SMILES: CC1(C(N)=O)CCN(c2ccc(C(F)(F)F)cc2NC(=O)c2ccc(-c3ccncc3)o2)CC1] | 4-methyl-1-(2-(5-(pyridin-4-yl)furan-2-carboxamido)-4-(trifluoromethyl)phenyl)-piperidine-4-carboxamide<br>$^1$H NMR (400 MHz, DMSO-d$_6$) δ 1.21 (s, 3H), 1.66-1.71 (m, 2H), 2.19-2.23 (m, 2H), 2.80-2.85 (m, 2H), 2.96-3.00 (m, 2H), 7.01 (s, 1H), 7.25 (s, 1H), 7.48-7.50 (m, 3H), 7.56 (d, J = 4 Hz, 1H), 7.83 (dd, J = 1.6, 4.8 Hz, 2H), 8.58 (s, 1H), 8.72 (d, J = 6 Hz, 2H), 9.68 (s, 1H).<br>HPLC purity: 100%<br>MS (ESI-MS): m/z calcd for C$_{24}$H$_{24}$F$_3$N$_4$O$_3$ [MH]$^+$ 473.18, found 473.17 |
| 73 | 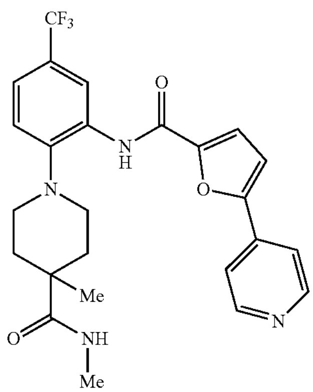 [SMILES: CNC(=O)C1(C)CCN(c2ccc(C(F)(F)F)cc2NC(=O)c2ccc(-c3ccncc3)o2)CC1] | N,4-dimethyl-1-(2-(5-(pyridin-4-yl)furan-2-carboxamido)-4-(trifluoromethyl)phenyl)-piperidine-4-carboxamide<br>$^1$H NMR (400 MHz, DMSO-d$_6$) δ 1.18 (s, 3H), 1.66-1.71 (m, 2H), 2.19-2.23 (m, 2H), 2.61 (d, J = 4.4 Hz, 3H), 2.78-2.83 (m, 2H), 2.96-2.99 (m, 2H), 7.48-7.50 (m, 3H), 7.56 (d, J = 3.6 Hz, 1H), 7.63 (q, J = 4.4 Hz, 1H), 7.84 (dd, J = 1.6, 4.8 Hz, 2H), 8.56 (s, 1H), 8.70 (dd, J = 1.6, 4.4 Hz, 2H), 9.68 (s, 1H).<br>HPLC purity: 99.78%<br>MS (ESI-MS): m/z calcd for C$_{25}$H$_{26}$F$_3$N$_4$O$_3$ [MH]$^+$ 487.20, found 487.02 |
| 74 | 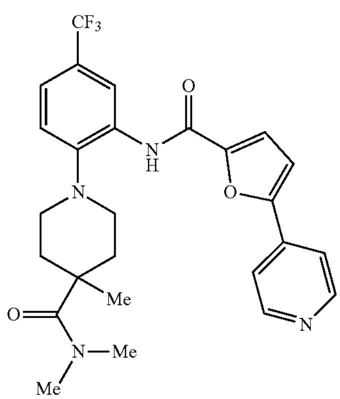 [SMILES: CN(C)C(=O)C1(C)CCN(c2ccc(C(F)(F)F)cc2NC(=O)c2ccc(-c3ccncc3)o2)CC1] | N,N,4-trimethyl-1-(2-(5-(pyridin-4-yl)furan-2-carboxamido)-4-(trifluoromethyl)phenyl)-piperidine-4-carboxamide<br>$^1$H NMR (400 MHz, DMSO-d$_6$) δ 1.33 (s, 3H), 1.78-1.83 (m, 2H), 2.28-2.33 (m, 2H), 2.86-2.90 (m, 2H), 2.92-3.02 (m, 8H), 7.46-7.50 (m, 3H), 7.55 (d, J = 3.6 Hz, 1H), 7.83 (d, J = 6 Hz, 2H), 8.56 (s, 1H), 8.70 (d, J = 5.6 Hz, 2H), 9.71 (s, 1H).<br>HPLC purity: 100%<br>MS (ESI-MS): m/z calcd for C$_{26}$H$_{28}$F$_3$N$_4$O$_3$ [MH]$^+$ 501.21, found 501.07 |
| 75 | 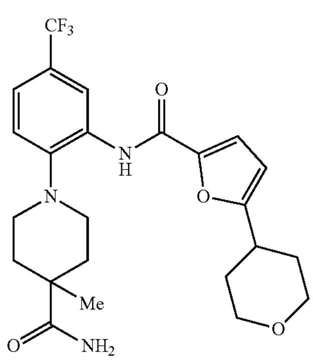 [SMILES: CC1(C(N)=O)CCN(c2ccc(C(F)(F)F)cc2NC(=O)c2ccc(C3CCOCC3)o2)CC1] | 4-methyl-1-(2-(5-(tetrahydro-2H-pyran-4-yl)furan-2-carboxamido)-4-(trifluoromethyl)-phenyl)piperidine-4-carboxamide<br>$^1$H NMR (400 MHz, DMSO-d$_6$) δ 1.93 (s, 3H), 1.60-1.74 (m, 4H), 1.91-1.94 (m, 2H), 2.19-2.22 (m, 2H), 2.75-2.80 (m, 2H), 2.90-2.94 (m, 2H), 3.00-3.07 (m, 1H), 3.43-3.48 (m, 2H), 3.92 (dd, J = 2.4, 11.6 Hz, 2H), 6.55 (d, J = 3.6 Hz, 1H), 6.99 (s, 1H), 7.25 (d, J = 3.6 Hz, 1H), 7.44 (s, 2H), 8.62 (s, 1H), 9.43 (s, 1H).<br>HPLC purity: 97.78%<br>MS (ESI-MS): m/z calcd for C$_{24}$H$_{29}$F$_3$N$_3$O$_4$ [MH]$^+$ 480.21, found 480.12 |

TABLE 2-continued

Analytical data

| Example | Structure | Data |
|---|---|---|
| 76 | 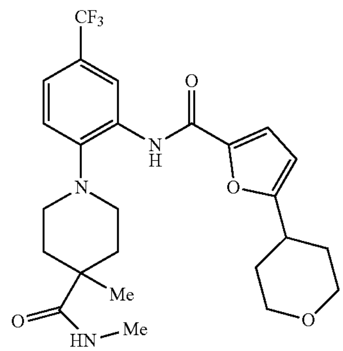 [SMILES: CNC(=O)C1(C)CCN(c2ccc(C(F)(F)F)cc2NC(=O)c2ccc(C3CCOCC3)o2)CC1] | N,4-dimethyl-1-(2-(5-(tetrahydro-2H-pyran-4-yl)furan-2-carboxamido)-4-(trifluoromethyl)-phenyl)piperidine-4-carboxamide<br>$^1$H NMR (400 MHz, DMSO-d$_6$) δ 1.18 (s, 3H), 1.61-1.74 (m, 4H), 1.92 (d, J = 2, 12.8 Hz, 2H), 2.20-2.23 (m, 2H), 2.64 (d, J = 4.4 Hz, 3H), 2.76 (t, J = 9.2 Hz, 2H), 2.90-2.94 (m, 2H), 3.01-3.08 (m, 1H), 3.45 (td, J = 2, 11.6 Hz, 2H), 3.90-3.94 (m, 2H), 6.46 (dd, J = 0.8, 3.2 Hz, 1H), 7.25 (d, J = 3.6 Hz, 1H), 7.44 (d, J = 0.8 Hz, 1H), 7.65 (d, J = 4.4 Hz, 1H), 8.62 (s, 1H), 9.42 (s, 1H).<br>HPLC purity: 100%<br>MS (ESI-MS): m/z calcd for C$_{25}$H$_{31}$F$_3$N$_3$O$_4$ [MH]$^+$ 494.23, found 494.12 |
| 77 | 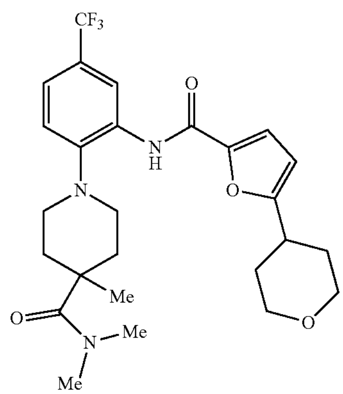 [SMILES: CN(C)C(=O)C1(C)CCN(c2ccc(C(F)(F)F)cc2NC(=O)c2ccc(C3CCOCC3)o2)CC1] | N,N,4-trimethyl-1-(2-(5-(tetrahydro-2H-pyran-4-yl)furan-2-carboxamido)-4-(trifluoromethyl)-phenyl)piperidine-4-carboxamide<br>$^1$H NMR (400 MHz, DMSO-d$_6$) δ 1.32 (s, 3H), 1.64-1.77 (m, 4H), 1.92 (dd, J = 2, 12.8 Hz, 2H), 2.27-2.32 (m, 2H), 2.83 (t, J = 8.8 Hz, 2H), 2.92-2.97 (m, 2H), 3.00 (s, 6H), 3.04-3.08 (m, 1H), 3.45 (td, J = 1.6, 11.6 Hz, 2H), 3.92 (dd, J = 2.4, 11.6 Hz, 2H), 6.45-6.46 (m, 1H), 7.25 (d, J = 3.2 Hz, 1H), 7.44 (s, 2H), 8.61 (s, 1H), 9.44 (s, 1H).<br>HPLC purity: 97.39%<br>MS (ESI-MS): m/z calcd for C$_{26}$H$_{33}$F$_3$N$_3$O$_4$ [MH]$^+$ 508.24, found 508.07 |
| 78 | 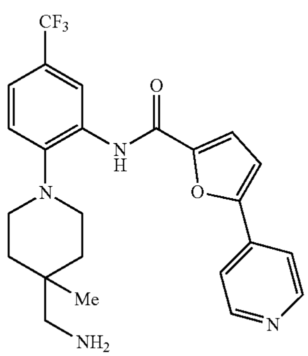 [SMILES: CC1(CN)CCN(c2ccc(C(F)(F)F)cc2NC(=O)c2ccc(-c3ccncc3)o2)CC1] | N-(2-(4-(aminomethyl)-4-methylpiperidin-1-yl)-5-(trifluoromethyl)phenyl)-5-(pyridin-4-yl)furan-2-carboxamide<br>$^1$H NMR (400 MHz, DMSO-d$_6$) δ 0.96 (s, 3H), 1.52 (br s, 2H), 1.67 (br s, 2H), 2.42 (br s, 4H), 2.91 (br s, 4H), 7.50-7.55 (m, 4H), 7.86 (s, 2H), 8.57 (s, 1H), 8.71 (d, J = 3.2 Hz, 2H), 9.64 (br s, 1H).<br>HPLC purity: 96.76%.<br>MS (ESI-MS): m/z calcd for C$_{24}$H$_{26}$F$_3$N$_4$O$_2$ [MH]$^+$ 459.20, found 459.20 |
| 79 | 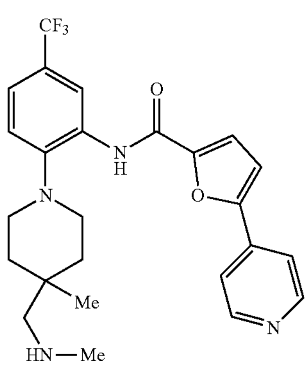 [SMILES: CNCC1(C)CCN(c2ccc(C(F)(F)F)cc2NC(=O)c2ccc(-c3ccncc3)o2)CC1] | N-(2-(4-methyl-4-((methylamino)-methyl)piperidin-1-yl)-5-(trifluoromethyl)phenyl)-5-(pyridin-4-yl)furan-2-carboxamide<br>$^1$H NMR (400 MHz, DMSO-d$_6$) δ 1.06 (s, 3H), 1.58-1.61 (m, 2H), 1.69-1.71 (m, 2H), 2.45 (br s, 3H), 2.69 (br s, 2H), 2.85-3.02 (m, 5H), 7.50-7.57 (m, 4H), 7.87 (d, J = 6 Hz, 2H), 8.51 (s, 1H), 8.73 (br s, 2H), 9.65 (s, 1H).<br>HPLC purity: 100%<br>MS (ESI-MS): m/z calcd for C$_{25}$H$_{28}$F$_3$N$_4$O$_2$ [MH]$^+$ 473.22, found 473.20 |

TABLE 2-continued

Analytical data

| Example | Structure | Data |
|---|---|---|
| 80 | 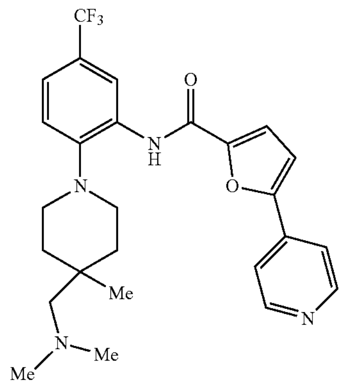 [SMILES: CN(C)CC1(C)CCN(c2ccc(C(F)(F)F)cc2NC(=O)c2ccc(-c3ccncc3)o2)CC1] | N-(2-(4-((dimethylamino)methyl)-4-methyl-piperidin-1-yl)-5-(trifluoromethyl)phenyl)-5-(pyridin-4-yl)furan-2-carboxamide<br>$^1$H NMR (400 MHz, DMSO-$d_6$) δ 1.01 (s, 3H), 1.49-1.52 (m, 2H), 1.62-1.67 (m, 2H), 2.17 (br s, 8H), 2.91-2.92 (m, 4H), 7.48-7.56 (m, 4H), 7.86 (d, J = 6 Hz, 2H), 8.51 (s, 1H), 8.71 (d, J = 5.6 Hz, 2H), 9.61 (s, 1H).<br>HPLC purity: 100%<br>MS (ESI-MS): m/z calcd for $C_{26}H_{30}F_3N_4O_2$ [MH]$^+$ 487.23, found 487.10 |
| 81 | 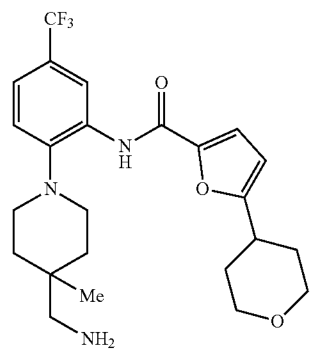 [SMILES: CC1(CN)CCN(c2ccc(C(F)(F)F)cc2NC(=O)c2ccc(C3CCOCC3)o2)CC1] | N-(2-(4-(aminomethyl)-4-methylpiperidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 0.97 (s, 3H), 1.49-1.52 (m, 2H), 1.61-1.76 (m, 4H), 1.93 (dd, J = 2, 12.8 Hz, 2H), 2.46 (br s, 4H), 2.85-2.88 (m, 4H), 3.02-3.09 (m, 1H), 3.45 (td, J = 2, 11.6 Hz, 2H), 3.94 (dd, J = 2, 11.2 Hz, 2H), 6.46 (d, J = 3.6 H, 1H), 7.24 (d, J = 3.2 Hz, 1H), 7.44-7.53 (m, 2H), 8.64 (d, J = 2 Hz, 1H), 9.40 (br s, 1H).<br>HPLC purity: 97.60%.<br>MS (ESI-MS): m/z calcd for $C_{24}H_{31}F_3N_3O_3$ [MH]$^+$ 466.23, found 466.37 |
| 82 | 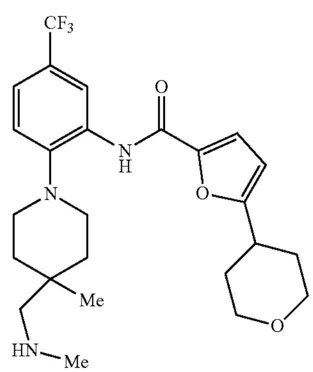 [SMILES: CNCC1(C)CCN(c2ccc(C(F)(F)F)cc2NC(=O)c2ccc(C3CCOCC3)o2)CC1] | N-(2-(4-methyl-4-((methylamino)methyl)-piperidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 1.15 (s, 3H), 1.68-1.79 (m, 6H), 1.89-1.92 (m, 2H), 2.59 (s, 3H), 2.88-2.93 (m, 6H), 3.06-3.12 (m, 1H), 3.44-3.49 (m, 2H), 3.95-3.97 (m, 2H), 6.47 (d, J = 3.2 Hz, 1H), 7.30 (d, J = 3.2 Hz, 1H), 7.48-7.50 (m, 1H), 7.54-7.56 (m, 1H), 8.36 (br s, 1H), 8.64 (s, 1H), 9.41 (s, 1H).<br>HPLC purity: 96.99%<br>MS (ESI-MS): m/z calcd for $C_{25}H_{33}F_3N_3O_3$ [MH]$^+$ 480.25, found 480.22 |
| 83 | 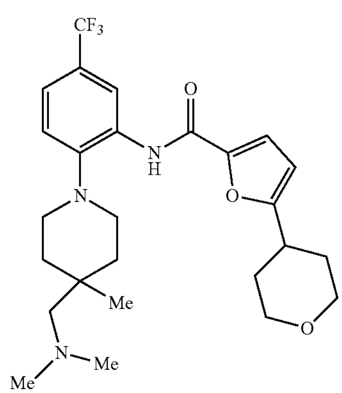 [SMILES: CN(C)CC1(C)CCN(c2ccc(C(F)(F)F)cc2NC(=O)c2ccc(C3CCOCC3)o2)CC1] | N-(2-(4-((dimethylamino)methyl)-4-methyl-piperidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 1.04 (s, 3H), 1.52-1.55 (m, 2H), 1.59-1.77 (m, 4H), 1.92-1.96 (m, 2H), 2.21 (s, 2H), 2.27 (s, 6H), 2.83-2.91 (m, 4H), 3.02-3.07 (m, 1H), 3.43-3.49 (m, 2H), 3.95 (dd, J = 2, 11.6 Hz, 2H), 6.47 (d, J = 3.6 Hz, 1H), 7.24 (d, J = 3.6 Hz, 1H), 7.43-7.47 (m, 1H), 7.53-7.55 (m, 1H), 8.63 (d, J = 1.6 Hz, 1H), 9.39 (s, 1H).<br>HPLC purity: 100%<br>MS (ESI-MS): m/z calcd for $C_{26}H_{35}F_3N_3O_3$ [MH]$^+$ 494.26, found 494.37 |

TABLE 2-continued

Analytical data

| Example | Structure | Data |
|---|---|---|
| 84 | 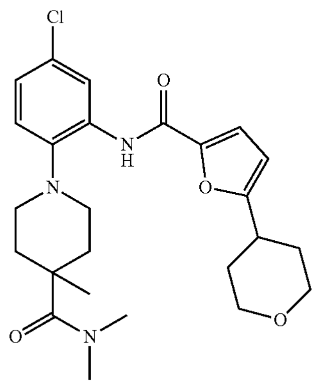 [SMILES: CN(C)C(=O)C1(C)CCN(c2ccc(Cl)cc2NC(=O)c2ccc(C3CCOCC3)o2)CC1] | 1-(4-chloro-2-(5-(tetrahydro-2H-pyran-4-yl)furan-2-carboxamido)phenyl)-N,N,4-trimethyl-piperidine-4-carboxamide<br>$^1$H NMR (400 MHz, DMSO-$d_6$) δ 1.31 (s, 3H), 1.67-1.72 (m, 4H), 1.90-1.94 (m, 2H), 2.26 (br s, 2H), 2.73-2.78 (m, 2H), 2.84-2.86 (m, 2H), 2.99-3.04 (m, 7H), 3.45 (t, J = 10.8 Hz, 2H), 3.91-3.93 (m, 2H), 6.44 (d, J = 2.8 Hz, 1H), 7.13 (dd, J = 2.4, 8.4 Hz, 1H), 7.23 (d, J = 3.2 Hz, 1H), 7.29 (d, J = 8.8 Hz, 1H), 8.34 (d, J = 2 Hz, 1H), 9.53 (s, 1H).<br>HPLC purity: 100%<br>MS (ESI-MS): m/z calcd for $C_{25}H_{33}ClN_3O_4$ [MH]$^+$ 474.22, found 474.16 |
| 85 | 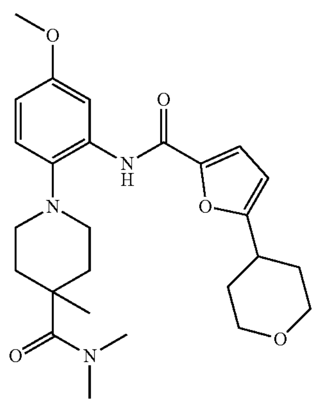 | 1-(4-methoxy-2-(5-(tetrahydro-2H-pyran-4-yl)furan-2-carboxamido)phenyl)-N,N,4-trimethyl-piperidine-4-carboxamide<br>$^1$H NMR (400 MHz, DMSO-$d_6$) δ 1.31 (s, 3H), 1.67-1.72 (m, 4H), 1.90-1.94 (m, 2H), 2.27-2.32 (m, 5H), 2.71-2.75 (m, 2H), 2.80-2.82 (m, 2H), 2.99-3.03 (m, 7H), 3.44 (t, J = 10.8 Hz, 2H), 3.91-3.93 (m, 2H), 6.41 (d, J = 3.2 Hz, 1H), 6.89 (d, J = 8 Hz, 1H), 7.14-7.16 (m, 2H), 8.14 (s, 1H), 9.56 (s, 1H).<br>HPLC purity: 100%<br>MS (ESI-MS): m/z calcd for $C_{26}H_{36}N_3O_4$ [MH]$^+$ 454.27, found 454.21 |
| 86 | 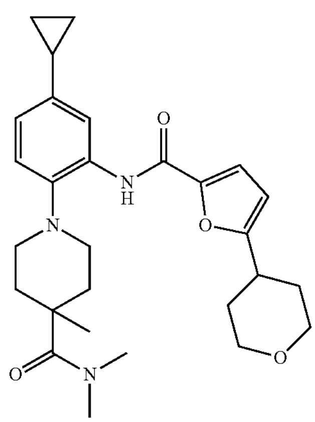 [SMILES: CN(C)C(=O)C1(C)CCN(c2ccc(C3CC3)cc2NC(=O)c2ccc(C3CCOCC3)o2)CC1] | 1-(4-cyclopropyl-2-(5-(tetrahydro-2H-pyran-4-yl)furan-2-carboxamido)phenyl)-N,N,4-trimethyl-piperidine-4-carboxamide<br>$^1$H NMR (400 MHz, DMSO-$d_6$) δ 0.60 (br s, 2H), 0.91-0.93 (m, 2H), 1.30 (s, 3H), 1.69 (br s, 4H), 1.90-1.93 (m, 4H), 2.25 (br s, 2H), 2.72-2.81 (m, 4H), 2.99 (br s, 6H), 3.41-3.47 (m, 2H), 3.92 (d, J = 8.4 Hz, 2H), 6.42 (s, 1H), 6.79 (d, J = 8 Hz, 1H), 7.12-7.15 (m, 2H), 8.06 (s, 1H), 9.54 (s, 1H).<br>HPLC purity: 98.20%<br>MS (ESI-MS): m/z calcd for $C_{28}H_{38}N_3O_4$ [MH]$^+$ 480.29, found 480.42 |
| 87 | 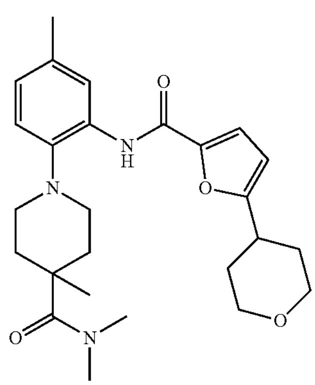 | N,N,4-trimethyl-1-(4-methyl-2-(5-(tetrahydro-2H-pyran-4-yl)furan-2-carboxamido)phenyl)piperidine-4-carboxamide<br>$^1$H NMR (400 MHz, DMSO-$d_6$) δ 1.31 (s, 3H), 1.70 (br s, 4H), 1.90-1.93 (m, 2H), 2.25 (br s, 2H), 2.72-2.80 (m, 4H), 2.99 (br s, 7H), 3.44 (t, J = 10.8 Hz, 2H), 3.72 (s, 3H), 3.91-3.93 (m, 2H), 6.42 (s, 1H), 6.64 (d, J = 6.4 Hz, 1H), 7.17-7.22 (m, 1H), 7.97 (s, 1H), 9.69 (s, 1H).<br>HPLC purity: 99.29%<br>MS (ESI-MS): m/z calcd for $C_{28}H_{36}F_3N_3O_5$ [MH]$^+$ 470.27, found 470.21 |

TABLE 2-continued

Analytical data

| Example | Structure | Data |
|---------|-----------|------|
| 88 | 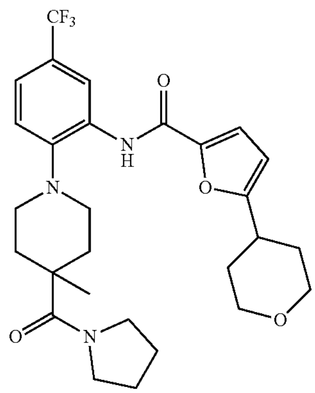 [SMILES: CC1(C(=O)N2CCCC2)CCN(c2ccc(C(F)(F)F)cc2NC(=O)c2ccc(C3CCOCC3)o2)CC1] | N-(2-(4-methyl-4-(pyrrolidine-1-carbonyl)-piperidin-1-yl)-5-(trifluoromethyl)-phenyl)-5-(tetrahydro-2H-pyran-4-yl)furan-2-carboxamide<br>$^1$H NMR (400 MHz, DMSO-d$_6$) δ 1.28 (s, 3H), 1.66-1.82 (m, 8H), 1.92-1.96 (m, 2H), 2.23-2.25 (m, 2H), 2.82-2.86 (m, 2H), 2.94-2.98 (m, 2H), 3.04-3.10 (m, 1H), 3.41-3.49 (m, 6H), 3.92-3.95 (m, 2H), 6.47 (d, J = 2.8 Hz, 1H), 7.26 (d, J = 3.6 Hz, 1H), 7.46 (d, J = 0.8 Hz, 2H), 8.62 (s, 1H), 9.46 (s, 1H).<br>HPLC purity: 97.01%<br>MS (ESI-MS): m/z calcd for C$_{28}$H$_{35}$F$_3$N$_3$O$_4$ [MH]$^+$ 534.26, found 534.08 |
| 89 | 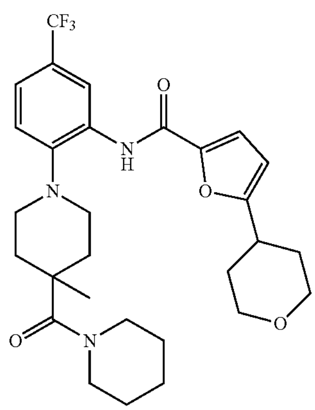 [SMILES: CC1(C(=O)N2CCCCC2)CCN(c2ccc(C(F)(F)F)cc2NC(=O)c2ccc(C3CCOCC3)o2)CC1] | N-(2-(4-methyl-4-(piperidine-1-carbonyl)-piperidin-1-yl)-5-(trifluoromethyl)phenyl)-5-(tetrahydro-2H-pyran-4-yl)furan-2-carboxamide<br>$^1$H NMR (400 MHz, DMSO-d$_6$) δ 1.32 (s, 3H), 1.47 (br s, 4H), 1.59-1.75 (m, 6H), 1.91-1.95 (m, 2H), 2.23-2.27 (m, 2H), 2.82-2.86 (m, 2H), 2.93-2.97 (m, 2H), 3.02-3.08 (m, 1H), 3.42-3.48 (m, 2H), 3.53 (br s, 4H), 3.92 (dd, J = 2, 12.4 Hz, 2H), 6.45 (d, J = 3.2 Hz, 1H), 7.24 (d, J = 3.6 Hz, 1H), 7.44 (s, 2H), 8.60 (s, 1H), 9.45 (s, 1H).<br>HPLC purity: 98.64%<br>MS (ESI-MS): m/z calcd for C$_{29}$H$_{37}$F$_3$N$_3$O$_4$ [MH]$^+$ 548.27, found 548.08 |
| 90 | 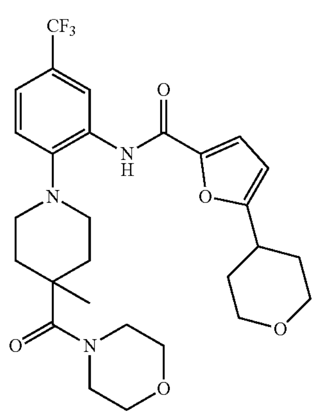 [SMILES: CC1(C(=O)N2CCOCC2)CCN(c2ccc(C(F)(F)F)cc2NC(=O)c2ccc(C3CCOCC3)o2)CC1] | N-(2-(4-methyl-4-(morpholine-4-carbonyl)-piperidin-1-yl)-5-(trifluoromethyl)phenyl)-5-(tetrahydro-2H-pyran-4-yl)furan-2-carboxamide<br>$^1$H NMR (400 MHz, DMSO-d$_6$) δ 1.32 (s, 3H), 1.67-1.74 (m, 4H), 1.91-1.94 (m, 2H), 2.24-2.27 (m, 2H), 2.85-2.87 (m, 2H), 2.93-2.95 (m, 2H), 3.00-3.10 (m, 1H), 3.41-3.47 (m, 2H), 3.58 (br s, 8H), 3.91-3.93 (m, 2H), 6.45 (d, J = 3.2 Hz, 1H), 7.24 (d, J = 3.2 Hz, 1H), 7.45 (s, 2H), 8.60 (s, 1H), 9.45 (s, 1H).<br>HPLC purity: 97.95%<br>MS (ESI-MS): m/z calcd for C$_{28}$H$_{35}$F$_3$N$_3$O$_5$ [MH]$^+$ 550.25, found 550.08 |

TABLE 2-continued

Analytical data

| Example | Structure | Data |
|---|---|---|
| 91 | 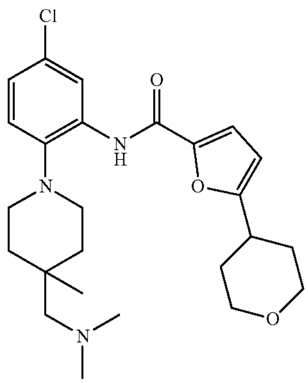 [SMILES: CN(C)CC1(C)CCN(c2ccc(Cl)cc2NC(=O)c2ccc(C3CCOCC3)o2)CC1] | N-(5-chloro-2-(4-((dimethylamino)methyl)-4-methylpiperidin-1-yl)phenyl)-5-(tetrahydro-2H-pyran-4-yl)furan-2-carboxamide<br>$^1$H NMR (400 MHz, DMSO-$d_6$) δ 1.04 (s, 3H), 1.54-1.60 (m, 4H), 1.70-1.74 (m, 2H), 1.92-1.95 (m, 2H), 2.20-2.27 (m, 8H), 2.78-2.82 (m, 4H), 2.90-3.10 (m, 1H), 3.40-3.48 (m, 2H), 3.94 (dd, J = 2.4, 11.6 Hz, 2H), 6.45 (d, J = 2.8 Hz, 1H), 7.14 (dd, J = 2.4, 8.8 Hz, 1H), 7.23 (d, J = 3.6 Hz, 1H), 7.41 (d, J = 8.8 Hz, 1H), 8.36 (d, J = 2.4 Hz, 1H), 9.48 (s, 1H).<br>HPLC purity: 99.76%<br>MS (ESI-MS): m/z calcd for $C_{25}H_{35}ClN_3O_3$ [MH]$^+$ 460.24, found 460.21 |
| 92 | 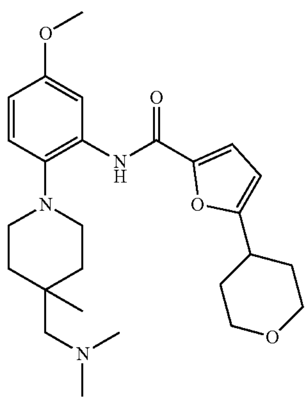 [SMILES: COc1ccc(N2CCC(C)(CN(C)C)CC2)c(NC(=O)c2ccc(C3CCOCC3)o2)c1] | N-(2-(4-((dimethylamino)methyl)-4-methyl-piperidin-1-yl)-5-methoxyphenyl)-5-(tetrahydro-2H-pyran-4-yl)furan-2-carboxamide<br>$^1$H NMR (400 MHz, DMSO-$d_6$) δ 1.03 (s, 3H), 1.49-1.60 (m, 4H), 1.70-1.77 (m, 2H), 1.94 (d, J = 11.6 Hz, 2H), 2.19 (s, 2H), 2.27 (s, 6H), 2.68-2.71 (m, 2H), 2.77-2.81 (m, 2H), 3.00-3.06 (m, 1H), 3.43-3.49 (m, 2H), 3.72 (s, 3H), 3.94 (d, J = 9.6 Hz, 2H), 6.43 (d, J = 3.2 Hz, 1H), 6.65 (dd, J = 2.8, 8.8 Hz, 1H), 7.17 (d, J = 3.6 Hz, 1H), 7.32 (d, J = 8.4 Hz, 1H), 7.99 (d, J = 2.8 Hz, 1H), 9.64 (s, 1H).<br>HPLC purity: 100%<br>MS (ESI-MS): m/z calcd for $C_{26}H_{38}F_3O_4$ [MH]$^+$ 456.29, found 456.21 |
| 93 | 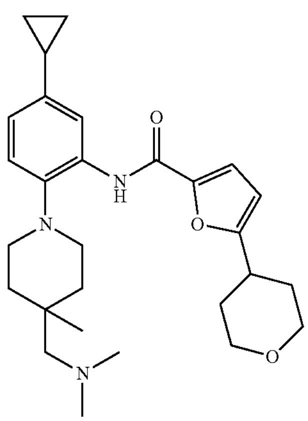 [SMILES: CN(C)CC1(C)CCN(c2ccc(C3CC3)cc2NC(=O)c2ccc(C3CCOCC3)o2)CC1] | N-(5-cyclopropyl-2-(4-((dimethylamino)methyl)-4-methylpiperidin-1-yl)phenyl)-5-(tetrahydro-2H-pyran-4-yl)furan-2-carboxamide<br>$^1$H NMR (400 MHz, DMSO-$d_6$) δ 0.58-0.62 (m, 2H), 0.90-0.95 (m, 2H), 1.03 (s, 3H), 1.49-1.58 (m, 4H), 1.70-1.76 (m, 2H), 1.85-1.96 (m, 3H), 2.19 (s, 2H), 2.26 (s, 6H), 2.66-2.79 (m, 4H), 2.98-3.07 (m, 1H), 3.40-3.48 (m, 2H), 3.94 (dd, J = 2.4, 11.6 Hz, 2H), 6.43 (d, J = 2.8 Hz, 1H), 6.80 (dd, J = 2, 8.4 Hz, 1H), 7.15 (d, J = 3.6 Hz, 1H), 7.24 (d, J = 8.4 Hz, 1H), 8.06 (d, J = 2 Hz, 1H), 9.48 (s, 1H).<br>HPLC purity: 96.28%<br>MS (ESI-MS): m/z calcd for $C_{28}H_{40}N_3O_3$ [MH]$^+$ 466.31, found 466.40 |
| 94 | 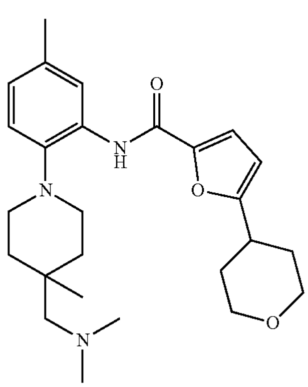 [SMILES: Cc1ccc(N2CCC(C)(CN(C)C)CC2)c(NC(=O)c2ccc(C3CCOCC3)o2)c1] | N-(2-(4-((dimethylamino)methyl)-4-methyl-piperidin-1-yl)-5-methylphenyl)-5-(tetrahydro-2H-pyran-4-yl)furan-2-carboxamide<br>$^1$H NMR (400 MHz, DMSO-$d_6$) δ 1.03 (s, 3H), 1.49-1.61 (m, 4H), 1.67-1.77 (m, 2H), 1.94 (d, J = 11.2 Hz, 2H), 2.20-2.27 (m, 11H), 2.67-2.82 (m, 4H), 3.00-3.06 (m, 1H), 3.43-3.48 (m, 2H), 3.94 (d, J = 9.2 Hz, 2H), 6.43 (d, J = 3.2 Hz, 1H), 6.90 (d, J = 7.2 Hz, 1H), 7.16 (d, J = 3.2 Hz, 1H), 7.25 (d, J = 8 Hz, 1H), 8.16 (s, 1H), 9.50 (s, 1H).<br>HPLC purity: 99.61%<br>MS (ESI-MS): m/z calcd for $C_{26}H_{38}N_3O_3$ [MH]$^+$ 440.29, found 440.21 |

TABLE 2-continued

Analytical data

| Example | Structure | Data |
|---|---|---|
| 95 | 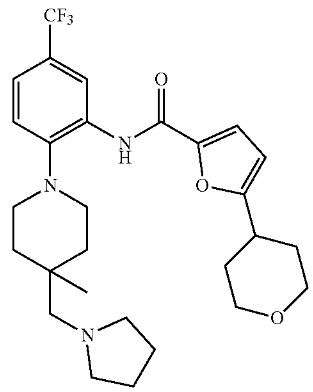 [SMILES: CC1(CN2CCCC2)CCN(c2ccc(C(F)(F)F)cc2NC(=O)c2ccc(C3CCOCC3)o2)CC1] | N-(2-(4-methyl-4-(pyrrolidin-1-ylmethyl)piperidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 1.05 (s, 3H), 1.54-1.74 (m, 10H), 1.93-1.96 (m, 2H), 2.41 (s, 2H), 2.60 (br s, 4H), 2.86-2.87 (m, 4H), 3.00-3.10 (m, 1H), 3.42-3.48 (m, 2H), 3.94 (dd, J = 2, 11.6 Hz, 2H), 6.46 (dd, J = 0.8, 3.6 Hz, 1H), 7.24 (d, J = 3.2 Hz, 1H), 7.45-7.47 (m, 1H), 7.53 (d, J = 8.4 Hz, 1H), 8.63 (d, J = 1.6 Hz, 1H), 9.40 (s, 1H).<br>HPLC purity: 100%<br>MS (ESI-MS): m/z calcd for $C_{28}H_{37}F_3N_3O_3$ [MH]$^+$ 520.28, found 520.17 |
| 96 | 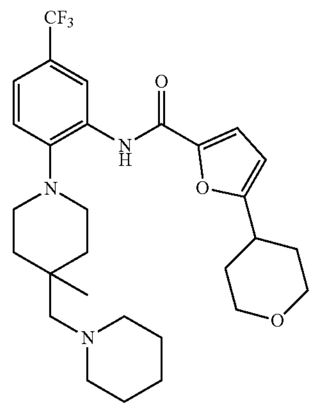 [SMILES: CC1(CN2CCCCC2)CCN(c2ccc(C(F)(F)F)cc2NC(=O)c2ccc(C3CCOCC3)o2)CC1] | N-(2-(4-methyl-4-(piperidin-1-ylmethyl)piperidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 1.01 (s, 3H), 1.34 (br s, 2H), 1.47-1.59 (m, 8H), 1.69-1.74 (m, 2H), 1.92-1.95 (m, 2H), 2.18 (s, 2H), 2.50 (br s, 4H, merged in DMSO residual), 2.86-2.87 (m, 4H), 3.01-3.06 (m, 1H), 3.42-3.48 (m, 2H), 3.94 (dd, J = 2, 11.6 Hz, 2H), 6.46 (dd, J = 0.8, 3.6 Hz, 1H), 7.27 (d, J = 3.6 Hz, 1H), 7.45 (dd, J = 1.6, 8.4 Hz, 1H), 7.53 (d, J = 8 Hz, 1H), 8.62 (d, J = 2 Hz, 1H), 9.40 (s, 1H).<br>HPLC purity: 100%<br>MS (ESI-MS): m/z calcd for $C_{29}H_{39}F_3N_3O_3$ [MH]$^+$ 534.29, found 534.18 |
| 97 | 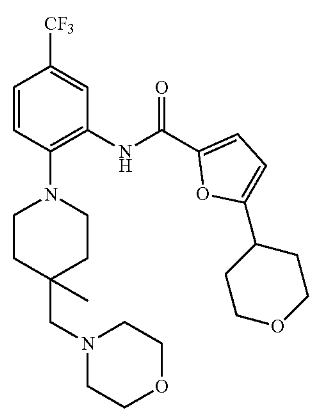 [SMILES: CC1(CN2CCOCC2)CCN(c2ccc(C(F)(F)F)cc2NC(=O)c2ccc(C3CCOCC3)o2)CC1] | N-(2-(4-methyl-4-(morpholinomethyl)piperidin-1-yl)-5-(trifluoromethyl)phenyl)-5-(tetrahydro-2H-pyran-4-yl)furan-2-carboxamide<br>$^1$H NMR (400 MHz, DMSO-$d_6$) δ 1.04 (s, 3H), 1.58-1.61 (m, 4H), 1.70-1.74 (m, 2H), 1.92-1.95 (m, 2H), 2.24 (s, 2H), 2.50 (br s, 4H, merged in DMSO residual), 2.86-2.87 (m, 4H), 3.01-3.07 (m, 1H), 3.43-3.48 (m, 2H), 3.56 (t, J = 4.4 Hz, 4H), 3.95 (dd, J = 2.4, 11.6 Hz, 2H), 6.46 (m, 1H), 7.24 (d, J = 3.2 Hz, 1H), 7.46 (dd, J = 2, 8.4 Hz, 1H), 7.54 (d, J = 8.4 Hz, 1H), 8.62 (d, J = 2 Hz, 1H), 9.40 (s, 1H).<br>HPLC purity: 96.57%<br>MS (ESI-MS): m/z calcd for $C_{28}H_{37}F_3N_3O_4$ [MH]$^+$ 536.27, found 536.13 |
| 98 | 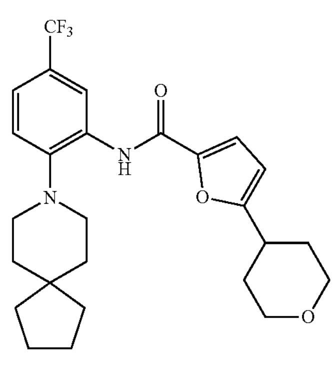 [SMILES: O=C(Nc1cc(C(F)(F)F)ccc1N1CCC2(CCCC2)CC1)c1ccc(C2CCOCC2)o1] | N-(2-(8-azaspiro[4.5]decan-8-yl)-5-(trifluoromethyl)phenyl)-5-(tetrahydro-2H-pyran-4-yl)furan-2-carboxamide<br>$^1$H NMR (400 MHz, DMSO-$d_6$) δ 1.51-1.52 (m, 4H), 1.63-1.77 (m, 10H), 1.92-1.95 (m, 2H), 2.85-2.88 (m, 4H), 3.02-3.08 (m, 1H), 3.43-3.48 (m, 2H), 3.93-3.95 (m, 2H), 6.47 (d, J = 3.2 Hz, 1H), 7.25 (d, J = 3.2 Hz, 1H), 7.45-7.51 (m, 2H), 8.65 (s, 1H), 9.50 (s, 1H).<br>HPLC purity: 95.08%<br>MS (ESI-MS): m/z calcd for $C_{26}H_{32}F_3N_2O_3$ [MH]$^+$ 477.23, found 477.17 |

TABLE 2-continued

| Example | Structure | Data |
|---|---|---|
| 99 | 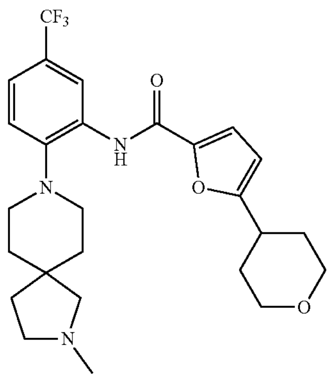 [SMILES: CN1CCC2(CCN(c3ccc(C(F)(F)F)cc3NC(=O)c3ccc(C4CCOCC4)o3)CC2)C1] | N-(2-(2-methyl-2,8-diazaspiro[4.5]decan-8-yl)-5-(trifluoromethyl)phenyl)-5-(tetrahydro-2H-pyran-4-yl)furan-2-carboxamide<br>¹H NMR (400 MHz, DMSO-d₆) δ 1.65 (t, J = 6.8 Hz, 2H), 1.70-1.80 (m, 6H), 1.90-1.94 (m, 2H), 2.24 (s, 3H), 2.39 (s, 2H), 2.50 (br s, 2H, merged with DMSO residual), 2.84 (br s, 4H), 3.02-3.08 (m, 1H), 3.42-3.48 (m, 2H), 3.92-3.94 (m, 2H), 6.46 (dd, J = 3.2 Hz, 1H), 7.24 (d, J = 3.6 Hz, 1H), 7.44-7.49 (m, 2H), 8.63 (s, 1H), 9.50 (s, 1H).<br>HPLC purity: 98.21%<br>MS (ESI-MS): m/z calcd for $C_{26}H_{33}F_3N_3O_3$ [MH]⁺ 492.25, found 492.07 |
| 100 | 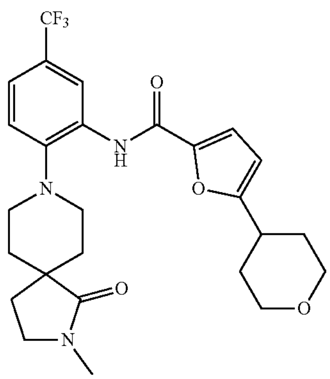 [SMILES: CN1CCC2(CCN(c3ccc(C(F)(F)F)cc3NC(=O)c3ccc(C4CCOCC4)o3)CC2)C1=O] | N-(2-(2-methyl-1-oxo-2,8-diazaspiro[4.5]decan-8-yl)-5-(trifluoromethyl)phenyl)-5-(tetrahydro-2H-pyran-4-yl)furan-2-carboxamide<br>¹H NMR (400 MHz, DMSO-d₆) δ 1.52-1.56 (m, 2H), 1.59-1.69 (m, 2H), 1.96-2.03 (m, 6H), 2.76 (s, 3H), 2.81-2.86 (m, 2H), 3.01-3.04 (m, 2H), 3.07-3.15 (m, 1H), 3.30-3.31 (m, 2H), 3.53 (td, J = 1.6, 11.6 Hz, 2H), 3.93 (dd, J = 2.4, 11.6 Hz, 2H), 6.44 (dd, J = 0.8, 3.6 Hz, 1H), 7.24 (d, J = 3.2 Hz, 1H), 7.48 (br s, 2H), 8.62 (s, 1H), 9.46 (s, 1H).<br>HPLC purity: 100%<br>MS (ESI-MS): m/z calcd for $C_{26}H_{31}F_3N_3O_4$ [MH]⁺ 506.23, found 506.20 |
| 101 | 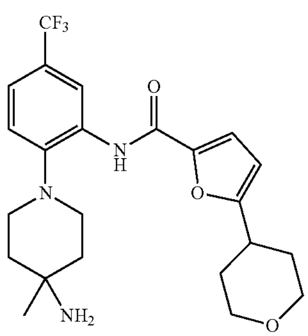 [SMILES: CC1(N)CCN(c2ccc(C(F)(F)F)cc2NC(=O)c2ccc(C3CCOCC3)o2)CC1] | N-(2-(4-amino-4-methylpiperidin-1-yl)-5-(trifluoromethyl)-phenyl)-5-(tetrahydro-2H-pyran-4-yl)furan-2-carboxamide<br>¹H NMR (400 MHz, DMSO-d₆) δ 1.29 (s, 3H), 1.64-1.74 (m, 2H), 1.76-1.87 (m, 4H), 1.89-1.93 (m, 2H), 2.85-2.88 (m, 2H), 3.06-3.13 (m, 3H), 3.37 (br s, 3H, merged with residual moisture in DMSO), 3.43-3.49 (m, 2H), 3.92 (dd, J = 2.4, 10 Hz, 2H), 6.45 (d, J = 3.6 Hz, 1H), 7.26 (d, J = 3.6 Hz, 1H), 7.48-7.53 (m, 2H), 8.59 (s, 1H), 9.36 (s, 1H).<br>HPLC purity: 99.75%<br>MS (ESI-MS): m/z calcd for $C_{23}H_{29}F_3N_3O_3$ [MH]⁺ 452.22, found 452.16 |
| 102 | 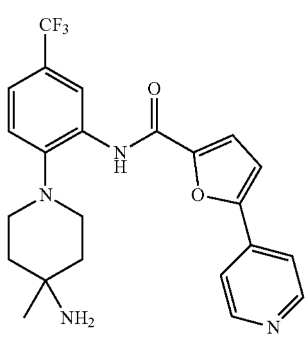 [SMILES: CC1(N)CCN(c2ccc(C(F)(F)F)cc2NC(=O)c2ccc(-c3ccncc3)o2)CC1] | N-(2-(4-amino-4-methylpiperidin-1-yl)-5-(trifluoromethyl)phenyl)-5-(pyridin-4-yl)furan-2-carboxamide<br>¹H NMR (400 MHz, DMSO-d₆) δ 1.14 (s, 3H), 1.58-1.61 (m, 2H), 1.69-1.75 (m, 2H), 2.82-2.85 (m, 2H), 3.08 (t, J = 8.8 Hz, 2H), 7.49-7.54 (m, 3H), 7.56 (d, J = 3.6 Hz, 2H), 7.86 (d, J = 6 Hz, 2H), 8.55 (s, 1H), 8.70 (d, J = 6 Hz, 2H), 9.69 (br s, 1H).<br>HPLC purity: 99.57%<br>MS (ESI-MS): m/z calcd for $C_{23}H_{24}F_3N_4O_2$ [MH]⁺ 445.19, found 445.10 |

TABLE 3

| | | SRPK1 and CYP activity assay data | | | | |
|---|---|---|---|---|---|---|
| | | CYP Inhibition Activity (IC$_{50}$/nM) | | | | |
| Example | SRPK1 (IC$_{50}$/nM) | CYP1A2 | CYP2C9 | CYP2C19 | CYP2D6 | CYP3A4 |
| Reference Example 1 | 3.2 | >30000 | 170 | 230 | 740 | 310 |
| Reference Example 2 | 0.4 | 21800 | 610 | 690 | 260 | 1180 |
| Reference Example 3 | 3.5 | >30000 | 230 | 610 | 7078 | 4160 |
| Reference Example 4 | 1.3 | >30000 | 170 | 290 | 550 | 830 |
| Reference Example 5 | 27.5 | 15160 | 250 | 230 | 200 | 610 |
| 1 | 9 | 15300 | 17750 | 16000 | >30000 | 20940 |
| 2 | 25 | 5890 | 13470 | 18200 | >30000 | 10050 |
| 3 | 19 | 14390 | 11980 | 7160 | >30000 | 17100 |
| 4 | 5 | 23240 | 2480 | 2480 | 3450 | 4900 |
| 5 | 0.5 | 8130 | 660 | 2180 | 5130 | 670 |
| 6 | 1.7 | 11660 | 790 | 1010 | 4830 | 1050 |
| 7 | 1.7 | 4000 | 600 | 1400 | 2300 | 1200 |
| 8 | 14.4 | 11100 | 1100 | 2900 | 6100 | 1700 |
| 9 | 4.4 | 4990 | 350 | 890 | 5100 | 360 |
| 10 | 6 | 14360 | 1770 | 2670 | 5420 | 3780 |
| 11 | 3 | 17920 | 9310 | 10240 | 15410 | 16330 |
| 12 | 0.3 | 13910 | 6980 | 11850 | 23180 | 2660 |
| 13 | 17.4 | >30000 | 7600 | 15100 | >30000 | 23200 |
| 14 | 7.3 | 19000 | 3800 | 7700 | 25900 | 7700 |
| 15 | 5.2 | 6270 | 2970 | 7690 | 19120 | 10570 |
| 16 | 16 | 26720 | 5690 | 9550 | 10480 | 27260 |
| 17 | 2 | >30000 | 3770 | 9570 | >30000 | 15230 |
| 18 | 54 | >30000 | 5160 | 4910 | 15760 | 9800 |
| 19 | 39 | 15290 | 12670 | 12260 | >30000 | 18840 |
| 20 | 6 | >30000 | >30000 | >30000 | >30000 | >30000 |
| 21 | 9 | >30000 | 6350 | 6140 | 7140 | 20890 |
| 22 | 35 | 15290 | 12670 | 12260 | >30000 | 18840 |
| 23 | 64 | 2510 | 220 | 260 | 30 | 2650 |
| 24 | 2 | >30000 | >30000 | >30000 | >30000 | >30000 |
| 25 | 2 | >30000 | 4960 | 15780 | >30000 | >30000 |
| 26 | 5.6 | >30000 | 2150 | 12910 | >30000 | 4440 |
| 27 | 3.6 | >30000 | 12580 | >30000 | >30000 | >30000 |
| 28 | 15 | >30000 | >30000 | >30000 | >30000 | >30000 |
| 29 | 6 | >30000 | >30000 | >30000 | >30000 | >30000 |
| 30 | 76 | nd | nd | nd | nd | nd |
| 31 | 41 | nd | nd | nd | nd | nd |
| 32 | 0.8 | 2900 | 1500 | 1100 | 2100 | 4200 |
| 33 | 0.9 | 10000 | 7600 | 8100 | 15200 | >30000 |
| 34 | 422 | 4000 | 5600 | 4000 | 5500 | 7300 |
| 35 | 56.1 | 4700 | >30000 | 27800 | >30000 | >30000 |
| 36 | 3.7 | 6590 | 4940 | 7500 | 21550 | >30000 |
| 37 | 17 | 24070 | 610 | 1230 | 240 | 960 |
| 38 | 4 | 21680 | 7670 | 7500 | 15400 | 10030 |
| 39 | 35 | 17640 | 11500 | 12350 | >30000 | 18300 |
| 40 | 1.6 | >30000 | 8450 | 10360 | 26850 | 10860 |
| 41 | 3 | 2660 | 810 | 370 | 380 | 2610 |
| 42 | 13 | >30000 | 610 | 530 | 16630 | 10280 |
| 43 | 3.4 | nd | nd | nd | nd | nd |
| 44 | 1.5 | 24270 | 11190 | 8570 | 25270 | 26250 |
| 45 | 30 | 550 | 410 | 100 | 660 | 1430 |
| 46 | 8.7 | 6240 | 1060 | 1180 | 1520 | 2130 |
| 47 | 10.4 | >30000 | >30000 | >30000 | >30000 | >30000 |
| 48 | 15 | 16820 | 10330 | 6000 | 15740 | 21130 |
| 49 | 5.2 | 7340 | 7250 | 6730 | 21190 | 17230 |
| 50 | 28.8 | 5300 | 9000 | 24500 | >30000 | >30000 |
| 51 | 96 | >30000 | >30000 | 20120 | >30000 | >30000 |
| 52 | 216 | 4360 | 200 | 540 | 150 | 1190 |
| 53 | 169 | 2810 | 450 | 1190 | 10 | 1330 |
| 54 | 35 | >30000 | 6350 | 6140 | 7140 | 20890 |
| 55 | 26 | 13020 | >30000 | 22890 | >30000 | >30000 |
| 56 | 101 | 960 | 140 | 130 | 40 | 2420 |
| 57 | 75 | 9160 | 5550 | 14540 | 11470 | >30000 |

TABLE 3-continued

SRPK1 and CYP activity assay data

| Example | SRPK1 ($IC_{50}$/nM) | CYP Inhibition Activity ($IC_{50}$/nM) | | | | |
|---|---|---|---|---|---|---|
| | | CYP1A2 | CYP2C9 | CYP2C19 | CYP2D6 | CYP3A4 |
| 58 | 204 | >30000 | >30000 | >30000 | >30000 | 23200 |
| 59 | 54 | 10500 | 15000 | 10500 | 23900 | >30000 |
| 60 | 71 | >30000 | >30000 | 22600 | >30000 | >30000 |
| 61 | 1.2 | >30000 | 7600 | 10600 | >30000 | >30000 |
| 62 | 1.5 | >30000 | 11000 | 12200 | 24800 | >30000 |
| 63 | 25 | >30000 | 14200 | >30000 | >30000 | >30000 |
| 64 | 5.6 | >30000 | 15800 | >30000 | >30000 | >30000 |
| 65 | 9.8 | >30000 | 14000 | >30000 | >30000 | >30000 |
| 66 | 10 | >30000 | 2000 | 11400 | >30000 | >30000 |
| 67 | 4.1 | >30000 | 3300 | 7900 | >30000 | >30000 |
| 68 | 1.2 | >30000 | 2800 | 11400 | 16100 | 10900 |
| 69 | 4.2 | >30000 | 1600 | 2700 | 2300 | 3600 |
| 70 | 11 | >30000 | 1800 | 2200 | 4700 | 4400 |
| 71 | 2.9 | >30000 | 5420 | 2700 | 8790 | 4190 |
| 72 | 1.9 | >30000 | 2360 | 7540 | 4130 | 2370 |
| 73 | 5.6 | >30000 | 690 | 1870 | 1610 | 470 |
| 74 | 2.9 | >30000 | 1130 | 2890 | 1550 | 720 |
| 75 | 2.8 | >30000 | 4400 | 10830 | 11780 | 10340 |
| 76 | 3.2 | >30000 | 1700 | 4250 | 8680 | 750 |
| 77 | 1.6 | >30000 | 1440 | 4780 | 9540 | 970 |
| 78 | 9.1 | >30000 | 9130 | 20050 | 1290 | 8320 |
| 79 | 263 | >30000 | >30000 | 17800 | 400 | 4500 |
| 80 | 42 | >30000 | 7640 | 7340 | 1040 | 3540 |
| 81 | 2.6 | >30000 | 23000 | 12330 | 5010 | 21160 |
| 82 | 35 | >30000 | >30000 | 29200 | 2800 | 6200 |
| 83 | 3.2 | >30000 | 24320 | >30000 | 3200 | 20990 |
| 84 | 23 | >30000 | 600 | 8000 | 12400 | 2200 |
| 85 | 43 | >30000 | 800 | 21700 | >30000 | 20700 |
| 86 | 9.0 | >30000 | 200 | 4100 | 19200 | 1100 |
| 87 | 27 | >30000 | 800 | 14300 | >30000 | 5900 |
| 88 | 11 | >30000 | 300 | 4600 | 10300 | 1000 |
| 89 | 14 | >30000 | 2500 | 14100 | 18900 | 2800 |
| 90 | 5.5 | >30000 | 1000 | 10300 | 11600 | 2800 |
| 91 | 41 | >30000 | 14900 | 20800 | 200 | 19000 |
| 92 | 150 | >30000 | 10400 | >30000 | 1500 | >30000 |
| 93 | 28 | >30000 | 13700 | 25700 | 24300 | 29500 |
| 94 | 167 | >30000 | 17200 | 25100 | 300 | 23100 |
| 95 | 24 | >30000 | 10100 | >30000 | 400 | 7300 |
| 96 | 49 | >30000 | 17800 | >30000 | 200 | 7700 |
| 97 | 6.0 | >30000 | 200 | 2700 | 8100 | 9400 |
| 98 | 7.5 | >30000 | 18600 | >30000 | >30000 | >30000 |
| 99 | 4.8 | >30000 | >30000 | >30000 | 3000 | 18000 |
| 100 | 2.6 | >30000 | 7300 | 3200 | 13800 | 2700 |
| 101 | 15.1 | >30000 | >30000 | >30000 | 4800 | >30000 |
| 102 | 44.6 | >30000 | 14100 | 9400 | 100 | 3900 |

While the compounds and related aspects have been described with reference to certain examples, those skilled in the art will appreciate that various modifications, changes, omissions, and substitutions can be made without departing from the spirit of the disclosure. It is intended, therefore, that the present compounds and related aspects be limited only by the scope of the following claims. That said, it will be understood that the protection afforded by the following claims is not limited to the literal scope, but extends to equivalent or variant compounds and related aspects in which it is apparent that the equivalent or variant achieves the same technical effects in the same manner, such as, for example replacement of a chloro substituent with a bromo substituent with no significant deviation in biological activity.

The invention claimed is:
1. A compound of Formula (I):

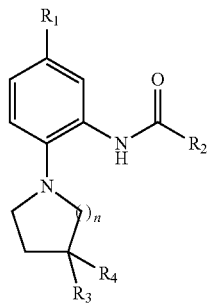

or a pharmaceutically acceptable salt, solvate, hydrate or prodrug thereof, wherein:
n=1, 2 or 3;
$R_1$ is halogen, difluoromethyl, trifluoromethyl, cyclopropyl, methyl, methoxy or trifluoromethoxy;
$R_2$ is furanyl having a 4-pyridyl substituent;
$R_3$ is hydroxyl;
$R_4$ is hydrogen; and
$R_5$ and $R_6$ are independently selected from hydrogen, methyl, ethyl or propyl; or
$R_5$ and $R_6$ are joined together to form a nitrogen-containing heterocycle.

2. The compound according to claim 1, wherein: $R_1$ is chloro, trifluoromethyl or cyclopropyl.

3. A pharmaceutical composition comprising a compound of claim 1, optionally one or more other active ingredients and a pharmaceutically acceptable carrier.

4. The pharmaceutical composition of claim 3, in a form suitable for: intraocular injection, topical administration to the eye, or systemic administration.

5. A method of treating or preventing ocular neovascularisation, comprising administering a therapeutically effective amount of a compound according to claim 1 to a subject in need thereof.

6. The method of claim 5, wherein the treatment is a dose-dependent treatment and/or a topical treatment.

7. The method of claim 5, wherein treatment of ocular neovascularisation comprises treatment of age related macular degeneration or macular oedema.

8. A method of inhibiting SRPK1 to thereby treat or prevent a disease or condition in a subject in need thereof, said method comprising administering a therapeutically effective amount of a SRPK1-specific inhibitor compound according to claim 1 to said subject.

9. The method of claim 8, wherein said disease or condition is selected from the group consisting of abnormal angiogenesis, over-production of pro-angiogenic VEGF isoforms in a mammalian subject, microvascular hyperpermeability, fibrosis, cancer, neurodegeneration, neuropathy, and pain.

* * * * *